United States Patent [19]

Almansa et al.

[11] Patent Number: 5,827,863
[45] Date of Patent: Oct. 27, 1998

[54] PYRAZOLE DERIVATIVES AS ANGIOTENSIN II ANTAGONISTS

[75] Inventors: Carmen Almansa; Concepción Gonzalez; M. Carmen Torres; Elena Carceller; Javier Batroli, all of Barcelona, Spain

[73] Assignee: J. Uriach & Cia, S.A., Barcelona, Spain

[21] Appl. No.: 624,459

[22] PCT Filed: Aug. 2, 1995

[86] PCT No.: PCT/EP95/03086

§ 371 Date: Jun. 20, 1996

§ 102(e) Date: Jun. 20, 1996

[87] PCT Pub. No.: WO96/04273

PCT Pub. Date: Feb. 15, 1996

[30] Foreign Application Priority Data

Aug. 2, 1994 [ES] Spain ..................... 9401711

[51] Int. Cl.⁶ .................. A01K 31/44; C07D 401/00; C07D 757/00; C07F 9/06
[52] U.S. Cl. .................. 514/341; 514/406; 546/275.4; 546/364.1; 548/119; 548/252; 548/374.1; 548/375.1
[58] Field of Search .................. 514/406, 341; 546/275.4, 364.1; 548/252, 374.1, 375.1, 376.1, 119

[56] References Cited

U.S. PATENT DOCUMENTS 5,298,519 3/1994 Binder et al. .................. 514/381
5,389,659 2/1995 Ross et al. .................. 514/381

OTHER PUBLICATIONS

Middlemiss et al., "C–Linked Pyrazole Biaryl Tetrazoles as Antagonists of Angiotensin II," Bioorganic & Medicinal Chemistry Letters, vol. 2, No. 10, pp. 1243–1246, 1992.

*Primary Examiner*—Deborah C. Lambkin
*Assistant Examiner*—Joseph Murray
*Attorney, Agent, or Firm*—Burns, Doane, Swecker & Mathis, L.L.P.

[57] ABSTRACT

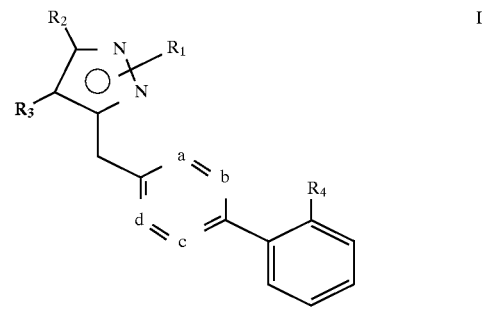

Compounds of general formula I and their salts and solvates are angiotensin II receptor antagonists and as such are useful in the treatment of hypertension, congestive heart failure and elevated intraocular pressure. Pharmaceutical compositions including these compounds and processes for their preparation are also provided.

19 Claims, No Drawings

PYRAZOLE DERIVATIVES AS ANGIOTENSIN II ANTAGONISTS

This application is a national stage application based on PCT/EP95/03086, which was filed on Aug. 2, 1995.

FIELD OF THE INVENTION

The present invention relates to new pyrazole derivatives which are potent angiotensin II antagonists. The invention also relates to a process for their preparation, to the pharmaceutical compositions containing them and to their use for the manufacture of medicaments for the treatment or prevention of hypertension, congestive heart failure, elevated intraocular pressure and other diseases or medical conditions in which the action of angiotensin II is implicated.

DESCRIPTION OF THE PRIOR ART

The renin-angiotensin system (RAS) plays a key role in the regulation of blood pressure and volume homeostasis. Activation of the renin-angiotensin cascade begins with renin secretion from the juxtaglomerular apparatus of the kidney and culminates in the formation of the octapeptide angiotensin II.

Angiotensin II exerts its biological effects via interactions with specific receptors present in many tissues. Two basic types of angiotensin II receptors have been characterized so far, both with a broad distribution: the $AT_1$ receptors, responsible for the majority of effects attributed to this peptide, and the $AT_2$ receptors, the functional role of which has not yet been identified.

The main effects of angiotensin II are the regulation of blood pressure through vasoconstriction thereby effecting an increase in vascular resistances, the regulation of volemia through the stimulation of the release of vasopressin and particularly aldosterone, which induces saline retention, and the regulation of the adrenocorticotropic hormone (ACTH). Angiotensin II can act as a neuropeptide at the central nervous system and can play a modulating function in the release of other neurotransmiters.

Furthermore, it has been described that the administration of angiotensin II to either the rat brain dorsal neostriatum or the lateral ventricle produces alterations in the rat cognitive responses. This fact suggests that probably angiotensin II is involved in several cerebral processes related with the learning function, memory and the like.

One of the possible modes of interfering with the RAS is to block the action of angiotensin II at the receptor level. Although several peptidic analogues of angiotensin II having greater affinity for its receptors than angiotensin II itself have been discovered, their therapeutic use has been severely limited by their lack of bioavailability and short duration of action.

More recently, several nonpeptide angiotensin II receptor antagonists have been reported in the literature. Patent applications EP 253310 and WO 93/05025 disclose compounds related to those described in the present invention.

DESCRIPTION OF THE INVENTION

The present invention relates to novel pyrazoles of general formula I:

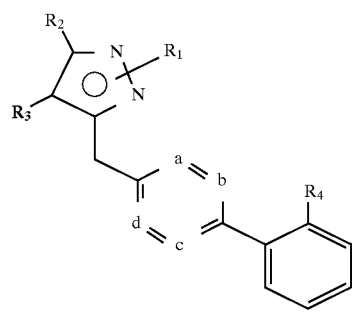

wherein:
$R_1$ represents hydrogen, $C_{1-6}$ alkyl, $C_{1-6}$ haloalkyl, $C_{3-7}$ cycloalkyl, aryl, or —$(CH_2)_mCOR_5$;
$R_2$ represents hydrogen, halogen, $C_{1-6}$ alkyl, $C_{1-6}$ haloalkyl, $C_{3-7}$ cycloalkyl, $C_{3-7}$ cycloalkyl$C_{1-4}$ alkyl, $C_{1-6}$ hydroxyalkyl, $C_{1-6}$ alkoxy$C_{1-4}$ alkyl, aryl or aryl$C_{1-4}$ alkyl;
$R_3$ represents hydrogen, —$(CH_2)_nR_6$ or —$(CH_2)_pCOR_7$;
either a, b, c and d represent CR or one of a, b, c and d represents N and the remaining groups represent CR, wherein each R independently represents hydrogen, halogen, $C_{1-4}$ alkyl, hydroxy, $C_{1-4}$ alkoxy, nitro, amino, $C_{1-4}$ alkylamino or $C_{1-4}$ dialkylamino;
$R_4$ represents —$CO_2R_8$; -tetrazol-5-yl; tetrazol-5-ylmethyl; —CONH(tetrazol-5-yl); —$CONHSO_2R_9$; —$CONHSO_2$—Het; —$CONHOR_8$; —$CONH_2$; —$CONR_8R_9$; —$COCH_2COR_8$; —$COCH_2CO_2R_8$; —$CONHNHSO_2R_9$; —$CONHNHCONH_2$; —$CH_2NHSO_2R_9$; —$CH_2CO_2R_8$; —$CH_2SO_2NHCOR_8$; —$CH_2SO_2NHCONHR_8$; —$CH_2CONHSO_2R_9$; —$CH_2SO_2NH$—Het; —$CH_2NHCOR_8$; —$NHSO_2R_9$; —$NHCOR_8$; —$NHCONHSO_2R_9$; —$NHSO_2NHCOR_8$; —$SO_3H$; —$SO_2NHR_8$; —$SO_2NHCONH_2$; —$SO_2NHCONR_8R_9$; —$SO_2NHCO_2R_9$; —$SO_2N(CO_2R_9)_2$; —$SO_2NHCOR_8$; —$SO_2NH$—Het; —$SO_2NHCO$—Het; —$PO(OH)_2$; —$PO(OR_9)_2$; —PO(OH)(OR_9)$; or 3-(trifluoromethyl)-1,2,4-triazol-5-yl; wherein Het represents a 5- or 6-membered aromatic heterocycle in which from 1 to 3 of the ring atoms are nitrogen and/or oxygen and/or sulphur and which can be optionally substituted with one or two groups chosen from hydroxy, mercapto, $C_{1-4}$ alkyl, $C_{1-4}$ alkoxy, halogen, nitro, $CO_2H$, $CO_2C_{1-4}$ alkyl, amino , $C_{1-4}$ alkylamino and $C_{1-4}$ dialkylamino; and $R_8$ represents hydrogen, $C_{1-4}$ alkyl, aryl, aryl-($C_{1-4}$)alkyl or perfluoro-($C_{1-4}$)alkyl, and $R_9$ represents $C_{1-4}$ alkyl, aryl, aryl-($C_{1-4}$)alkyl or perfluoro-($C_{1-4}$)alkyl;
$R_5$ represents hydrogen, hydroxy, $C_{1-6}$ alkyl, $C_{1-6}$ alkoxy, aryl, aryloxy or a group —$NR_{10}R_{11}$;
$R_6$ represents hydroxy, $C_{1-6}$ alkoxy, aryloxy, aryl$C_{1-4}$ alkoxy or $C_{1-6}$ alkylcarbonyloxy;
$R_7$ represents hydrogen, hydroxy, $C_{1-6}$ alkyl, $C_{1-6}$ alkoxy, aryl, aryloxy, aryl$C_{1-4}$ alkoxy, carboxy, $C_{1-4}$ alkoxycarbonyl, a group —$OR_{12}$ or a group —$NR_{10}R_{11}$;
$R_{10}$ and $R_{11}$ independently represent hydrogen or $C_{1-6}$ alkyl;
$R_{12}$ represents $C_{1-6}$ alkylcarbonyloxy$C_{1-4}$ alkyl, $C_{3-7}$ cycloalkylcarbonyloxy$C_{1-4}$ alkyl, $C_{1-6}$ alkoxycarbonyloxy$C_{1-4}$ alkyl, $C_{3-7}$ cycloalkyloxycarbonyloxy$C_{1-4}$ alkyl, $C_{1-6}$ alkoxycarbonyl$C_{1-4}$ alkyl, $C_{3-7}$ cycloalkyloxycarbonyl- $C_{1-4}$ alkyl, $C_{1-6}$ alkylcarbonylamino$C_{1-4}$ alkyl, $C_{3-7}$ cycloalkylcarbonylamino$C_{1-4}$ alkyl, a group of formula —(CH$_2$)$_q$R$_{13}$, or a group of formula —(CH$_2$)$_r$OR$_{13}$;

R$_{13}$ represents phenyl optionally substituted with a group arylcarbonyl, $C_{1-6}$ alkylcarbonyl or aryloxy;

m, n, q and r independently represent 1, 2 or 3;

p represents 0, 1 or 2;

aryl, whenever appearing in the above definitions, represents phenyl or phenyl substituted with 1, 2, 3 or 4 groups selected from $C_{1-4}$ alkyl, $C_{1-4}$ haloalkyl, $C_{1-4}$ alkoxy, $C_{1-4}$ haloalkoxy, halogen, nitro, cyano, hydroxy, amino, $C_{1-4}$ alkylamino or $C_{1-4}$ dialkylamino; and the salts and solvates thereof.

The present invention also provides a pharmaceutical composition which comprises an effective amount of a compound of formula I or a pharmaceutically acceptable salt or solvate thereof in admixture with a pharmaceutically acceptable excipient.

The invention further provides the use of a compound of formula I or a pharmaceutically acceptable salt or solvate thereof for the manufacture of a medicament for the treatment or prevention of diseases or medical conditions in which angiotensin II is involved in a mammal, which may be a human being. Preferred is the use for the manufacture of a medicament for the treatment or prevention of hypertension, congestive heart failure and elevated intraocular pressure.

The invention also provides the use of a compound of formula I or a pharmaceutically acceptable salt or solvate thereof for the treatment or prevention of diseases or medical conditions in which angiotensin II is involved in a mammal, which may be a human being. Preferred is the use for the treatment or prevention of hypertension, congestive heart failure and elevated intraocular pressure.

The invention further provides a method of treating diseases or medical conditions in which. angiotensin II is involved in a mammal, which comprises administering to said mammal an effective amount of a compound of formula I or a pharmaceutically acceptable salt or solvate thereof. Preferred is a method of treating or preventing hypertension, congestive heart failure and elevated intraocular pressure in a mammal in need thereof, the method comprising administering to the mammal an effective amount of a compound of formula I or a pharmaceutically acceptable salt or solvate thereof.

The invention still further provides a process for preparing a compound of formula I, which comprises:

A) reacting a compound of formula II with a compound of formula III

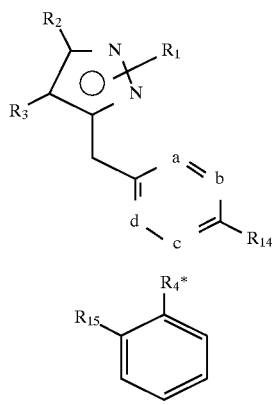

(wherein a, b, c, d, R$_1$, R$_2$ and R$_3$ have the previously described meaning, R$_4$* represents a group R$_4$ or a group convertible thereto, and either one of R$_{14}$ and R$_{15}$ represents halogen, methanesulfonyloxy, toluenesulfonyloxy or trifluoromethanesulfonyloxy and the other represents a group —Sn(R$_{16}$)$_3$, —B(OH)$_2$ or —B(OR$_{17}$)(OR$_{18}$) or both of them represent halogen, wherein R$_{16}$ represents a $C_{1-4}$ alkyl group and R$_{1-7}$ and R$_{1-8}$ represent each $C_{1-4}$ alkyl or R$_{17}$ and R$_{18}$ together with the oxygen atoms to which they are linked and the boron atom form a 1,3,2-dioxaborane or a 1,3,2-dioxaborolane ring, which may be optionally substituted with $C_{1-4}$ alkyl groups), followed, if necessary, by the conversion of a group R$_4$* into a group R$_4$ and/or the removal of any protecting group present; or B) reacting a compound of formula IV

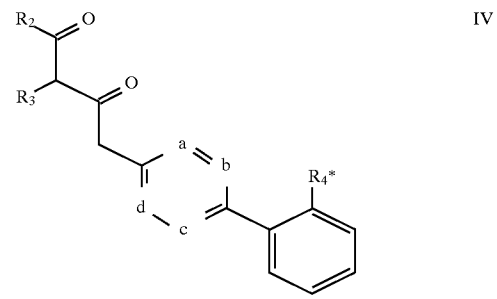

(wherein a, b, c, d, R$_2$ and R$_3$ have the previously described meaning and R$_4$* represents a group R$_4$ or a group convertible thereto) with a compound of formula R$_1$NHNH$_2$ (V), followed, if necessary, by the conversion of a group R$_4$* into a group R$_4$ and/or the removal of any protecting group present; or C) deprotecting a compound of formula I'

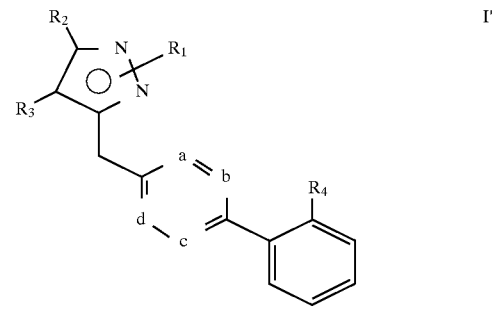

wherein a, b, c, d, R$_1$, R$_2$, R$_3$ and R$_4$ have the previously described meaning but at least one of them contains a protecting group; or D) converting, in one or a plurality of steps, a compound of formula I into another compound of formula I; and E) if desired, after steps A, B, C or D treating a compound of formula I with an acid or a base to give the corresponding salt.

The compounds of formula II are valuable intermediates in the preparation of the compounds of the present invention, as are other novel compounds specifically or generically disclosed herein. According to a further aspect of the present invention, there is therefore provided a compound of general formula II.

In the above definitions, the term $C_{1-n}$ alkyl, as a group or part of a group, means a linear or branched alkyl chain containing from 1 to n carbon atoms. Therefore, when n is 4 it includes the groups methyl, ethyl, propyl, isopropyl, butyl, isobutyl, sec-butyl and tert-butyl. When n is 6 it includes, among others, methyl, ethyl, propyl, isopropyl, butyl, isobutyl, sec-butyl, tert-butyl, pentyl, isopentyl, neopentyl, hexyl, isohexyl, 1-methylpentyl, 2-methylpentyl, 3-methylpentyl.

The term $C_{1-n}$ alkoxy, as a group or part of a group, means a group derived from the union of a $C_{1-n}$ alkyl group to an oxygen atom of an ether functional group. When n is 4, this term includes the groups methoxy, ethoxy, propoxy, isopropoxy, butoxy, isobutoxy, sec-butoxy and tert-butoxy. When n is 6, it includes among others, methoxy, ethoxy, propoxy, isopropoxy, butoxy, isobutoxy, sec-butoxy, tert-butoxy, pentyloxy, isopentyloxy, neopentyloxy, hexyloxy, isohexyloxy, 1-methylpentyloxy, 2-methylpentyloxy, 3-methylpentyloxy.

A halogen atom means fluorine, chlorine, bromine or iodine.

A $C_{1-6}$ haloalkyl group means a group resulting from the substitution of one or more hydrogen atoms of a $C_{1-6}$ alkyl group by one or more halogen atoms (i.e. fluorine, chlorine, bromine or iodine), which can be the same or different. Examples include trifluoromethyl, fluoromethyl, chloroethyl, fluoroethyl, iodoethyl, 2,2,2-trifluoroethyl, pentafluoroethyl, fluoropropyl, chloropropyl, 2,2,3,3,3-pentafluoropropyl, heptafluoropropyl, fluorobutyl, nonafluorobutyl, fluoropentyl, fluorohexyl.

A perfluoro-$(C_{1-4})$alkyl group means a group resulting from the substitution of all hydrogen atoms of a $C_{1-4}$ alkyl group by fluorine atoms. Examples include trifluoromethyl, pentafluoroethyl, heptafluoropropyl, and nonafluorobutyl.

A $C_{1-6}$ hydroxyalkyl group means a group resulting from the substitution of one hydrogen atom of a $C_{1-6}$ alkyl group by one hydroxyl group. Examples include hydroxymethyl, 2-hydroxyethyl, 1-hydroxyethyl, 3-hydroxypropyl, 2-hydroxypropyl, 4-hydroxybutyl, 3-hydroxybutyl, 2-hydroxybutyl, 1-hydroxybutyl, 5-hydroxypentyl, 6-hydroxyhexyl.

The term $C_{3-7}$ cycloalkyl, as a group or part of a group, represents cyclopropyl, cyclobutyl, cyclopentyl, cyclohexyl or cycloheptyl.

A $C_{3-7}$ cycloalkyl$C_{1-4}$ alkyl group represents a group resulting from the substitution of one hydrogen atom of a $C_{1-4}$ alkyl group by a $C_{3-7}$ cycloalkyl group; examples include among others cyclopropylmethyl, cyclobutylmethyl, cyclopentylmethyl, and cyclohexylmethyl.

A $C_{1-4}$ alkylamino or $C_{1-4}$ dialkylamino group represents a group resulting from the substitution of one or two hydrogen atoms, respectively, of an amino group by one or two $C_{1-4}$ alkyl groups, which can be the same or different. Examples include methylamino, dimethylamino, ethylamino, diethylamino, ethylmethylamino, propylamino, dipropylamino, isopropylamino and diisopropylamino.

A group aryl$C_{1-4}$ alkyl represents a group resulting from the substitution of one hydrogen atom of a $C_{1-4}$ alkyl group by a group aryl, such as for example a group benzyl.

A group aryl$C_{1-4}$ alkoxy represents a group resulting from the union of a aryl$C_{1-4}$ alkyl group to an oxygen atom of an ether functional group, such as for example a group benzyloxy.

Examples of a group $C_{1-6}$ alkylcarbonyloxy$C_{1-4}$ alkyl include formyloxymethyl, acetoxymethyl, propionyloxymethyl, butyryloxymethyl, isobutyryloxymethyl, pivaloyloxymethyl, valeryloxymethyl, isovaleryl-oxymethyl, hexanoyloxymethyl, 1-(formyloxy)ethyl, 1-(acetoxy)ethyl, 1-(propionyloxy)ethyl, 1-(butyryloxy)ethyl, 1-(isobutyryloxy)ethyl, 1-(pivaloyloxy)ethyl, 1-(valeryloxy)ethyl, 1-(isovaleryloxy)ethyl, 1-(hexanoyloxy)ethyl, 2-(formyloxy)ethyl, 2-(acetoxy)ethyl, 2-(propionyloxy)ethyl, 2-(butyryloxy)ethyl, 2-(isobutyryloxy)ethyl, 2-(pivaloyloxy)ethyl, 2-(valeryloxy)ethyl, 2-(isovaleryloxy)ethyl, 2-(hexanoyloxy)ethyl, 1-(formyloxy)propyl, 1-(acetoxy)propyl, 1-(propionyloxy)propyl, 1-(butyryloxy)propyl, 1-(isobutyryloxy)propyl, 1-(pivaloyloxy)propyl, 1-(valeryloxy)propyl, 1-(isovaleryloxy)propyl, 1-(hexanoyloxy)propyl, 1-(formyloxy)butyl, 1-(acetoxy)butyl, 1-(propionyloxy)butyl, 1-(butyryloxy)butyl, 1-(isobutyryloxy)butyl, 1-(pivaloyloxy)butyl, 1-(valeryloxy)butyl, 1-(isovaleryloxy)butyl, and 1-(hexanoyloxy)butyl.

Examples of a group $C_{3-7}$ cycloalkylcarbonyloxy$C_{1-4}$ alkyl include cyclopropylcarbonyloxymethyl, cyclobutylcarbonyloxymethyl, cyclopentylcarbonyloxymethyl, cyclohexylcarbonyloxymethyl, cycloheptylcarbonyloxymethyl, 1-(cyclopropylcarbonyloxy)ethyl, 1-(cyclobutylcarbonyloxy)ethyl, 1-(cyclopentylcarbonyloxy)ethyl, 1-(cyclohexylcarbonyloxy)ethyl, 1-(cycloheptylcarbonyloxy)ethyl, 1-(cyclopropylcarbonyloxy)propyl, 1-(cyclobutylcarbonyloxy)propyl, 1-(cyclopentylcarbonyloxy)propyl, 1-(cyclohexylcarbonyloxy)propyl, 1-(cycloheptylcarbonyloxy)propyl, 1-(cyclopropylcarbonyloxy)butyl, 1-(cyclobutylcarbonyloxy)butyl, 1-(cyclopentylcarbonyloxy)butyl, 1-(cyclohexylcarbonyloxy)butyl and 1-(cycloheptylcarbonyloxy)butyl.

Examples of a group $C_{1-6}$ alkoxycarbonyloxy$C_{1-4}$ alkyl include methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, sec-butoxycarbonyloxymethyl, tert-butoxycarbonyloxymethyl, pentyloxycarlonyloxymethyl, isopentyloxycarbonyloxymethyl, neopentyloxycarbonyloxymethyl, hexyloxycarbonyloxymethyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(sec-butoxycarbonyloxy)ethyl, 1-(tert-butoxycarbonyloxy)ethyl, 1-(pentyloxycarbonyloxy)ethyl, 1-(isopentyloxycarbonyloxy)ethyl, 1-(neopentyloxycarbonyloxy)ethyl, 1-(hexyloxycarbonyloxy)ethyl, 2-(methoxycarbonyloxy)ethyl, 2-(ethoxycarbonyloxy)ethyl, 2-(propoxycarbonyloxy)ethyl, 2-(isopropoxycarbonyloxy)ethyl, 2-(butoxycarbonyloxy)ethyl, 2-(isobutoxycarbonyloxy)ethyl, 2-(sec-butoxycarbonyloxy)ethyl, 2-(tert-butoxycarbonyloxy)ethyl, 2-(pentyloxycarbonyloxy)ethyl, 2-(isopentyloxycarbonyloxy)ethyl, 2-(neopentyloxycarbonyloxy)ethyl, 2-(hexyloxycarbonyloxy)ethyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(sec-butoxycarbonyloxy)propyl, 1-(tert-butoxycarbonyloxy)propyl, 1-(pentyloxycarbonyloxy)propyl, 1-(isopentyloxycarbonyloxy)propyl, 1-(neopentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)

butyl, 1-(butoxycarbonyloxy)butyl, 1-(isobutoxycarbonyloxy)butyl, 1-(sec-butoxycarbonyloxy) butyl, 1-(tertbutoxycarbonyloxy)butyl, 1-(pentyloxycarbonyloxy)butyl, 1-(isopentyloxycarbonyloxy)butyl, 1-(neopentyloxycarbonyloxy)butyl, and 1-(hexyloxycarbonyloxy)butyl.

Examples of a group $C_{3-7}$ cycloalkyloxycarbonyloxy$C_{1-4}$ alkyl include cyclopropyloxycarbonyloxymethyl, cyclobutyloxycarbonyloxymethyl, cyclopentyloxycarbonyloxymethyl, cyclohexyloxycarbonyloxymethyl, cycloheptyloxycarbonyloxymethyl, 1-(cyclopropyloxycarbonyloxy)ethyl, 1-(cyclobutyloxycarbonyloxy)ethyl, 1-(cyclopentyloxycarbonyloxy)ethyl, 1-(cyclohexyloxycarbonyloxy)ethyl, 1-(cycloheptyloxycarbonyloxy)ethyl, 1-(cyclopropyloxycarbonyloxy)propyl, 1-(cyclobutyloxycarbonyloxy)propyl, 1-(cyclopentyloxycarbonyloxy)propyl, 1-(cyclohexyloxycarbonyloxy)propyl, 1-(cycloheptyloxycarbonyloxy)propyl, 1-(cyclopropyloxycarbonyloxy)butyl, 1-(cyclobutyloxycarbonyloxy)butyl, 1-(cyclopentyloxycarbonyloxy)butyl, 1-(cyclohexyloxycarbonyloxy)butyl and 1-(cycloheptyloxycarbonyloxy)butyl.

Examples of a group $C_{1-6}$ alkoxycarbonyl$C_{1-4}$ alkyl include methoxycarbonylmethyl, ethoxycarbonylmethyl, propoxycarbonylmethyl, isopropcycarbonylmethyl, butoxycarbonylmethyl, isobutoxycarbonylmethyl, sec-butoxycarbonylmethyl, tert-butoxycarbonylmethyl, pentyloxycarbonylmethyl, isopentyloxycarbonylmethyl, neopentyloxycarbonylmethyl, hexyloxycarbonylmethyl, 1-(methoxycarbonyl)ethyl, 1-(ethoxycarbonyl)ethyl, 1-(propoxycarbonyl)ethyl, 1-(isopropoxycarbonyl)ethyl, 1-(butoxycarbonyl)ethyl, 1-(isobutoxycarbonyl)ethyl, 1-(sec-butoxycarbonyl)ethyl, 1-(tert-butoxycarbonyl)ethyl, 1-(pentyloxycarbonyl)ethyl, 1-(isopentyloxycarbonyl)ethyl, 1-(neopentyloxycarbonyl)ethyl, 1-(hexyloxycarbonyl)ethyl, 2-(methoxycarbonyl)ethyl, 2-(ethoxycarbonyl)ethyl, 2-(propoxycarbonyl)ethyl, 2-(isopropoxycarbonyl)ethyl, 2-(butoxycarbonyl)ethyl, 2-(isobutoxycarbonyl)ethyl, 2-(sec-butoxycarbonyl)ethyl, 2-(tert-butoxycarbonyl)ethyl, 2-(pentyloxycarbonyl)ethyl, 2-(isopentyloxycarbonyl)ethyl, 2-(neopentyloxycarbonyl)ethyl, 2-(hexyloxycarbonyl)ethyl, 1-(methoxycarbonyl)propyl, 1-(ethoxycarbonyl)propyl, 1-(propoxycarbonyl)propyl, 1-(isopropoxycarbonyl)propyl, 1-(butoxycarbonyl)propyl, 1-(isobutoxycarbonyl)propyl, 1-(sec-butoxycarbonyl)propyl, 1-(tert-butoxycarbonyl)propyl, 1-(pentyloxycarbonyl)propyl, 1-(isopentyloxycarbonyl)propyl, 1-(neopentyloxycarbonyl)propyl, 1-(hexyloxycarbonyl)propyl, 1-(methoxycarbonyl)butyl, 1-(ethoxycarbonyl)butyl, 1-(propoxycarbonyl)butyl, 1-(isopropoxycarbonyl)butyl, 1-(butoxycarbonyl)butyl, 1-(isobutoxycarbonyl)butyl, 1-(sec-butoxycarbonyl)butyl, 1-(tert-butoxycarbonyl)butyl, 1-(pentyloxycarbonyl)butyl, 1-(isopentyloxycarbonyl)butyl, 1-(neopentyloxycarbonyl)butyl, and 1-(hexyloxycarbonyl)butyl.

Examples of a group $C_{3-7}$ cycloalkyloxycarbonyl$C_{1-4}$ alkyl include cyclopropyloxycarbonylmethyl, cyclobutyloxycarbonylmethyl, cyclopentyloxycarbonylmethyl, cyclohexyloxycarbonylmethyl, cycloheptyloxycarbonylmethyl, 1-(cyclopropyloxycarbonyl)ethyl, 1-(cyclobutyloxycarbonyl)ethyl, 1-(cyclopentyloxycarbonyl)ethyl, 1-(cyclohexyloxycarbonyl)ethyl, 1-(cycloheptyloxycarbonyl)ethyl, 1-(cyclopropyloxycarbonyl)propyl, 1-(cyclobutyloxycarbonyl)propyl, 1-(cyclopentyloxycarbonyl)propyl, 1-(cyclohexyloxycarbonyl)propyl, 1-(cycloheptyloxycarbonyl)propyl, 1-(cyclopropyloxycarbonyl)butyl, 1-(cyclobutyloxycarbonyl)butyl, 1-(cyclopentyloxycarbonyl)butyl, 1-(cyclohexyloxycarbonyl)butyl and 1-(cycloheptyloxycarbonyl)butyl.

Examples of a group $C_{1-6}$ alkylcarbonylamino$C_{1-4}$ alkyl include methylcarbonylaminomethyl, ethylcarbonylaminomethyl, propylcarbonylaminomethyl, isopropylcarbonylaminomethyl, butylcarbonylaminomethyl, isobutylcarbonylaminomethyl, sec-butylcarbonylaminomethyl, tert-butylcarbonylaminomethyl, pentylcarbonylaminomethyl, isopentylcarbonylaminomethyl, neopentylcarbonylaminomethyl, hexylcarbonylaminomethyl, 1-(methylcarbonylamino)ethyl, 1-(ethylcarbonylamino)ethyl, 1-(propylcarbonylamino)ethyl, 1-(isopropylcarbonylamino)ethyl, 1-(butylcarbonylamino)ethyl, 1-(isobutylcarbonylamino)ethyl, 1-(sec-butylcarbonylamino)ethyl, 1-(tert-butylcarbonylamino)ethyl, 1-(pentylcarbonylamino)ethyl, 1-(isopentylcarbonylamino)ethyl, 1-(neopentylcarbonylamino)ethyl, 1-(hexylcarbonylamino)ethyl, 1-(methylcarbonylamino)propyl, 1-(ethylcarbonylamino)propyl, 1-(propylcarbonylamino)propyl, 1-(isopropylcarbonylamino)propyl, 1-(butylcarbonylamino)propyl, 1-(isobutylcarbonylamino)propyl, 1-(sec-butylcarbonylamino)propyl, 1-(tert-butylcarbonylamino)propyl, 1-(pentylcarbonylamino)propyl, 1-(isopentylcarbonylamino)propyl, 1-(neopentylcarbonylamino)propyl, 1-(hexylcarbonylamino)propyl, 1-(methylcarbonylamino)butyl, 1-(ethylcarbonylamino)butyl, 1-(propylcarbonylamino)butyl, 1-(isopropylcarbonylamino)butyl, 1-(butylcarbonylamino)butyl, 1-(isobutylcarbonylamino)butyl, 1-(sec-butylcarbonylamino)butyl, 1-(tert-butylcarbonylamino)butyl, 1-(pentylcarbonylamino)butyl, 1-(isopentylcarbonylamino)butyl, 1-(neopentylcarbonylamino)butyl and 1-(hexylcarbonylamino)butyl.

Examples of a group $C_{3-7}$ cycloalkylcarbonylamino$C_{1-4}$ alkyl include cyclopropylcarbonylaminomethyl, cyclobutylcarbonylaminomethyl, cyclopentylcarbonylaminomethyl, cyclohexylcarbonylaminomethyl, cycloheptylcarbonylaminomethyl, 1-(cyclopropylcarbonylamino)ethyl, 1-(cyclobutylcarbonylamino)ethyl, 1-(cyclopentylcarbonylamino)ethyl, 1-(cyclohexylcarbonylamino)ethyl, 1-(cycloheptylcarbonylamino)ethyl, 1-(cyclopropylcarbonylamino)propyl, 1-(cyclobutylcarbonylamino)propyl, 1-(cyclopentylcarbonylamino)propyl, 1-(cyclohexylcarbonylamino)propyl, 1-(cycloheptylcarbonylamino)propyl, 1-(cyclopropylcarbonylamino)butyl, 1-(cyclobutylcarbonylamino)butyl, 1-(cyclopentylcarbonylamino)butyl, 1-(cyclohexylcarbonylamino)butyl and 1-(cycloheptylcarbonylamino)butyl.

Examples of the group Het defined above in connection with the substituent $R_4$ include pyridine, pyrimidine, pyrazine, pyridazine, furan, pyrrole, tiophene, imidazole, triazole, thiazole, oxazole and isoxazole.

Preferred compounds of the present invention include those in which, independently or in any compatible combination:

$R_1$ is adjacent to the biphenylmethyl or phenylpyridylmethyl moiety;

$R_1$ represents $C_{1-6}$ alkyl;

a, b, c and d are each CR;

$R_2$ represents hydrogen, $C_{1-6}$ alkyl, $C_{3-7}$ cycloalkyl, $C_{3-7}$ cycloalkyl$C_{1-4}$ alkyl, aryl or aryl$C_{1-4}$ alkyl;

$R_3$ represents —$COR_7$; and $R_4$ represents —$CO_2R_8$; -tetrazol-5-yl; —$NHSO_2R_9$; —$SO_2NHR_8$; —$SO_2NHCO_2R_9$ or —$SO_2NHCOR_8$.

Accordingly, a preferred class of compounds of formula I is that wherein $R_1$ is adjacent to the biphenylmethyl or phenylpyridylmethyl moiety, thus providing compounds represented by formula Ia:

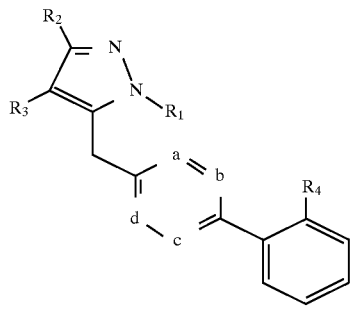

wherein a, b, c, d, $R_1$, $R_2$, $R_3$ and $R_4$ have the meaning defined above for formula I.

A more preferred class of compounds of formula I is that of formula Ia wherein:

$R_1$ represents $C_{1-6}$ alkyl; and a, b, c, d, $R_2$, $R_3$ and $R_4$ have the previously defined meaning.

A further preferred class of compounds of formula I is that of formula Ia wherein:

$R_1$ represents $C_{1-6}$ alkyl;

a, b, c and d are each CR; and

R, $R_2$, $R_3$ and $R_4$ have the previously defined meaning.

A yet more preferred class of compounds of formula I is that of formula Ia wherein:

$R_1$ represents $C_{2-4}$ alkyl;

a, b, c and d are each CR;

$R_2$ represents hydrogen, $C_{1-6}$ alkyl, $C_{3-7}$ cycloalkyl, $C_{3-7}$ cycloalkyl$C_{1-4}$ alkyl, aryl or aryl$C_{1-4}$ alkyl; and R, $R_3$ and $R_4$ have the previously defined meaning.

An even more preferred class of compounds of formula I is that of formula Ia wherein:

$R_1$ represents $C_{2-4}$ alkyl;

a, b, c and d are each CR;

$R_2$ represents hydrogen, $C_{1-6}$ alkyl, $C_{3-7}$ cycloalkyl, $C_{3-7}$ cycloalkyl$C_{1-4}$ alkyl, aryl or aryl$C_{1-4}$ alkyl;

$R_3$ represents —$COR_7$; and

R, $R_4$ and $R_7$ have the previously defined meaning.

A particularly preferred class of compounds of formula I is that of formula Ia wherein:

$R_1$ represents $C_{2-4}$ alkyl;

a, b, c and d are each CR;

$R_2$ represents hydrogen, $C_{1-6}$ alkyl, $C_{3-7}$ cycloalkyl, $C_{3-7}$ cycloalkyl$C_{1-4}$ alkyl, aryl or aryl$C_{1-4}$ alkyl;

$R_3$ represents —$COR_7$;

$R_4$ represents —$CO_2R_8$; -tetrazol-5-yl; —$NHSO_2R_9$; —$SO_2NHR_8$; —$SO_2NHCO_2R_9$ or —$SO_2NHCOR_8$; and R, $R_7$, $R_8$ and $R_9$ have the previously defined meaning.

The compounds of the present invention contain one or more basic nitrogen atoms and can contain one or more acid hydrogen atoms and, consequently, they can form salts with acids and bases both organic and inorganic, which salts are also included in the present invention. There is no limitation on the nature of these salts, provided that, when used for therapeutic purposes, they are pharmaceutically acceptable, which, as is well known in the art, means that they do not have reduced activity (or unacceptable reduced activity) or increased toxicity (or unacceptable increased toxicity) compared with the free compounds. Examples of these salts include: salts with inorganic cations such as sodium, potassium, calcium, magnesium, lithium, aluminium, zinc, etc; and salts formed with pharmaceutically acceptable amines such as ammonia, alkylamines, hydroxyalkylamines, lysine, arginine, N-methylglucamine, procaine and the like; salts with inorganic acids such as hydrochloric acid, hydrobromic acid, hydriodic acid, nitric acid, perchloric acid, sulfuric acid, or phosphoric acid; and salts with organic acids, such as methanesulfonic acid, trifluoromethanesulfonic acid, ethanesulfonic acid, benzenesulfonic acid, p-toluenesulfonic acid, fumaric acid, oxalic acid or maleic acid. The salts are prepared by treatment of the compound of formula I with a sufficient amount of the desired acid or base to produce the salt in a conventional manner. Free bases and their salts differ in certain physical properties, such as solubility, but they are equivalent for the purposes of the invention.

The compounds of the present invention can exist in unsolvated as well as solvated forms, including hydrated forms. In general, the solvated forms, with pharmaceutically acceptable solvents such as water, ethanol and the like, are equivalent to the unsolvated forms for the purposes of the invention.

Some compounds of the present invention can exist as different diastereoisomers and/or optical isomers. Diastereoisomers can be separated by conventional techniques such as chromatography or fractional crystallization. The optical isomers can be resolved using any of the conventional techniques of optical resolution to give optically pure isomers. Such a resolution can be performed in any chiral synthetic intermediate as well as in the products of general formula I. The optical resolution techniques include separation by chromatography on a chiral phase or formation of a diastereoisomeric pair, resolution and subsequent recovery of the two enantiomers. The optically pure isomers can also be individually obtained using enantiospecific synthesis. The present invention covers both the individual isomers and their mixtures (e.g. racemic mixtures), whether as obtained by synthesis or by physically mixing them up.

The compounds of formula I may be prepared using the methods described below. It will be apparent to those skilled in the art that the precise method used for the preparation of a given compound may vary depending on its chemical structure. Moreover, in some of the processes described below it will be desirable or necessary to protect reactive or labile groups using conventional protecting groups, for example the groups described below. Both the nature of these protecting groups and the procedures for their introduction and removal are well known in the art.

The compounds of general formula I may be obtained by reaction of a compound of general formula II with a compound of general formula III

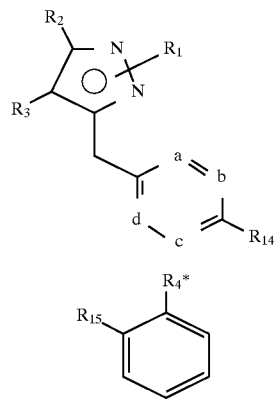

wherein a, b, c, d, $R_1$, $R_2$ and $R_3$ have the previously described meaning, $R_4^*$ represents a group $R_4$ or a group convertible to $R_4$, and one of $R_{14}$ and $R_{15}$ represents a halogen atom, for example bromine or iodine, or a methanesulfonyloxy, toluenesulfonyloxgroup, or trifluoromethanesulfonyloxy group, and the other represents —Sn $(R_{16})_3$, —B(OH)$_2$ or —B(OR$_{17}$)(OR$_{18}$), wherein $R_{16}$ represents a $C_{1-4}$ alkyl group and $R_{17}$ and $R_{18}$ represent each $C_{1-4}$ alkyl or $R_{17}$ and $R_{18}$ together with the oxygen atoms to which they are linked and the boron atom form a 1,3,2-dioxaborane or a 1,3,2-dioxaborolane ring, which may be optionally substituted with $C_{1-4}$ alkyl groups. Examples of substituted rings include 5,5-dimethyl-1,3,2-dioxaborane and 4,4,5,5,-tetramethyl-1,3,2-dioxaborolane.

This reaction can be carried out in the presence of a transition metal catalyst such as tetrakis (triphenylphosphine)palladium (0), palladium acetate and triphenylphosphine or palladium on carbon and triphenylphosphine, and preferably in the presence of a base such as an alkali or alkaline earth metal carbonate, for example sodium carbonate, or in the presence of a fluoride salt, for example cesium fluoride. The reaction is performed in a suitable solvent such as an aromatic hydrocarbon (for example toluene or benzene), an ether (for example dimethoxyethane, diethoxymethane or tetrahydrofuran), water or mixtures thereof, at a suitable temperature, preferably between room temperature and that of the boiling point of the solvent, and during a reaction time preferably between 5 and 48 h. Examples of this kind of couplings have been previously described in Miyaura N., Yanagi T., Suzuki A., Synth. Commun., 1981, 11, 513.

Alternatively, this coupling may be carried out as a one-pot reaction by generating the boronic acid derivative in situ, which avoids the need to isolate it. For example, the compounds of formula I can be obtained by preparing in situ a boronic acid of formula III (i.e. $R_{15}$=—B(OH)$_2$) either from the corresponding bromoderivative by treatment for example with butyl lithium and a trialkylborate or from a compound of formula III wherein $R_{15}$=H via ortho-lithiation optionally in the presence of tetramethylethylene-diamine followed by the addition of the trialkylborate, and then adding an aryl halide of formula II (i.e. $R_{14}$=halogen) and the metal catalyst. Examples of this kind of coupling have been described in Maddaford S. P., Keay B. A., J. Org. Chem., 1994, 59, 6501.

Alternatively, the compounds of formula I may be obtained by a nickel-catalyzed cross-coupling reaction of a compound of formula II with a compound of formula III, wherein $R_{14}$ and $R_{15}$ represent each a halogen atom. This reaction can be carried out in the reported conditions, for example by treatment with a catalytic amount of NiCl$_2$ and triphenylphosphine in the presence of zinc in a suitable solvent such as pyridine.

A compound of formula I may also be obtained by reaction of a compound of formula IV

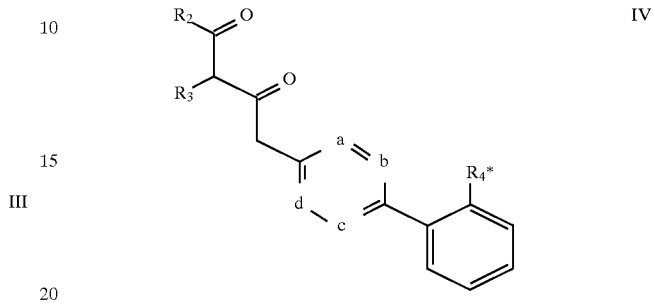

(wherein a, b, c, d, $R_2$ and $R_3$ have the previously described meaning and $R_4^*$ represents a group $R_4$ or a group convertible thereto) with a hydrazine of formula $R_1$NHNH$_2$ (V) in a suitable solvent, preferably a polar solvent such as an alcohol (e.g. ethanol), an ether (e.g. tetrahydrofuran or dioxan) or acetic acid, at a temperature preferably between room temperature and that of the boiling point of the solvent and during a reaction time preferably between 2 and 24 h.

When one or more of the substituents in the starting products of formulae II, III, IV or V are in protected form, it will be necessary a subsequent step for removing said protecting group(s). As protecting groups it is possible to use any of the conventional protecting groups which are widely described in the literature, for example those described in Greene T. W., "Protective Groups in Organic Synthesis", John Wiley & Sons, New York, 1981.

Thus, for instance, as carboxy protecting groups it is possible to use $C_{1-4}$ alkyl esters, such as methyl or tert-butyl, or aryl-$C_{1-4}$ alkyl esters, such as benzyl. As hydroxy protecting groups it is possible to employ silylic ethers, such as tert-butyldimethylsilyl, or aryl$C_{1-4}$ alkyl ethers, such as benzyl. The tetrazolyl group can be protected with, for example, a triphenylmethyl group (i.e. a trityl group), a tert-butyl group or a benzyl group.

Deprotections are carried out following conventional methods. Thus, for example, alkyl esters may be cleaved by hydrolysis in the presence of a base such as an alkali metal hydroxide, for example potassium hydroxide or sodium hydroxide, in a suitable solvent such as an alcohol, for example ethanol, or alcohol-water mixtures, at a temperature between room temperature and that of the boiling point of the solvent and during a period of time preferably between 2 and 24 h; aryl$C_{1-4}$ alkyl groups may be cleaved by hydrogenolysis in the presence of a noble metal catalyst such as palladium on charcoal in a suitable solvent such as an alcohol, for example ethanol, at a temperature between room temperature and that of the boiling point of the solvent, at a pressure between atmospheric pressure and 10 atmospheres and a reaction time preferably between 1 and 48 h; a triphenylmethyltetrazole group can be converted into a tetrazole group by treatment with an acid such as hydrochloric acid or formic acid in a polar solvent such as dichloromethane, tetrahydrofuran or ethanol at a temperature preferably between room temperature and that of the boiling point of the solvent and during a reaction time preferably between 2 and 96 h. A tetrazole group protected with a triphenylmethyl group can also be released simultaneously to the hydrolysis of an ester group under basic conditions, as described above.

In the general processes described above $R_4^*$ has been defined as a group $R_4$ or a group convertible thereto. The conversion of a group $R_4^*$ into a group $R_4$ is carried out in one or a plurality of steps using standard methodology and can be effected at any stage of the synthesis or in the final step. Examples of these conversions include: the conversion of a nitrile group into a tetrazole group by treatment with a suitable azide such as sodium azide, ammonium azide (which may be prepared in situ from sodium azide and ammonium chloride) in a suitable solvent such as a polar solvent, for example dimethylformamide or N-methylpyrrolidone at a suitable temperature, preferably between room temperature and that of the boiling point of the solvent, and during a reaction time between 1 and 96 h, or a trialkyltin azide, for example tributyltin azide (previously prepared or prepared in situ from sodium azide and tributyltin chloride) in an apolar solvent such as an aromatic hydrocarbon, for example xylene or toluene, at a suitable temperature, preferably between room temperature and that of the boiling point of the solvent, and during a reaction time between 1 and 96 h; the hydrolysis of an ester group to give a carboxy group, in the presence of a base such as an alkali metal hydroxide, for example potassium hydroxide or sodium hydroxide, either in a polar solvent such as ethanol or ethanol-water mixtures or in an apolar solvent such as benzene in the presence of a crown ether such as 18-C-6, at a temperature preferably between room temperature and that of the boiling point of the solvent and during a reaction time preferably between 2 and 24 h; the reduction of a nitrile group by treatment with a suitable metal hydride reducing agent such as lithium aluminum hydride in a suitable solvent such as methanol at a temperature preferably between room temperature and that of the boiling point of the solvent and during a reaction time preferably between 1 and 96 h, to give the corresponding amine, and subsequent derivatization of the amine thus obtained by treatment with an acid chloride of formula $R_8COCl$, a sulfonyl chloride of formula $R_9SO_2Cl$ or a sulfonic anhydride of formula $(R_9SO_2)_2O$, wherein $R_8$ and $R_9$ are as described above, in a suitable solvent such as a halogenated hydrocarbon, for example dichloromethane or chloroform; the deprotection of a protected amino group such as a tert-butylamino group under standard conditions such as trifluoroacetic acid in a suitable solvent such as dichloromethane at a temperature between room temperature and that of the boiling point of the solvent to give the free amino group and subsequent reaction thereof with an acid chloride of formula $R_8COCl$, a sulfonyl chloride of formula $R_9SO_2Cl$ or a sulfonic anhydride of formula $(R_9SO_2)_2O$ as described above. All these reactions are known per se and are carried out in accordance with known procedures.

A compound of formula I may also be obtained by interconversion of another compound of formula I in one or a plurality of steps. Thus, for example, a compound of formula I wherein $R_1$ represents hydrogen can be converted into a compound of formula I wherein $R_1$ represents $C_{1-6}$ alkyl or —$(CH_2)_mCOR_5$ by alkylation with the corresponding alkylating agent, such as for example an alkyl halide, preferably an alkyl iodide. The reaction is carried out by heating a compound of formula I and the alkylating agent at a temperature between 60° C. and that of the boiling point of the alkylating agent, or in the presence of a base such as a metal hydride (e.g. sodium hydride), an alkali metal carbonate (e.g. potassium carbonate or cesium carbonate) or a metal hydroxide (e.g. potassium hydroxide) in a suitable solvent, preferably a polar solvent such as a substituted amide, for example dimethylformamide, an ether, for example tetrahydrofuran or dimethoxyethane, or acetone at a temperature preferably between −20° C. and that of the boiling point of the solvent.

Another example of interconversion between compounds of formula I is the halogenation of a compound of formula I wherein $R_2$ represents hydrogen to give a compound of formula I wherein $R_2$ represents halogen. This transformation may be effected by treatment with a halogenating agent such as $X_2$ (wherein X represents a halogen atom) in a suitable solvent such as water or chloroform or with N-bromosuccinimide or N-chlorosuccinimide in a suitable solvent such as a halogenated hydrocarbon, for example carbon tetrachloride or chloroform, at a suitable temperature, preferably between room temperature and that of the boiling point of the solvent. As it will be apparent to those skilled in the art, such an interconversion may also be carried out on any synthetic intermediate of a compound of formula I.

It is also possible to transform a group $R_3$ in a compound of formula I (or in any synthetic intermediate thereof) into another group $R_3$ using standard methods of organic synthesis. For example, an ester can be converted into a carboxy group by hydrolysis by the procedures described above. It is also possible to reduce an ester group by treatment with a metal hydride reducing agent such as lithium aluminum hydride or lithium borohydride in a suitable solvent such as ether, tetrahydrofuran or methanol at a temperature preferably between room temperature and that of the boiling point of the solvent to give the corresponding alcohol. Moreover, a hydroxy group can be oxidized by treatment with a suitable oxidising agent to give an aldehyde. The oxidation of a hydroxy group to an aldehyde can be effected by treatment for example with manganese dioxide in a suitable solvent such as dichloromethane or by treatment with tetra-n-propylammonium perruthenate in the presence of 4-methylmorpholine N-oxide in a suitable solvent such as dichloromethaneacetonitrile mixtures. A hydroxy group can also be converted into a carboxy group by treatment with a stronger oxidising agent such as potassium permanganate or sodium chlorite with sodium dihydrogenphosphate. Furthermore, a carboxy group may be converted into a variety of groups using standard procedures. For example, it can be converted into a carboxamide group of formula —$CONR_{10}R_{11}$ by reaction with an amine of formula $NHR_{10}R_{11}$ in the presence of a condensing agent such as a carbodiimide (for example dicyclohexylcarbodiimide) or carbonyldiimidazole, or alternatively by treatment with 1-hydroxybenzotriazole and a carbodiimide such as dicyclohexylcarbodiimide to form in situ an activated ester and subsequent reaction of said ester with an amine of formula $NHR_{10}R_{11}$ in an inert solvent such as dimethylformamide or dichloromethane. A carboxy group can be readily converted into an ester group following standard procedures; for example, it can be transformed into an ester group of formula —$COOR_{12}$ by treatment with a compound of formula $R_{12}$-L (wherein $R_{12}$ has the previously described meaning and L represents a leaving group such as a halogen atom) in the presence of a base such as potassium carbonate and preferably in the presence of potassium iodide in a suitable solvent such as dimethylformamide. A carboxy group can also be converted to a hydrogen atom by decarboxylation in the presence of an acid such as hydrochloric acid in a suitable solvent such as acetonitrile at a temperature between room temperature and that of the boiling point of the solvent, preferably at the temperature of the boiling point of the solvent. Moreover, a compound of formula I wherein $R_3$ represents carboxy can also be obtained from a compound of formula I wherein $R_3$ is hydrogen by treatment with oxalyl chloride followed by hydrolysis at a temperature between room temperature and that of the boiling point of the solvent and during a reaction time between 2 and 24 h.

Finally, a group $R_4$ in a compound of formula I can also be used to generate other groups $R_4$ by methods known to those skilled in the art, thus giving rise to different compounds of formula I. For example, an ester group can easily be converted into a carboxy group by hydrolysis following the procedures described above. A carboxy group may be converted to a carboxamide group following analogous procedures to those described above in connection with the substituent $R_3$. A carboxy group may also be converted to a group —$CONHSO_2R_9$, wherein $R_9$ has the previously described meaning, by treatment with a sulfonamide of formula $R_9SO_2NH_2$ under the usual conditions known to one skilled in the art. Furthermore, an alkylaminosulfonyl group may be converted to an amino sulfonyl group by hydrolysis and this may be derivatized using standard procedures by treatment for example with an acid chloride of formula $R_8COCl$, a chloroformate derivative of formula $R_9OCOCl$ or a compound of formula $H_2NCOCl$ or $R_8R_9NCOCl$.

As it will be appreciated by those skilled in the art, the interconversion of the substituents as described above can be effected both on the final compounds of formula I or on any synthetic intermediate thereof.

The salts of the compounds of formula I can be prepared by conventional procedures by treatment for example with an acid such as hydrochloric acid, sulfuric acid, nitric acid, oxalic acid or methanesulfonic acid, or by treatment with a base such as sodium hydroxide or potassium hydroxide.

Pyrazoles of general formula II may be obtained following the procedures shown in schemes 1 and 2, below. General procedures for the preparation of pyrazoles are described in Katritzky, A. R. *Handbook of Heterocyclic Chemistry,* Pergamon Press, 1986.

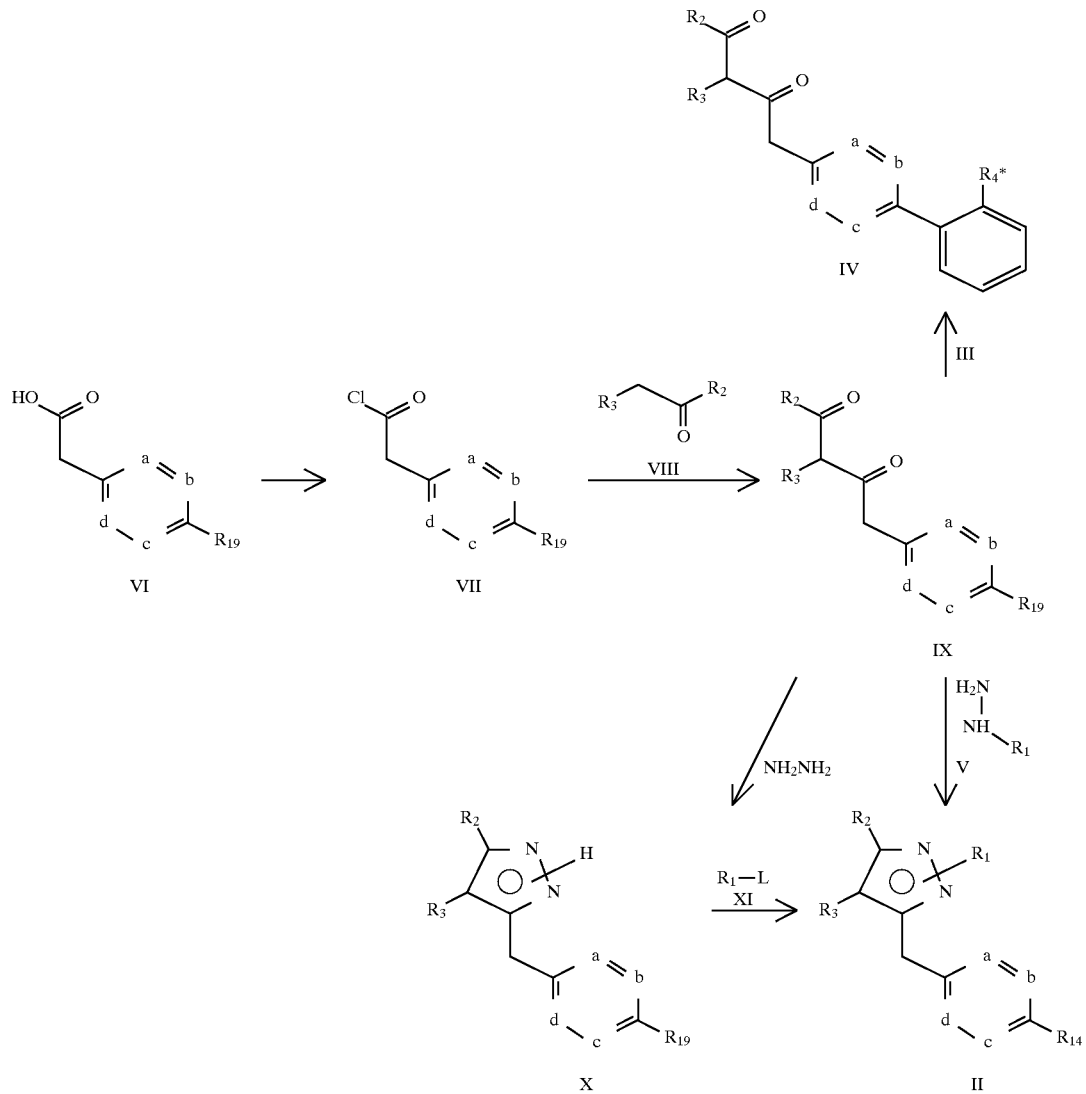

Scheme 1

Scheme 2

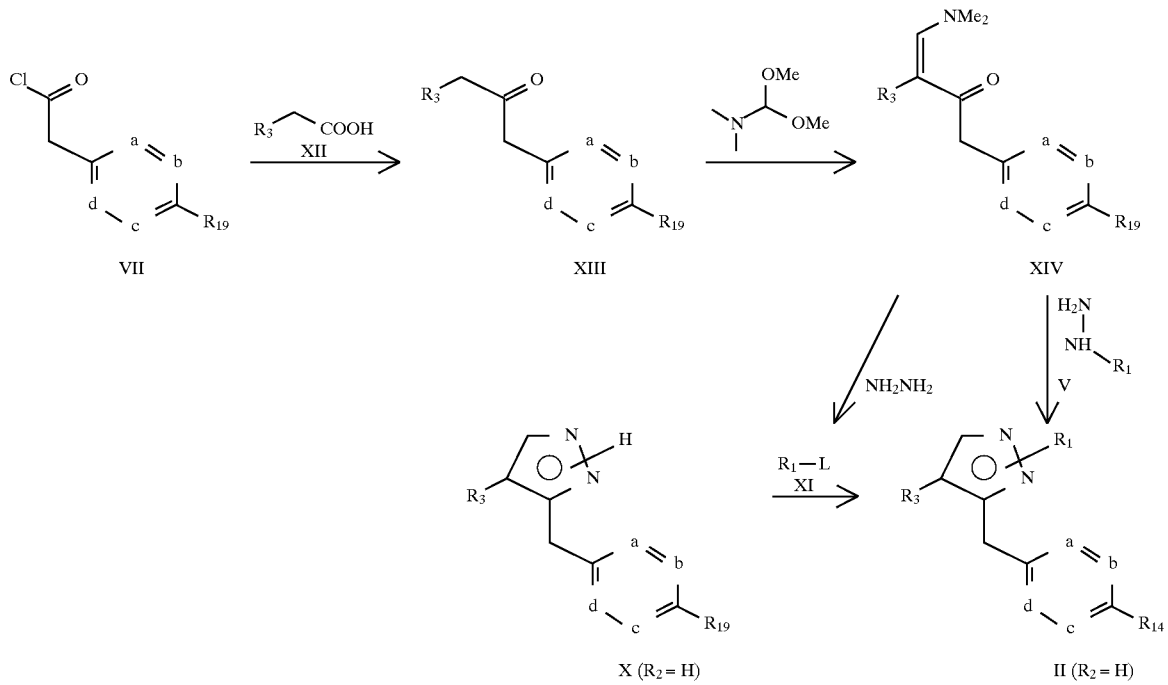

wherein a, b, c, d, $R_1$, $R_2$, $R_3$, $R_4^*$ and $R_{14}$ have the previously described meaning; $R_{19}$ represents halogen, inethanesullfonyloxy, toluenesulfonyloxy, trifluoromethanesulfonyloxy or a group $—B(OR_{17})(OR_{18})$, wherein $R_{17}$ and $R_{18}$ are as described above, and L represents a leaving group.

According to scheme 1, the reaction of a compound of general formula VI with thionyl chloride at a temperature preferably between room temperature and that of the boiling point of the solvent and during a reaction time preferably between 2 and 4 h, leads to the acid chlorides of general formula VII (wherein $R_{19}$ has the previously described meaning).

The reaction of a compound of general formula VII with a compound of general formula VIII in the presence of a base such as an alkali metal (e.g. sodium), a metal hydride (e.g. sodium hydride) or an amidure (e.g. lithium diisopropylamidure) in a suitable solvent such as an apolar solvent, for example benzene or toluene, or an ether, for example tetrahydrofuran or diethyl ether, at a temperature between −78° C. and that of the boiling point of the solvent and during a reaction time preferably between 12 and 48 h, leads to the compounds of general formula IX.

The reaction of a compound of general formula IX with a compound of general formula $R_1NHNH_2$ (V), in a suitable solvent, preferably a polar solvent such as an alcohol (e.g. ethanol), an ether (e.g. tetrahydrofuran or dioxan) or acetic acid, at a suitable temperature preferably between room temperature and that of the boiling point of the solvent and during a reaction time preferably between 2 and 24 h, leads to the compounds of general formula II, wherein $R_{14}$ represents halogen, methanesulfonyloxy, toluenesulfonyloxy, trifluoromethanesulfonyloxy or $—B(OR_{17})(OR_{18})$. The compounds of formula II wherein $R_{14}$ represents $—B(OH)_2$ or $—Sn(R_{16})_3$ can be prepared from the corresponding compound of formula II wherein $R_{14}$ represents halogen by treatment with a suitable boronic acid ester such as triusopropylborate or with trialkyltin chloride, respectively, in the presence of a base such as butyl lithium in a polar solvent such as tetrahydrofuran. Compounds of formula II wherein $R_{14}$ represents $—B(OH)_2$ can also be obtained by hydrolysis of a boronic ester of formula $—B(OR_{17})(OR_{18})$ by conventional procedures. In its turn, compounds of formula II wherein $R_{14}$ represents $—B(OR_{17})(OR_{18})$ may be obtained from their corresponding $—B(OH)_2$ derivatives by treatment with a suitable alcohol such as methanol, ethanol or isopropanol, or a diol such as ethyleneglycol, propanediol or dimethylpropanediol using conventional procedures. Furthermore, compounds of formula II wherein $R_{14}$ represents methanesulfonyloxy, toluenesulfonyloxy or trifluoromethanesulfonyloxy can be prepared from the corresponding halogenated or hydroxy compounds by standard procedures.

The compounds of general formula II can also be obtained by reaction of a compound of general formula X with a compound of general formula $R_1$-L (XI), wherein $R_1$ represents $C_{1-6}$ alkyl or $—(CH_2)_mCOR_5$ and L represents a leaving group such as a halogen atom, in the presence of a base such as a metal hydride (e.g. sodium hydride), an alkali metal carbonate (e.g. potassium carbonate or cesium carbonate) or a metal hydroxide (e.g. potassium hidroxide) in a suitable solvent, preferably a polar solvent such as a substituted amide, for example dimethylformamide, an ether, for example tetrahydrofuran or dimethoxyethane, or acetone at a temperature preferably between −20° C. and that of the boiling point of the solvent during a reaction time preferably between 2 and 24 h. This reaction can also be carried out by heating a compound of formula X and the alkylating agent $R_1$-L in the absence of solvent at a temperature between 60° C. and that of the boiling point of the alkylating agent. The compound of general formula X can be obtained by reaction of IX with hydrazine in the same experimental conditions mentioned above for the reaction of IX with V.

A compound of formula II wherein $R_3$=COOH can also be obtained from the corresponding compound of formula II wherein $R_3$=H following an analogous procedure to that described above for a compound of formula I.

Pyrazoles of formula II wherein $R_2$ represents hydrogen may be prepared by a similar approach, as shown in Scheme 2. The reaction of a compound of formula VII with a compound of formula XII in the presence of a base such as butyl lithium in a suitable solvent such as a polar solvent, for example tetrahydrofuran, leads to a compound of formula XIII. The subsequent reaction of XIII with an equivalent of the aldehyde function such as dimethylformamide dimethyl acetal leads to a compound of formula XIV. Pyrazoles of formula II are then obtained from compounds of formula XIV following the same procedure described above for the preparation of II from compounds of formula IX, i.e. either reaction with a hydrazine derivative of formula V or reaction with hydrazine and subsequent alkylation of the resulting pyrazole with a compound of formula XI.

The compounds of general formula III wherein $R_{15}$ represents halogen are either commercially available, such as for example 2-chlorobenzonitrile, or can be prepared by methods analogous to those described in the literature starting from commercially available products. The compounds of general formula III wherein $R_{15}$ represents methanesulfonyloxy, toluenesulfonyloxy or trifluoromethanesulfonyloxy are prepared from the halogenated or hydroxy compounds by procedures well known in the art. When $R_{15}$ represents —B(OH)$_2$ or —Sn(R$_{16}$)$_3$, the compounds of formula III can be prepared either from the corresponding halogenated compounds following the procedures described above for compounds of formula II or by ortho-lithiation directed by suitable groups, such as 2-triphenylmethyl-2H-tetrazole, N-BOC-amino or tert-butylaminosulfonyl, and subsequent reaction with a trialkylborate such as triisopropylborate or trimethylborate. For example, when $R_4$* represents 2-triphenylmethyl-2H-tetrazole, the boronic acid derivative of formula III can be obtained by reaction of 5-phenyl-2-triphenylmethyl-2H-tetrazole with triisopropylborate, as described in U.S. Pat. No. 5,130,439. When $R_4$* represents N-BOC-amino, the boronic acid derivative III can be obtained by reaction of N-BOC-aniline with trimethylborate as described in Guillier F. et al., *J. Org. Chem.*, 1995, 60, 292. When $R_4$* represents tert-butylaminosulfonyl, the corresponding boronic acid derivative of formula III can be obtained by treatment of N-tert-butyl benzenesulfonamide with butyl lithium and triisopropylborate. When in a compound of formula III $R_{15}$ represents —B(OR$_{17}$)(OR$_{18}$), these compounds can be prepared from the corresponding compounds wherein $R_{15}$=—B(OH)$_2$ as described above.

The compounds of general formula IV can be prepared by reaction of a compound of general formula IX with a compound of general formula III, following an analogous procedure to that described above for the reaction of a compound of formula II with a compound of formula III.

The compounds of formulae V, VI, VIII, XI and XII are either available in the art or, if they have not been previously described, they can be prepared following analogous methods to those described in the literature.

Angiotensin II is a potent arterial vasoconstrictor, and it exerts its action by interacting with specific receptors. The compounds disclosed in the present invention act as antagonists of the angiotensin II receptors. In order to determine their efficacy both in vitro and in vivo, the compounds of the present invention were tested in the following pharmacological tests:

Test 1: Angiotensin II receptor binding assays

The membrane fraction used in this assay was prepared from rat adrenal glands. The tissues were collected in 50 mM Tris-HCl buffer, pH 7.5, so that the concentration was 20% (w/v) and were homogenized at 1000×rpm. The homogenate was centrifuged at 1000 g for 10 min and the supernatant further centrifuged at 100,000 g for 1 h. The resulting membrane pellet was then resuspended in the above buffer at a concentration of 10 mg of protein/mL. Hundred $\mu$L aliquots of the membrane suspension were stored frozen at $-70°$ C. until used.

Aliquots containing 15 $\mu$g of protein were incubated at 25° C. for 1 h in incubation buffer containing (final concentrations): NaCl (120 mM), MgCl$_2$ (5 mM), 0.05% bovine serum albumin, and Tris (50 mM), adjusted to pH 7.5, with or without dithiothreitol (1 mM) to characterize whether drugs preferentially interact with AT$_1$ or AT$_2$ receptor subtypes. Incubation was initiated by the addition of 10 nM $^3$H-Angiotensin II. Total incubation volume was 250 $\mu$L. Nonspecific binding was measured by incubation in the presence of 0.1 $\mu$M Sar$^1$,Ile$^8$-Angiotensin II. Test compounds were studied in the range of concentrations $10^{-10}$M–$10^{-5}$M. Binding was terminated by rapid filtration using a Millipore Multiscreen device. Filters were washed three times with 250 $\mu$L of the corresponding buffer containing or not 1 mM dithiothreitol. Dry filters were placed into vials containing 3 mL of scintillation fluid and the radioactivity counted in a scintillation counter. The IC$_{50}$ value (concentration for 50% displacement of the specifically bound $^3$H-angiotensin II) was determined for each test compound.

A similar binding assay was conducted following the methodology described above but using rat liver instead of rat adrenal glands. The compounds of the present invention were found to have IC$_{50}$ values less than 50 $\mu$M.

Test 2—Inhibition of Angiotensin II-induced pressor response in pithed rats.

Male Sprague-Dawley rats (b.w. 250 g) were anesthetized with sodium pentobarbital (50 mg/Kg, i.p.). The trachea was cannulated and the rats were pithed through the orbit with a stainless steel pithing rod. The rats were immediately placed on a rodent ventilator (volume—1 mL/100 g b.w.; rate—74 strokes/min). The carotid artery was cannulated and connected to a pressure transducer for arterial pressure measurement. A dose-pressor response curve for angiotensin II was obtained administering intravenously and in a cumulative manner doses of AII (0.01–300 $\mu$g/Kg). Then, animals were treated with a dose of the test compound or vehicle 15 minutes before injection of AII. The effective dose of AII required to induce an increase in arterial pressure of 60 mm Hg was calculated for each test compound.

Test 3—Antihvoertensive effects in conscious normotensive rats.

Male Sprague-Dawley rats were surgically) instrumented with a telemetry device for recording blood pressure and heart rate. Signals from the telemetry implants were transmitted to a computer, which received and analyzed the data. After surgery, rats were placed into cages and allowed freedom of movement. Animals were fed with a sodium-depleted diet for ten days and were given furosemide (5 mg/kg/day s.c.) during three days before administration of the test compounds or vehicle. This treatment stimulated renin activity without modifying blood pressure values. Blood pressure and heart rate were monitored for 48 hours and the effects on these parameters due to treatment were compared to those observed in the control group.

Using the methodology described above in tests 2 and 3, representative compounds of the present invention were evaluated in vivo and found to be active at a dose of 50 mg/Kg or much less.

Thus, the compounds of the present invention are useful in the treatment of cardiovascular pathologies where the renin-angiotensin system is involved, such as primary or secondary hypertension, renal vascular hypertension, acute and chronic congestive heart failure, left ventricular hypertrophy, vascular hypertrophy, and diseases related with an elevated intraocular pressure such as glaucoma. Likewise, they can also be of value in the management of other pathologies partly related to the above such as primary and secondary hyperaldosteronism, in the treatment of other disorders of renal ethiology such as diabetic nephropathy, glomerulonephritis, scleroderma, glomerular sclerosis, renal failure, renal transplant therapy, diabetic retinopathy, and in the management of other vascular disorders such as migraine.

The application of the compounds of this invention for these and similar disorders will be apparent to those skilled in the art.

Furthermore, angiotensin II antagonists may also be useful for the treatment of cognitive disorders such as dementia, Alzheimer's disease, amnesia, and learning disorders.

According to the activity of the compounds disclosed, the present invention further provides compositions that comprise a compound of the invention together with an excipient and optionally other auxiliary agents, if necessary. The compounds of the present invention can be administered in different pharmaceutical preparations, the precise nature of which will depend, as it is well known, upon the chosen route of administration and the nature of the pathology to be treated.

Thus, solid compositions according to the present invention for oral administration include compressed tablets, dispersible powders, granules and capsules. In tablets, the active component is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated tablets can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are also possible, wherein the active ingredient is mixed with water or an oily medium, for example peanut oil, liquid paraffin or olive oil.

Dispersible powders and granules suitable for the preparation of a suspension by the addition of water provide the active ingredient in admixture with dispersing or wetting agents, suspending agents, such as sodium carboxymethylcellulose, methylcellulose, hydroxypropylmethylcellulose, sodium alginate, polyvinylpyrrolidone, gum tragacanth, xantham gum, gum acacia, and one or more preservatives, such as methyl or n-propyl-p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavoring, perfuming, preserving agents and buffers.

Other compositions for oral administration include spray compositions, which may be prepared by known methods. The spray compositions will contain a suitable propellent.

Preparations for injection, according to the present invention, for parenteral administration by bonus injection or continuous infusion include sterile aqueous or non-aqueous solutions, suspensions or emulsions, in a non-toxic parentally-acceptable diluent or solvent. Examples of aqueous solvents or suspending media are distilled water for injection, Ringer's solution, and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by any known method or manufactured in the form of sterile solid compositions which can be dissolved in sterile water or some other sterile injectable medium immediately before use. When all of the components are sterile, the injectables will maintain the sterility if they are manufactured in sterile environment.

A compound of the invention may also administered in the form of suppositories for rectal administration of the drug. Such compositions are prepared following conventional procedures, well known to those skilled in the art. For example, they can be prepared by mixing the active ingredient with a conventional suppository base such as cocoa butter or other glycerides.

The compounds of the present invention can also be administered in combination with other antihypertensives and/or diuretics and/or ACE inhibitors and/or calcium channel blockers and/or potassium channel openers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartrate, methylclothiazide, methyldopa, methyldopa hydrochloride, minoxidil, pargyline hydrochloride, polythiazide, prazosin, propanolol, rauwolfia serpentina, rescinnamine, reserpine, sodium nitroprusside, spironolactone, timolol maleate, trichlormethiazide, trimethopan camsylate, benzothiazide, quinethazone, ticrynafan, triamterene, acetazolamide, aminophylline, cyclothiazide, ethacrynic acid, furosemide, procaine, sodium ethacrynate, captopril, delapril hydrochloride, enalapril, enalaprilat, fosinopril sodium, lisinopril, pentopril, quinapril hydrochloride, ramipril, perindopril, teprotide, zofenopril calcium, diflunisal, diltiazem, felodipine, nicardipine, nifedipine, niludipine, nimodipine, nisoldipine, nitrendipine, amlodipine, isradipine, ketanserine, fenoldopam, ibodopamine, verapamil, nicorandil, pinacidil and the like, as well as mixtures and combinations thereof.

When the compounds of this invention are used for the treatment of elevated intraocular pressure, they can be administered in the form of typical pharmaceutical preparations such as the above mentioned or they can be administered in the form of topical ocular formulations, which include solutions, ointments, gels and the like.

The dosage and frequency of dose may vary depending upon symptoms, age and body weight of the patient, as well as upon the route of administration. In general, the compounds of the present invention may be administered for ( example orally to human patients in a daily dose from 0.1 to 500 mg for an adult, preferably a dosage from 2 to 150 mg, which may be administered either as a single dose or as divided doses. However, in particular cases, at the discretion of the attending physician, doses outside the broader range may be required.

The pharmaceutical formulations for topical administration will typically contain about 0.1% to 15% by weight of a compound of formula I. This ocular preparations should contain oftalmologically-acceptable excipients.

Following are some representative preparations for tablets, capsules, syrups and injectables. They can be prepared following standard procedures and they are useful in the treatment of diseases related with the regulation of the renin-angiotensin system such as hypertension, congestive heart failure and elevated intraocular pressure.

| Tablets | |
|---|---|
| Compound of formula I | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |
| Hard gelatin capsules | |
| Compound of formula I | 100 mg |
| Lactose | 197 mg |
| Magnesium stearate | 3 mg |
| | 300 mg |
| Syrup | |
| Compound of formula I | 0.4 g |
| Sucrose | 45 g |
| Flavouring agent | 0.2 g |
| Sweetening agent | 0.1 g |
| Water to | 100 ml |
| Injectable | |
| Compound of formula I | 100 mg |
| Benzylic alcohol | 0.05 ml |
| Propylene glycol | 1 ml |
| Water to | 5 ml |

The following examples illustrate, but do not limit, the scope of the present invention:

REFERENCE EXAMPLE 1

4-Bromophenylacetyl chloride

4-Bromophenylacetic acid (20 g, 0.093 mol) in thionyl chloride (29.46 mL, 0.4 mol) was heated under an argon atmosphere at 60° C. for 2 h. Removal of excess thionyl chloride in vacuo yielded a colourless oil (21.5 g), which was directly used in the next step as obtained.

$^1$H-NMR-(CDCl$_3$) δ (TMS): 4.07 (s, 2H), 7.08 (d, J=8 Hz, 2H), 7.48 (d, J=8 Hz, 2H).

REFERENCE EXAMPLE 2

Methyl 2-(4-bromophenylacetyl)-3-oxopentanoate

Sodium (30% dispersion in toluene, 8.2 mL, 0.094 mol) was placed in a flask under an argon atmosphere. After washing with Et$_2$O, anhydrous Et$_2$O (108 mL) was added and the mixture was cooled to 0° C. A solution of methyl 3-oxopentanoate (11.57 mL, 0.093 mol) in Et$_2$O (65 mL) was added and the resulting white suspension was stirred at room temperature overnight. The reaction mixture was cooled to 0° C. and a solution of the compound obtained in reference example 1 (21.5 g) in anhydrous Et$_2$O (43 mL) was added over 30 min. The solution was stirred at room temperature overnight and then refluxed for 1 h and allowed to cool. A solution of concentrated H$_2$SO$_4$ (6.5 mL) in H$_2$O (65 mL) was added dropwise, the layers were separated and the aqueous phase was extracted with Et$_2$O. The combined organic layers were dried and concentrated. The residue was chromatographed on silica gel (hexane-EtOAc mixtures of increasing polarity) to afford the title compound as a colourless oil (18.03 g, 59%).

$^1$H-NMR-(CDCl$_3$) δ (TMS): 1.13 (t, J=7.2 Hz, 3H), 2.67 (q, J=7.2 Hz, 2H), 3.77 (s, 3H), 3.90 (s, 2H), 7.12 (d, J=8 Hz, 2H), 7.41 (d, J=8 Hz, 2H), 17.65 (s, 1H).

REFERENCE EXAMPLE 3

Methyl 5-(4-bromophenylmethyl)-1-butyl-3-ethyl-1H-pyrazole-4-carboxylate

Methyl 3-(4-bromophenylmethyl)-1-butyl-5-ethyl-1H-pyrazole-4-carboxylate

A solution of the compound obtained in reference example 2 (5 g, 0.015 mol), butylhydrazine oxalate (2.73 g, 0.015 mol) and triethylamine (2.13 mL, 0.015 mol) in EtOH (127 mL) was refluxed for 5 h under an argon atmosphere. The solvent was removed and the resulting residue was dissolved in EtOAc and H$_2$O. The layers were separated and the aqueous phase was extracted with EtOAc. The combined organic layers were dried and concentrated. The residue was chromatographed on silica gel (hexane-EtOAc mixtures of increasing polarity) to afford a 35:65 mixture of the two regioisomners, as a colourless oil (3.8 g, 66%).

$^1$H-NMR-(CDCl$_3$) δ (TMS): 0.7–2.0 (m, 10H), 2.89 (q, J=7.2 Hz, 2H), 3.70 (s, 3H), 3.98 (t, J=8 Hz, 2H), 4.11 (s, 0.65×2H), 4.30 (s, 0.35×2H), 7.0–7.5 (m, 4H).

REFERENCE EXAMPLE 4 a) Methyl 1-butyl-3-ethyl-5-[[2'-(2-triphenylmethyl-2H-tetrazol-5-yl)-1,1'-biphenyl-4-yl]methyl]-1H-pyrazole-4-carboxylate b) Methyl 1-butyl-5-ethyl-3-[[2'-(2-triphenylmethyl-2H-tetrazol-5-yl)-1,1'-biphenyl-4-yl]methyl]-1H-pyrazole-4-carboxylate In a flask under an argon atmosphere were placed the compound obtained in reference example 3 (2 g, 5.3 mmol), 2-(2'-triphenylmethyl-2'-H -tetrazol-5-yl)phenylboronic acid (prepared as described in U.S. Pat. No. 5,130,439) (2.96 g, 6.8 mmol), Na$_2$CO$_3$ (1.03 g, 9.8 mmol), toluene (15.6 mL) and H$_2$O (5 mL). The system was purged and was then refilled with argon (3×). Next, Pd(PPh$_3$)$_4$ (0.16 g, 0.14 mmol) was added and the reaction mixture was heated at 80° C. overnight. The solution was allowed to cool and the two layers were separated. The aqueous phase was extracted with EtOAc and the combined organic phases were dried and concentrated. The residue was chromatographed on silica gel (hexane-EtOAc mixtures of increasing polarity) to afford:

isomer a), as a foamy solid (0.5 g, 14%).
mp: 55°–60° C.;
$^1$H-NMR-(CDCl$_3$) δ (TMS): 0.7–2.0 (m, 10H), 2.90 (q, J=7.2 Hz, 2H), 3.74 (s, 3H), 3.74 (t, J=8 Hz, 2H), 4.30 (s, 2H), 6.7–8.0 (m, 23H).

isomer b), as a white solid (1.00 g, 28%.).
mp: 112°–114° C.;
¹H-NMR-(CDCl₃) δ (TMS): 0.7–2.0 (m, 10H), 2.92 (q, J=7.2 Hz, 2H), 3.68 (s, 3H), 4.00 (t, J=8 Hz, 2H), 4.12 (s, 2H), 6.7–8.0 (m, 23H).

REFERENCE EXAMPLE 5

Methyl 2-(4-bromophenylacetyl)-3-oxobutanoate

Following the procedure described in reference example 2, but using methyl acetoacetate instead of methyl 3-oxopentanoate, the title compound was obtained as a colourless oil (74%).

¹H-NMR-(CDCl₃) δ (TMS): 2.33 (s, 3H), 3.77 (s, 3H), 3.95 (s, 2H), 7.12 (d, J=8 Hz, 2H), 7.41 (d, J=8 Hz, 2H), 17.70 (s, 1H).

REFERENCE EXAMPLE 6

Methyl 5(3)-(4-bromophenylmethyl)-3(5)-methyl-1H-pyrazole-4-carboxylate

Following the procedure described in reference example 3, but starting from the compound obtained in reference example 5 and using hydrazine instead of butylhydrazine oxalate, the title compound was obtained as a colourless oil (40%).

¹H-NMR-(CDCl₃) δ (TMS): 2.38 (s, 3H), 3.77 (s, 3H), 4.12 (s, 2H), 7.00 (d, J=8 Hz, 2H), 7.30 (d, J=8 Hz, 2H), 11.25 (s, 1H).

REFERENCE EXAMPLE 7

Methyl 5-(4-bromophenylmethyl)-1-butyl-3-methyl-1H-pyrazole-4-carboxylate

Methyl 3-(4-bromophenylmethyl)-1-butyl-5-methyl-1H-pyrazole-4-carboxylate

Following the procedure described in reference example 3, but starting from the compound obtained in reference example 5, the title compound was obtained as a 1:1 mixture of regioisomers, as a yellow oil (54%).

¹H-NMR-(CDCl₃) δ (TMS): 0.7–2.0 (m, 7H), 2.45 (s, 0.5×3H), 2.47 (s, 0.5×3H), 3.72 (s, 0.5×3H), 3.78 (s, 0.5×3H), 3.93 (t, J=8 Hz, 2H), 4.13 (s, 0.5×2H) 6.9–7.5 (m, 4H).

REFERENCE EXAMPLE 8

Methyl 1-butyl-3-methyl-5-[[2'-(2-triphenylmethyl-2H-tetrazol-5-yl)-1,1'-biphenyl-4-yl]methyl]-1H-pyrazole-4-carboxylate Methyl 1-butyl-5-methyl-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 7, the title compound was obtained as a 1:1 mixture of regioisomers, as a white solid (40%), together with starting material (32%).

¹H-NMR-(CDCl₃) δ (TMS): 0.7–2.0 (m, 7H), 2.47 (s, 3H), 3.68 (s, 0.5×3H), 3.75 (s, 0.5×3H), 4.0 (t, J=8 Hz, 2H), 4.12 (s, 0.5×2H), 4.30 (s, 0.5×2H), 6.9–8.0 (m, 23H).

REFERENCE EXAMPLE 9 a) 3-(4-Bromophenylmethyl)-1-butyl-4-hydroxymethyl-5-methyl-1H-pyrazole b) 5-(4-Bromophenylmethyl)-1-butyl-4-hydroxymethyl-3-methyl-1H-pyrazole A solution of the compound obtained in reference example 7 (1.38 g, 3.6 mmol) in anhydrous Et₂O (26 mL) was added dropwise to a solution of LiAlH₄ (0.276 g, 7.3 mmol) in anhydrous Et₂O (40 mL) and the mixture was stirred at room temperature under an argon atmosphere for 2 h. The solution was cooled to 0° C. and then treated successively with a mixture of H₂O (0.45 mL) and THF (1 mL), 15% NaOH (0.45 mL) and H₂O (1.25 mL). The mixture was stirred for 10 min, dried and filtered, and the solid was washed several times with EtOAc. Evaporation of the filtrate yielded a residue that was purified by chromatography on silica gel (hexane-EtOAc mixtures of increasing polarity) to give the two regioisomers of the title compound, both as colourless oils (73%).

a) Faster eluting isomer: ¹H-NMR-(CDCl₃) δ (TMS): 0.93 (t, J=6.4 Hz, 3H), 1.1–2.0 (m, 5H), 2.20 (s, 3H), 3.90 (s, 2H), 3.96 (t, J=8 Hz, 2H), 4.30 (s, 2H), 7.05 (d, J=8 Hz, 2H), 7.32 (d, J=8 Hz, 2H).

b) Slower eluting isomer: ¹H-NMR-(CDCl₃) δ (TMS): 0.81 (t, J=6.4 Hz, 3H), 1.1–2.0 (m, 5H), 2.23 (s, 3H), 3.77 (t, J=8 Hz, 2H), 3.95 (s, 2H), 4.43 (s, 2H), 6.97 (d, J=8 Hz, 2H), 7.37 (d, J=8 Hz, 2H).

REFERENCE EXAMPLE 10 a) 1-Butyl-4-hydroxymethyl-5-methyl-3-[[2'-(2-triphenylmethyl-2H-tetrazol-5-yl)-1,1'-biphenyl-4-yl]methyl]-1H-pyrazole b) 1-Butyl-4-hydroxymethyl-3-meth),-5-[[2'-(2-triphenylmethyl-2H-tetrazol-5-yl)-1,1'-biphenyl-4-yl]methyl]-1H-pyrazole Following the procedure described in reference example 4, but starting from isomer a) of the compound obtained in reference example 9, isomer a) of the title compound was obtained (5%).

¹H-NMR-(CDCl₃) δ (TMS): 0.81 (t, J=6.4 Hz, 3H), 1.1–2.0 (m, 5H), 2.20 (s, 3H), 3.79 (t, J=8 Hz, 2H), 3.92 (s, 2H), 4.32 (s, 2H), 6.8–8.0 (m, 23H).

Following the procedure described in reference example 4, but starting from isomer b) of the compound obtained in reference example 9, isomer b) of the title compound was obtained (36%).

¹H-NMR-(CDCl₃) δ (TMS): 0.81 (t, J=6.4 Hz, 3H), 1.1–2.0 (m, 5H), 2.23 (s, 3H), 3.79 (t, J=8 Hz, 2H), 3.92 (s, 2H), 4.42 (s, 2H), 6.8–8.0 (m, 23H).

REFERENCE EXAMPLE 11

Ethyl 2-(4-bromophenylacetyl)-4-methyl-3-oxopentanoate

To a suspension of NaH (7.6 g, 158 mmol) in toluene (142 mL) at 0° C. was added dropwise a solution of ethyl isobutylylacetate (20 g, 126 mmol) in toluene (52 mL) and the resulting solution was stirred under an argon atmosphere for 30 min. Then, a solution of 4-bromophenylacetyl chloride (29.4 g, 126 mmol, prepared as described in reference example 1) in toluene (98 mL) was slowly added and the reaction mixture stirred at room temperature overnight. The resulting solution was poured into H₂O-EtOAc and extracted with H₂O (2×). The organic phase was washed with brine, the aqueous phase was acidified and extracted with EtOAc, and the combined organic phases were dried and concentrated. The residue was chromatographed on silica gel (hexane-EtOAc, 5%) to afford the title compound (29 g, 65%).

¹H-NMR-(CDCl₃) δ (TMS): 1.16 (d, J=6.4 Hz, 6H), 1.31 (t, J=7.2 Hz, 3H), 3.09 (q, J=6.4 Hz, 1H), 3.87 (s, 2H), 4.26

(q, J=7.2 Hz, 2H), 7.12 (d, J=8 Hz, 2H), 7.41 (d, J=8 Hz, 2H), 17.49 (s, 1H).

REFERENCE EXAMPLE 12

Ethyl 5(3)-(4-bromophenylmethyl)-3(5)-isopropyl-1H-pyrazole-4-carboxylate

A mixture of the compound obtained in reference example 11 (46.1 g, 130 mmol), hydrazine monohydrate (9.46 mL, 194 mmol) and acetic acid (437 mL) was stirred at room temperature under an argon atmosphere for 18 h. The resulting solution was poured into $H_2O$-EtOAc and the layers were separated. The aqueous phase was extracted with EtOAc and the combined organic phases were washed with saturated aqueous $NaHCO_3$ solution, dried and concentrated. The residue was recrystallized from hexane to afford the title compound as a yellow solid (38.51 g, 84%).

mp 77°–78° C.;
$^1$H-NMR-($CDCl_3$) δ (TMS): 1.27 (d, J=6.4 Hz, 6H), 1.28 (t, J=7.2 Hz, 3H), 3.62 (q, J=6.4 Hz, 1H), 4.18 (s, 2H), 4.25 (q, J=7.2 Hz, 2H), 7.08 (d, J=8 Hz, 2H), 7.36 (d, J=8 Hz, 2H), 9.17 (s, 1H).

Analysis calculated for $C_{16}H_{19}BrN_2O_2$: C 54.71%; H 5.45%; N 7.98%. Found: C 54.75%; H 5.41%; N 8.00%.

REFERENCE EXAMPLE 13a and b a) Ethyl 5-(4-bromophenylmethyl)-3-isopropyl-1-propyl-1H-pyrazole-4-carboxylate
b) Ethyl 3-(4-bromophenylmethyl)-5-isopropyl-1-propyl-1H-pyrazole-4-carboxylate To a cooled (0° C.) mixture of 55% NaH (3.2 g, 67 mmol) and DMF (148 mL) was added the compound of reference example 12 (17.8 g, 58 mmol) under an argon atmosphere. The mixture w%as stirred for 10 min and propyl iodide (5.9 mL, 58 mmol) was added. The reaction mixture was stirred at room temperature overnight. The solvent was removed, the residue was taken up in EtOAc-$H_2O$ and the aqueous phase was extracted with EtOAc. The combined organic layers were dried and concentrated. The residue was chromatographed on silica gel (hexane-EtOAc mixtures of increasing polarity) to afford the title compound as a 3:1 mixture of regioisomers, which were separated by chromatography on silica gel (hexane-EtOAc mixtures of increasing polarity) to afford:

a) faster eluting isomer as a white solid (54%):
mp 49°–50° C.;
$^1$H-NMR-($CDCl_3$) δ (TMS): 0.80 (t, J=7.2 Hz, 3H), 1.27 (t, J=7.2 Hz, 3H), 1.29 (d, J=6.4 Hz, 6H), 1.72 (m, 2H), 3.54 (q, J=6.4 Hz, 1H), 3.85 (t, J=7.2 Hz, 2H) 4.25 (q, J=7.2 Hz, 2H), 4.31 (s, 2H), 6.97 (d, J=8 Hz, 2H), 7.39 (d, J=8 Hz, 2H).

Analysis calculated for $C_{19}H_{25}BrN_2O_2$: C 58.02%; H 6.41%; N 7.12%. Found: C 58.01%; H 6.45%; N 7.17%.

b) slower eluting isomer as a colourless oil (20%): bp 170° C. (0.1 mm Hg)
$^1$H-NMR-($CDCl_3$) δ (TMS): 0.94 (t, J=7.2 Hz, 3H), 1.24 (t, J=7.2 Hz, 3H), 1.28 (d, J=6.4 Hz, 6H), 1.79 (m, 2H), 3.54 (q, J=6.4 Hz, 1H), 3.95 (t, J=7.2 Hz, 2H), 4.11 (s, 2H), 4.18 (q, J=7.2 Hz, 2H), 6.97 (d, J=8 Hz, 2H), 7.35 (d, J=8 Hz, 2H).

REFERENCE EXAMPLE 14 a) Ethyl 3-isopropyl-1-propyl-5-[[2'-(2-triphenylmethyl-2H-tetrazol-5-yl)-1,1'-biphenyl-4-yl]methyl]-1H-pyrazole-4-carboxylate
b) Ethyl 5-isopropyl-1-propyl-3-[[2'-(2-triphenylmethyl-2H-tetrazol-5-yl)-1,1'-biphenyl-4-yl]methyl]-1H-pyrazole-4-carboxylate Isomer a). Method A: In a flask under argon were placed the compound obtained in reference example 13a (13 g, 33.05 mmol), 2-(2'-triphenylmethyl-2'-H-tetrazol-5-yl) phenylboronic acid (prepared as described in U.S. Pat. No. 5,130,439) (16.16 g, 37.45 mmol), cesium fluoride (11.43 g, 74.87 mmol) and dimethoxyethane (119.6 mL). The system was purged, $Pd(PPh_3)_4$ (2.59 g, 1.13 mmol) was added and then it was purged again. The reaction mixture was heated at 100° C. overnight and then allowed to cool to room temperature and poured into $H_2O$-EtOAc. The two layers were separated and the aqueous phase was extracted with EtOAc. The organic phase was washed with $H_2O$ and brine and the combined organic phases were dried and concentrated. The residue was chromatographed on silica gel (hexane-EtOAc mixtures of increasing polarity) to afford isomer a) of the title compound (17.9 g, 77%).

mp 158°–159° C.;
$^1$H-NMR-($CDCl_3$) δ (TMS): 0.74 (t, J=7.2 Hz, 3H), 1.26 (t, J=7.2 Hz, 3H), 1.30 (d,J=6.4 Hz, 6H), 1.63 (m, 2H), 3.57 (q, J=6.4 Hz, 1H), 3.74 (t, J=7.2 Hz, 3H), 4.23 (q, J=7.2 Hz, 2H), 4.36 (s, 2H), 6.8–7.5 (m, 22H), 7.82 (m, 1H).

Analysis calculated for $C_{45}H_{44}N_6O_2$: C 77.12%; H 6.33%; N 11.99%. Found: C 76.87%; H 6.37%; N 12.00%.

Method B: To a cooled solution (−78° C.) of 5-phenyl-2-triphenylmethyl-2-H-tetrazole (0.39 g, 1 mmol) and tetramethylethylenediamine (0.18 mL, 1.1 mmol) in anhydrous THF (4 mL) was added sec-butyllithium (1.6M in hexanes, 0.29 mL, 1.1 mmol) and the mixture was stirred for 20 min under an argon atmosphere. Then, trimethyl borate (0.14 mL, 1.3 mmol) was added and the mixture stirred for 1.5 h at 0° C. The solvent was concentrated and benzene (4 mL), 2M aqueous $Na_2CO_3$ (1 mL), 0.5 g (1.3 mmol) of the compound obtained in reference example 13a and $Pd(PPh_3)_4$ (0.035 g, 3 mol %) were added. The system was purged and refilled with argon and the mixture was stirred in a preheated (110° C.) bath for 6 h. The mixture was allowed to cool to room temperature and poured into $H_2O$-EtOAc. The two layers were separated and the aqueous phase was extracted with EtOAc. The organic phase was washed with $H_2O$ and brine and the combined organic phases were dried and concentrated. The residue was chromatographed on silica gel (hexane-EtOAc mixtures of increasing polarity) to afford isomer a) of the title compound (0.33 g, 47%) together with starting material (28%).

Isomer b). Following the procedure described in method A above, but starting from reference example 13b, isomer b) of the title compound was obtained in 79% yield.

mp 130°–131° C.;
$^1$H-NMR-($CDCl_3$) δ (TMS): 0.95 (t, J=7.2 Hz, 3H), 1.20 (t, J=7.2 Hz, 3H), 1.37 (d, J=6.4 z, 6H), 1.85 (m, 2H), 3.56 (q, J=6.4 Hz, 1H), 4.05 (t, J=7.2 Hz, 3H), 4.12 (s, 2H), 4.15 (q, J=7.2 Hz, 2H), 6.8–7.5 (m, 22H), 7.82 (m, 1H).

Analysis calculated for $C_{45}H_{44}N_6O_2$: C 77.12%; H 6.33%; N 11.99%. Found: C 76.93%; H 6.32%; N 12.16%.

REFERENCE EXAMPLE 15

Ethyl 2-(4-bromophenylacetyl)-3-cyclopropyl-3-oxopropanoate a) Ethyl 3-cyclopropyl-3-oxopropanoate To a cooled (−70° C.) solution of monoethyl malonate (33.97 g, 257.10 mmol) in THF (639 mL) was added n-BuLi (1.6M in hexanes, 319 mL, 514.19 mmol) and the mixture was stirred under an argon atmosphere for 15 min. The resulting solution was cooled to −65° C. and cyclopropanecarbonyl chloride (15.55 g, 148.77 mmol) was added. The reaction mixture was stirred for 1 h and then allowed to warm up to room temperature. Some drops of water were added and THF was removed. The residue was taken up in 1N HCl/Et$_2$O and extracted with Et$_2$O. The organic phase was washed with saturated NaHCO$_3$, dried and concentrated to a residue. This was purified by chromatography on silica gel (hexane-EtOAc mixtures of increasing polarity) to afford the title compound as a yellow oil (14.7 g, 63%).

$^1$H-NMR-(CDCl$_3$) δ (TMS): 1.1 (m, 4H), 1.28 (t, J=7.2 Hz, 3H), 2.04 (m, 1H), 3.55 (s, 2H), 4.21 (q, J=7.2 Hz, 2H).

b) Title compound of the example

Following the procedure described in reference example 2, but using ethyl 3-cyclopropyl-3-oxopropanoate instead of methyl 3-oxopentanoate, the title compound was obtained (51%).

$^1$H-NMR-(CDCl$_3$) δ (TMS): 1.1 (m, 4H), 1.32 (t, J=7.2 Hz, 3H), 2.34 (m, 1H), 3.88 (s, 2H), 4.28 (q, J=7.2 Hz, 2H), 7.12 (d, J=8 Hz, 2H), 7.41 (d, J=8 Hz, 2H), 17.70 (s, 1H).

REFERENCE EXAMPLE 16

Methyl 5(3)-(4-bromophenylmethyl)-3(5)-ethyl-1H-pyrazole-4-carboxylate

Following the procedure described in reference example 12, but starting from the compound obtained in reference example 2, the title compound was obtained as a yellowish solid (74%).

mp 105°–107° C.;

$^1$H-NMR-(CDCl$_3$) δ (TMS): 1.25 (t, J=7.2 Hz, 3H), 2.92 (q, J=7.2 Hz, 2H), 3.79 (s, 3H), 4.19 (s, 2H), 7.10 (d, J=8 Hz, 2H), 7.39 (d, J=8 Hz, 2H), 9.50 (s, 1H).

REFERENCE EXAMPLE 17

Ethyl 5(3)-(4-bromophenylmethyl)-3(5)-cyclopropyl-1H-pyrazole-4-carboxylate

Following the procedure described in reference example 12, but starting from the compound obtained in reference example 15, the title compound was obtained as a white solid (71%).

mp 87°–89° C.;

$^1$H-NMR-(CDCl$_3$) δ (TMS): 0.9 (m, 4H), 1.30 (t, J=7.2 Hz, 3H), 2.50 (m, 1H), 4.17 (s, 2H), 4.28 (q, J=7.2 Hz, 2H), 7.07 (d, J=8 Hz, 2H), 7.38 (d, J=8 Hz, 2H), 7.55 (s,1H).

Analysis calculated for C$_{16}$H$_{17}$BrN$_2$O$_2$: C 53.03%; H 4.91%; N 8.02%. Found: C 54.72%; H 4.94%; N 8.03%.

REFERENCE EXAMPLE 18

Methyl 5-(4-bromophenylmethyl)-3-ethyl-1-propyl-1H-pyrazole-4-carboxylate

Methyl 3-(4-bromophenylmethyl)-5-ethyl-1-propyl-1H-pyrazole-4-carboxylate

Following the procedure described in reference example 13, but starting from the compound obtained in reference example 16, the title compound was obtained as a 1:1 mixture of regioisomers, as a yellowish oil (82%).

$^1$H-NMR-(CDCl$_3$) δ (TMS): 0.81 (t, J=7.2 Hz, 0.5×3H), 0.94 (t, J=7.2 Hz, 0.5×3H), 0.94 (t, J=7.2 Hz, 0.5×3H), 1.18 (t, J=7.2 Hz, 0.5×3H), 1.25 (t, J=7.2 Hz, 0.5×3H), 1.77 (m, 2H), 2.89 (q, J=7.2 Hz, 0.5×2H), 2.92 (q, J=7.2 Hz, 0.5×2H), 3.74 (s, 0.5×3H), 3.78 (s, 0.5×3H), 3.98 (m, 2H), 4.13 (s, 0.5×2H), 4.31 (s, 0.5×2H), 6.96 (d, J=8 Hz, 0.5×2H), 7.11 (d, J=8 Hz, 0.5×2H), 7.36 (d, J=8 Hz, 0.5×2H), 7.39 (d, J=8 Hz, 0.5×2H), 9.50 (s, 1H).

REFERENCE EXAMPLE 19a and b a) Ethyl 5-(4-bromophenylmethyl)-3-cyclopropyl-1-propyl-1H-pyrazole-4-carboxylate b) Ethyl 3-(4-bromophenylmethyl)-5-cyclopropyl-1-propyl-1H-pyrazole-4-carboxylate Following the procedure described in reference example 13, but starting from the compound obtained in reference example 17, the title compound was obtained as a 4:1 mixture of regioisomers. The regioisomers were separated by chromatography on silica gel (hexane-EtOAc mixtures of increasing polarity) to afford the title compounds (84%).

a) faster eluting isomer as a colourless oil: $^1$H-NMR-(CDCl$_3$) δ (TMS): 0.78 (t, J=7.2 Hz, 3H), 0.92 (d, 4H), 1.28 (t, J=7.2 Hz, 3H), 1.65 (m, 2H), 2.50 (m, 1H), 3.79 (t, J=7.2 Hz, 2H), 4.27 (q, J=7.2 Hz, 2H), 4.31 (s, 2H), 6.97 (d, J=8 Hz, 2H), 7.39 (d, J=8 Hz, 2H).

b) slower eluting isomer as a colourless oil: $^1$H-NMR-(CDCl$_3$) δ (TMS): 0.97 (m, 7H), 1.28 (t, J=7.2 Hz, 3H), 1.85 (m, 2H), 3.70 (m, 1H), 3.79 (t, J=7.2 Hz, 2H), 4.13 (s, 2H), 4.21 (q, J=7.2 Hz, 2H), 7.11 (d, J=8 Hz, 2H), 7.35 (d, J=8 Hz, 2H).

REFERENCE EXAMPLE 20a and b a) Ethyl 5-(4-bromophenylmethyl)-3-cyclopropyl-1-ethyl-1H-pyrazole-4-carboxylate b) Ethyl 3-(4-bromophenylmethyl)-5-cyclopropyl-1-ethyl-1H-pyrazole-4-carboxylate Following the procedure described in reference example 13, but starting from the compound obtained in reference example 17 and using ethyl iodide instead of propyl iodide, the title compound was obtained as a 4:1 mixture of regioisomers. The regioisomers were separated by chromatography on silica gel (hexane-EtOAc mixtures of increasing polarity) to afford the title compounds (83%):

a) faster eluting isomer as a colourless oil: $^1$H-NMR-(CDCl$_3$) δ (TMS): 0.92 (d, 4H), 1.18 (t, J=7.2 Hz, 3H), 1.27 (t, J=7.2 Hz, 3H), 2.50 (m, 1H), 3.85 (q, J=7.2 Hz, 2H), 4.26 (q, J=7.2 Hz, 2H), 4.30 (s, 2H), 6.97 (d, J=8 Hz, 2H), 7.39 (d, J=8 Hz, 2H).

b) slower eluting isomer as a colourless oil: $^1$H-NMR-(CDCl$_3$) δ (TMS): $^1$H -NMR-(CDCl$_3$) δ (TMS): 0.9 (m, 4H), 1.28 (t, J=7.2 Hz, 3H), 1.44 (t, J=7.2 Hz, 3H), 3.7 (m, 1H), 4.13 (s, 2H), 4.22 (q, J=7.2 Hz, 2H), 4.25 (q, J=7.2 Hz, 2H), 7.13 (d, J=8 Hz, 2H), 7.36 (d, J=8 Hz, 2H).

REFERENCE EXAMPLE 21a and b a) Methyl 3-ethyl-1-propyl-5-[[2'-(2-triphenylmethyl-2H-tetrazol-5-yl)-1,1'-biphenyl-4-yl]methyl]-1H-pyrazole-4-carboxylate b) Methyl 5-ethyl-1-propyl-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 18, the title compound was obtained as a mixture of regioisomers (45%). The regioisomers were separated by chromatography on silica gel to afford:

a) faster eluting isomer as a white solid: mp 130°–131° C.; $^1$H-NMR-(CDCl$_3$) δ (TMS): 0.75 (t, J=7.2 Hz, 3H), 1.27 (t, J=7.2 Hz, 3H), 1.61 (q, J=7.2 Hz, 2H), 2.87 (q, J=7.2 Hz, 2H), 3.69 (t, J=7.2 Hz, 2H), 3.74 (s, 3H), 4.30 (s, 2H), 6.8–7.5 (m, 22H), 7.82 (m 1H).

Analysis calculated for C$_{43}$H$_{40}$N$_6$O$_2$: C 76.76%; H 5.99%; N 12.49%. Found: C 76.81%; H 6.09%; N 12.39%.

b) slower eluting isomer as a white solid: mp 139° C.; $^1$H-NMR-(CDCl$_3$) δ (TMS): 0.93 (t, J=7.2 Hz, 3H), 1.18 (t, J=7.2 Hz, 3H), 1.87 (q, J=7.2 Hz, 2H), 2.92 (q, J=7.2 Hz, 2H), 3.68 (s, 3H), 3.97 (t, J=7.2 Hz, 2H), 4.12 (s, 2H), 6.8–7.5 (m, 22H), 7.82 (m 1H).

Analysis calculated for C$_{43}$H$_{40}$N$_6$O$_2$: C 76.76%; H 5.99%; N 12.19%. Found: C 76.77%; H 6.15%; N 12.79%.

REFERENCE EXAMPLE 22

Ethyl 3-cyclopropyl-1-propyl-5-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 19a, the title compound was obtained (35%).

mp 154°–159° C.;

$^1$H-NMR-(CDCl$_3$) δ (TMS): 0.72 (t, J=7.2 Hz, 3H), 0.92 (d, 4H), 1.25 (t, J=7.2 Hz, 3H), 1.60 (m, 2H), 2.50 (m, 1H), 3.67 (t, J=7.2 Hz, 2H), 4.25 (q, J=7.2 Hz, 2H), 4.29 (s, 2H), 6.8–7.5 (m, 22H), 7.82 (m, 1H).

Analysis calculated for C$_{44}$H$_{42}$N$_6$O$_2$: C 76.94%; H 6.16%; N 12.24%. Found: C 77.17%; H 6.08%; N 12.15%.

REFERENCE EXAMPLE 23

Ethyl 3-cyclopropyl-1-ethyl-5-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 20a, the title compound was obtained (44%).

mp 164°–168° C.;

$^1$H-NMR-(CDCl$_3$) δ (TMS): 0.92 (d, 4H), 1.10 (t, J=7.2 Hz, 3H), 1.24 (t, J=7.2 Hz, 3H), 2.50 (m, 1H), 3.75 (q, J=7.2 Hz, 2H), 4.25 (q, J=7.2 Hz, 2H), 4.27 (s, 2H), 6.8–7.5 (m, 22H), 7.82 (m, 1H).

REFERENCE EXAMPLE 24

Ethyl 5-(4-bromophenylmethyl)-1-butyl-3-isopropyl-1H-pyrazole-4-carboxylate

Ethyl 3-(4-bromophenylmethyl)-1-butyl-5-isopropyl-1H-pyrazole-4-carboxylate

Following the procedure described in reference example 3, but starting from the compound obtained in reference example 11, the title compound was obtained as a mixture of regioisomers (30%).

$^1$H-NMR-(CDCl$_3$) δ (TMS): 0.9–1.6 (complex s., 16H), 3.5 (m, 1H), 3.8–4.4 (complex s., 6H), 6.9–7.5 (m, 4H).

REFERENCE EXAMPLE 25a and b a) Ethyl 1-butyl-3-isopropyl-5-[[2'-(2-triphenylmethyl-2H-tetrazol-5-yl)-1,1'-biphenyl-4-yl]methyl]-1H-pyrazole-4-carboxylate b) Ethyl 1-butyl-5-isopropyl-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 24, the title compound was obtained as a 65:35 mixture of regioisomers. The regioisomers were separated by chromatography on silica gel to afford:

a) faster eluting isomer as a foam: $^1$H-NMR-(CDCl$_3$) δ (TMS): 0.9–1.6 (complex s., 16H), 3.5 (m, 1H), 3.8–4.4 (complex s., 6H), 6.8–7.5 (m, 22H), 7.82 (m, 1H).

b) slower eluting isomer as a foam: $^1$H-NMR-(CDCl$_3$) δ (TMS): 0.9–1.6 (complex s., 16H), 3.5 (m, 1H), 3.8–4.4 (complex s., 6H), 6.8–7.5 (m, 22H), 7.82 (m, 1H).

REFERENCE EXAMPLE 26

Ethyl 2-(4-bromophenylacetyl)-3-oxohexanoate

Following the procedure described in reference example 2, but using ethyl 3-oxohexanoate instead of methyl 3-oxopentanoate, the title compound was obtained in 43% yield.

$^1$H-NMR-(CDCl$_3$) δ (TMS): 0.94 (t, J=7.9 Hz, 3H), 1.30 (t, J=7.2 Hz, 3H), 1.60 (m, 2H), 2.59 (t, J=7.2 Hz, 2H), 3.90 (s, 2H), 4.25 (q, J=7.2 Hz, 2H), 7.11 (d, J=8 Hz, 2H), 7.42 (d, J=8 Hz, 2H), 17.48 (s, 1H).

REFERENCE EXAMPLE 27

Ethyl 5-(4-bromophenylmethyl)-1-butyl-3-propyl-1H-pyrazole-4-carboxylate

Ethyl 3-(4-bromophenylmethyl)-1-butyl-5-propyl-1H-pyrazole-4-carboxylate

Following the procedure described in reference example 3, but starting from the compound obtained in reference example 26, the title compound was obtained as a 3:7 mixture of regioisomers (52%).

$^1$H-NMR-(CDCl$_3$) δ (TMS): 0.97 (t, J=7.2 Hz, 3H), 1.26 (t, J=7.2 Hz, 3H), 1.60 (m, 2H), 2.87 (t, J=7.2 Hz, 2H), 4.15 (s, 2H), 4.25 (q, J=7.2 Hz, 2H), 7.11 (d, J=8 Hz, 2H), 7.35 (d, J=8 Hz, 2H), 9.5 (s, 1H).

REFERENCE EXAMPLE 28

Ethyl 1-butyl-3-propyl-5-[[2'-(2-triphenylmethyl-2H-tetrazol-5-yl)-1,1'-biphenyl -4-yl]methyl]-1H-pyrazole-4-carboxylate Ethyl 1-butyl-5-propyl-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 27, the title compound was obtained as a 4:6 mixture of regioisomers (31%).

$^1$H-NMR-(CDCl$_3$) δ (TMS): 0.90–2.0 (m, 8H), 2.87 (t, J=7.2 Hz, 2H), 3.7–4.5 (m, 4H), 76.8–7.5 (m, 22H), 7.85 (m, 1H).

REFERENCE EXAMPLE 29

Ethyl 2-(4-bromophenylacetyl)-3-oxo-3-phenylpropanoate

Following the procedure described in reference example 2, but using ethyl benzoylacetate instead of methyl 3-oxopentanoate, the title compound was obtained in 66% yield.

$^1$H-NMR-(CDCl$_3$) δ (TMS): 1.26 (t, J=7.2 Hz, 3H), 3.95 (s, 2H), 4.25 (q, J=7.2 Hz, 2H), 7.0–8.0 (m, 9H), 17.48 (s, 1H).

REFERENCE EXAMPLE 30

Ethyl 5-(4-bromophenylmethyl)-1-butyl-3-phenyl-1H-pyrazole-4-carboxylate

Ethyl 3-(4-bromophenylmethyl)-1-butyl-5-phenyl-1H-pyrazole-4-carboxylate

Following the procedure described in reference example 3, but starting from the compound obtained in reference example 29, the title compound was obtained as a mixture of regioisomers (48%).

$^1$H-NMR-(CDCl$_3$) δ (TMS): 0.9–2.0 (m,10H), 3.7–4.5 (m, 6H), 7.0–8.0 (m, 9H).

REFERENCE EXAMPLE 31

Ethyl 1-butyl-3-phenyl-5-[[2'-(2-triphenylmethyl-2H-tetrazol-5-yl)-1,1'-biphenyl-4-yl]methyl]-1H-pyrazole-4-carboxylate Ethyl 1-butyl-5-phenyl-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 30, the title compound was obtained as a 1:4 mixture of regioisomers (20%).

$^1$H-NMR-(CDCl$_3$) δ (TMS): 0.9–2.0 (m, 10H), 3.7–4.2 (m, 4H), 4.24 (s, 0.8×2H), 4.37 (s, 0.2×2H), 7.0–8.0 (m, 28H).

REFERENCE EXAMPLE 32

Methyl 5-(4-bromophenylmethyl)-3-methyl-1-(2,2,2-trifluoroethyl)-1H-pyrazole-4-carboxylate Methyl 3-(4-bromophenylmethyl)-5-methyl-1-(2,2,2-trifluoroethyl)-1H-pyrazole-4-carboxylate Following the procedure described in reference example 3, but starting from the compound obtained in reference example 5 and using 2,2,2-trifluoroethylhydrazine instead of butylhydrazine, the title compound was obtained as a 65:35 mixture of regioisomers (18%).

$^1$H-NMR-(CDCl$_3$) δ (TMS): 2.47 (s, 0.65×3H), 2.53 (s, 0.35×3H), 3.76 (s, 0.35×3H), 3.79 (s, 0.65×3H), 4.14 (s, 0.35×2H), 4.38 (s, 0.65×2H), 4.5 (m, 2H), 6.95 (d, J=8 Hz, 0.65×2H), 7.10 (d, J=8 Hz, 0.35×2H), 7.38 (d, J=8 Hz, 0.35×2H), 7.42 (d, J=8 Hz, 0.65×2H).

REFERENCE EXAMPLE 33

Methyl 3-methyl-1-(2,2,2-trifluoroethyl)-5-[[2'-(2-triphenylmethyl-2H-tetrazol-5-yl)-1,1'-biphenyl-4-yl]methyl]-1H-pyrazole-4-carboxylate Methyl 5-methyl-1-(2,2,2-trifluoroethyl)-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 32, the title compound was obtained as a 65:35 mixture of regioisomers (64%).

$^1$H-NMR-(CDCl$_3$) δ (TMS): 2.46 (s, 0.63×3H), 2.49 (s, 0.35×3H), 3.73 (s, 0.35×3H), 3.79 (s, 0.65×3H), 4.13 (S, 0.35×2H), 4.39 (s, 0.65×2H), 4.5 (m, 2H), 6.8–7.5 (m, 22H), 8.0 (m, 1H).

REFERENCE EXAMPLE 34

Methyl 5-(4-bromophenylmethyl)-1-ethyl-3-methyl-1H-pyrazole-4-carboxylate

Methyl 3-(4-bromophenylmethyl)-1-ethyl-5-methyl-1H-pyrazole-4-carboxylate

Following the procedure described in reference example 3, but starting from the compound obtained in reference example 5 and using ethylhydrazine instead of butylhydrazine, the title compound was obtained as a 1.1 mixture of regioisomers (35%).

$^1$H-NMR-(CDCl$_3$) δ (TMS): 1.13 (t, J=7.2 Hz, 0.5×3H), 1.37 (t, J=7.2 Hz, 0.5×3H), 2.46 (s, 3H), 3.72 (s, 0.5×3H), 3.78 (s, 0.5×3H), 3.9 (m, 2H), 4.14 (s, 0.5×2H), 4.32 (s, 0.5×2H), 6.9–7.5 (m, 4H).

REFERENCE EXAMPLE 35

Methyl 1-ethyl-3-methyl-5-[[2'-(2-triphenylmethyl-2H-tetrazol-5-yl)-1,1'-biphenyl-4-yl]methyl]-1H-pyrazole-4-carboxylate Methyl 1-ethyl-5-methyl-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 34, the title compound was obtained as a 1:1 mixture of regioisomers (58%).

$^1$H-NMR-(CDCl$_3$) δ (TMS): 1.12 (t, J=7.2 Hz, 0.5×3H), 1.19 (t, J=7.2 Hz, 0.5×3H), 2.44 (s, 0.5×3H), 2.48 (s, 0.5×3H), 3.68 (s, 0.5×3H), 3.72 (s, 0.5×3H), 3.9 (m, 2H), 4.14 (s, 0.5×2H), 4.35 (s, 0.5×2H), 6.9–7.5 (m, 22W), 7.9 (m, 1H).

REFERENCE EXAMPLE 36

Methyl 5-(4-bromophenylmethyl)-3-methyl-1-phenyl-1H-pyrazole-4-carboxylate

Following the procedure described in reference example 3, but starting from the compound obtained in reference example 5 and using phenylhydrazine instead of butylhydrazine, the title compound was obtained in 35% yield.

$^1$H-NMR-(CDCl$_3$) δ (TMS): 2.53 (s, 3H), 3.88 (s, 3H), 4.29 (s, 2H), 6.9–7.5 (m, 9H).

REFERENCE EXAMPLE 37

Methyl 3-methyl-1-phenyl-5-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 36, the title compound was obtained (55%).

H-NMR-(CDCl$_3$) δ (TMS): 2.62 (s, 3H), 3.83 (s, 3H), 4.34 (s, 2H), 6.9–7.5 (m, 28H).

REFERENCE EXAMPLE 38

Methyl 5-(4-bromophenylmethyl)-1-(ethoxycarbonylmethyl)-3-methyl-1H-pyrazole-4-carboxylate Methyl 3-(4-bromophenylmethyl)-1-(ethoxycarbonylmethyl)-5-methyl-1H-pyrazole-4-carboxylate Following the procedure described in reference example 3, but starting from the compound obtained in reference example 5 and using ethyl hydrazinoacetate hydrochloride instead of butylhydrazine, the title compound was obtained as a 70:30 mixture of regioisomers (15%).

$^1$H-NMR-(CDCl$_3$) δ (TMS); 1.20 (t, J=7.2 Hz, 0.7×3H), 1.28 (t, J=7.2 Hz, 0.3×3H), 2.45 (s, 3H), 3.74 (s, 0.3×3H), 3.79 (s, 0.7×3H), 4.07 (q, J=7.2 Hz, 0.7×3H), 4.17 (q, J=7.2 Hz, 0.7×3H), 4.15 (s, 0.3×2H), 4.31 (s, 0.7×2H), 4.64 (s, 0.7×2H), 4.83 (s, 0.3×2H), 6.97 (d, J=8 Hz, 0.65×2H), 7.10 (d, J=8 Hz, 0.35×2H), 7.38 (d, J=8 Hz, 0.35×2H), 7.42 (d, J=8 Hz, 0.65×2H).

REFERENCE EXAMPLE 39

Methyl 1-(ethoxycarbonylmethyl)-3-methyl-5-[[2'-(2-triphenylmethyl-2H-tetrazol-5-yl)-1,1'-biphenyl-4-yl]methyl]-1H-pyrazole-4-carboxylate Methyl 1-(ethoxycarbonylmethyl)-5-methyl-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 38, the title compound was obtained as a 80:20 mixture of regioisomers (43%).

¹H-NMR-(CDCl₃) δ (TMS): 1.13 (t, J=7.2 Hz, 0.8×3H), 1.17 (t, J=7.2 Hz, 0.2×3H), 2.41 (s, 3H), 3.67 (s, 0.2×3H), 3.75 (s, 0.2×3H), 4.10 (q, J=7.2 Hz, 3H), 4.15 (s, 0.2×2H), 4.31 (s, 0.8×2H), 4.50 (s, 0.8×2H), 4.83 (s, 0.2×2H), 6.9–7.5 (m, 23H).

REFERENCE EXAMPLE 40

Methyl 5-(4-bromophenylmethyl)-3-methyl-1-propyl-1H-pyrazole-4-carboxylate

Methyl 3-(4-bromophenylmethyl)-5-methyl-1-propyl-1H-pyrazole-4-carboxylate

Following the procedure described in reference example 13, but starting from the compound obtained in reference example 6, the title compound was obtained as a 1:1 mixture of regioisomers (4.7 g, 77%).

¹H-NMR-(CDCl₃) δ (TMS): 0.81 (t, J=7.2 Hz, 0.5×3H), 0.92 (t, J=7.2 Hz, 0.5×3H), 1.5 (m, 2H), 2.45 (s, 0.5×3H), 2.48 (s, 0.5×3H), 3.69 (s, 0.5×3H), 3.78 (s, 0.5×3H), 3.93 (t, J=8 Hz, 2H), 4.13 (s, 0.5×2H), 4.32 (s, 0.5×2H), 6.97 (d, J=8 Hz, 0.5×2H), 7.11 (d, J=8 Hz, 0.5×2H), 7.38 (d, J=8 Hz, 0.5×2H), 7.42 (d, J=8 Hz, 0.5×2H).

REFERENCE EXAMPLE 41

Methyl 3-methyl-1-propyl-5-[[2'-(2-triphenylmethyl-2H-tetrazol-5-yl)-1,1'-biphenyl-4-yl]methyl]-1H-pyrazole-4-carboxylate Methyl 5-methyl-1-propyl-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 40, the title compound was obtained as a 55:45 mixture of regioisomers (45%).

¹H-NMR-(CDCl₃) δ (TMS): 0.75 (t, J=7.2 Hz, 0.55×3H), 0.92 (t, J=7.2 Hz, 0.45×3H), 1.7 (m, 2H), 2.47 (s, 0.55×3H), 2.48 (s, 0.45×3H), 3.68 (s, 0.45×3H), 3.79 (s, 0.55×3H), 3.98 (t, J=8 Hz, 2H), 4.12 (s, 0.45×2H), 4.30 (s, 0.55×2H), 6.5–8 (m, 23H).

REFERENCE EXAMPLE 42

Ethyl 2-(4-bromophenylacetyl)-3-oxo-4-phenylbutanoate a) Ethyl 3-oxo-4-phenylbutanoate Following the procedure described in reference example 15a, but using phenylacetyl chloride instead of cyclopropanecarbonyl chloride, the desired product was obtained as a colourless oil in 67% yield.

¹H-NMR-(CDCl₃) δ (TMS): 1.25 (t, J=7.2 Hz, 3H), 3.43 (s, 2H), 3.82 (s, 2H), 4.17 (q, J=7.2 Hz, 2H), 7.28 (m, 5H).

b) Title compound of the example

Following the procedure described in reference example 2, but using ethyl 3-oxo-4-phenylbutanoate instead of methyl 3-oxopentanoate, the title compound was obtained as a colourless oil in 45% yield.

¹H-NMR-(CDCl₃) δ (TMS): 1.29 (t, J=7.2 Hz, 3H), 3.92 (s, 2H), 3.98 (s, 2H), 4.24 (q, J=7.2 Hz, 2H), 7.28 (m, 9H), 17.45 (s, 1H).

REFERENCE EXAMPLE 43

Ethyl 3(5)-benzyl-5(3)-(4-bromophenylmethyl)-1H-pyrazole-4-carboxylate

Following the procedure described in reference example 12, but starting from the compound obtained in reference example 42, the title compound was obtained as a white solid (69%).

mp 114° C.;

¹H-NMR-(CDCl₃) δ (TMS): 1.24 (t, J=7.2 Hz, 3H), 4.15 (s, 2H), 4.28 (s, 2H), 4.24 (q, J=7.2 Hz, 2H), 7.28 (m, 9H), 8.5 (broad s, 1H).

REFERENCE EXAMPLE 44

Ethyl 3-benzyl-5-(4-bromophenylmethyl)-1-propyl-1H-pyrazole-4-carboxylate

Ethyl 5-benzyl-3-(4-bromophenylmethyl)-1-propyl-1H-pyrazole-4-carboxylate

Following the procedure described in reference example 13, but starting from the compound obtained in reference example 43, the title compound was obtained as a 1:1 mixture of regioisomers (70%).

¹H-NMR-(CDCl₃) δ (TMS): 0.79 (t, J=7.2 Hz, 0.5×3H), 0.81 (t, J=7.2 Hz, 0.5×3H), 1.17 (t, J=7.2 Hz, 3H), 1.6 (m, 2H), 3.88 (t, J=7.2 Hz, 0.5×2H), 3.97 (t, J=7.2 Hz, 0.5×2H), 4.14 (s, 0.5×2H), 4.16 (s, 0.5×2H), 4.32 (s, 0.5×2H), 4.38 (s, 0.5×2H), 4.24 (q, J=7.2 Hz, 2H), 6.8–7.5 (m, 9H).

REFERENCE EXAMPLE 45

Ethyl 3-benzyl-1-propyl-5-[[2'-(2-triphenylmethyl-2H-tetrazol-5-yl)-1,1'-biphenyl-4-yl]methyl]-1H-pyrazole-4-carboxylate Ethyl 5-benzyl-1-propyl-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 44, the title compound was obtained as a 1:1 mixture of regioisomers (66%).

¹H-NMR-(CDCl₃) δ (TMS): 0.78 (t, J=7.2 Hz, 0.5×3H), 0.79 (t, J=7.2 Hz, 0.5×3H), 1.14 (t, J=7.2 Hz, 3H), 1.6 (m, 2H), 3.8 (m, 2H), 4.10 (s, 0.5×2H), 4.19 (s, 0.5×2H), 4.31 (s, 0.5×2H), 4.38 (s, 0.5×2H), 4.24 (q, J=7.2 Hz, 2H), 6.8–7.5 (m, 28H).

REFERENCE EXAMPLE 46

Ethyl 2-(4-bromophenylacetyl)acetate

Following the procedure described in reference example 15a, but using the compound obtained in reference example 1 instead of cyclopropanecarbonyl chloride, the title compound was obtained as a colourless oil (76%).

¹H-NMR-(CDCl₃) δ (TMS): 1.23 (t, J=7.2 Hz, 3H), 3.44 (s, 2H), 3.77 (s, 2H), 4.15 (q, J=7.2 Hz, 2H), 7.05 (d, J=8 Hz, 2H), 7.43 (d, J=8 Hz, 2H).

REFERENCE EXAMPLE 47

Ethyl 2-(4-bromophenylacetyl)-2-(N,N-dimethylaminomethylidene)acetate

To the compound obtained in reference example 46 (17.6 g, 62 mmol) was added, at 0° C. under an argon atmosphere, dimethylformamide dimethyl acetal (9.9 mL, 74 mmol) and the mixture was stirred for 10 min. The reaction mixture was then concentrated in vacuo and the residue chromatographed on silica gel (hexane-EtOAc mixtures of increasing polarity) to afford the desired product as a colourless oil (6.00 g, 29%).

¹H-NMR-(CDCl₃) δ (TMS): 1.29 (t, J=7.2 Hz, 3H), 2.94 (s, 6H), 3.98 (s, 2H), 4.21 (q, J=7.2 Hz, 2H), 7.10 (d, J=8 Hz, 2H), 7.38 (d, J=8 Hz, 2H).

REFERENCE EXAMPLE 48 a) Ethyl 5-(4-bromophenylmethyl)-1-butyl-1H-pyrazole-4-carboxylate
b) Ethyl 3-(4-bromophenylmethyl)-1-butyl-1H-pyrazole-4-carboxylate Following the procedure described in reference example 3, but starting from the compound obtained in reference example 47, the title compound was obtained as 9:1 mixture of regioisomers in 49% yield.

$^1$H-NMR-(CDCl$_3$) δ (TMS): 0.8–1.9 (m, 10H), 3.93 (t, J=7.2 Hz, 2H), 4.28 (q, J=7.2 Hz, 2H), 4.37 (s, 2H), 7.00 (d, J=8 Hz, 2H), 7.39 (d, J=8 Hz, 2H), 7.84 (s, 0.1×1H), 7.93 (s, 0.9×1H).

REFERENCE EXAMPLE 49

Ethyl 1-butyl-5-[[2'-(2-triphenylmethyl-2H-tetrazol-5-yl)-1,1'-biphenyl-4-yl]methyl]-1H-pyrazole-4-carboxylate Ethyl 1-butyl-3-[[2'-(2-triphenylmethyl-2H-tetrazol-5-yl)-1,1'-biphenyl-4-yl]methyl]-1H-pyrazole-4-carboxylate Following the procedure described in reference example 4, but starting from the compound obtained in reference example 48, the title compound was obtained as a 9:1 mixture of regioisomers (100%).

$^1$H-NMR-(CDCl$_3$) δ (TMS): 0.8–1.9 (m, 10H), 3.95 (t, J=7.2 Hz, 2H), 4.29 (q, J=7.2 Hz, 2H), 4.39 (s, 2H), 7.0–8.2 (m, 24H).

REFERENCE EXAMPLE 50 a) 3-(4-Bromophenylmethyl)-1-butyl-5-methyl-1H-pyrazole-4-carboxaldehyde
b) 5-(4-Bromophenylmethyl)-1-butyl-3-methyl-1H-pyrazole-4-carboxaldehyde To a solution of the compound obtained in reference example 9a (0.276 g, 0.82 mmol) in CH$_2$Cl$_2$ (2.46 mL), under argon, was added MnO2 (0.5 g, 5.74 mmol) and the reaction mixture was heated at 40° C. overnight. More CH$_2$Cl$_2$ was added, the resulting mixture was filtered through celite and the filtrate was concentrated to afford 0.24 g of a crude product. This was purified by chromatography on silica gel (hexane-EtOAc mixtures of increasing polarity) to yield isomer a) of the title compound as a colourless oil (0.154 g, 54%).

$^1$H-NMR-(CDCl$_3$) δ (TMS): 0.95 (t, J=6.4 Hz, 3H), 1.1–2.0 (m, 4H), 2.48 (s, 3H), 4.01 (t, J=8 Hz, 2H), 4.12 (s, 2H), 7.15 (d, J=8 Hz, 2H), 7.39 (d, J=8 Hz, 2H), 9.83 (s, 1H).

Following essentially the same procedure but starting from isomer b) of reference example 9, isomer b) of the title compound was obtained as a colourless oil in 63% yield.

$^1$H-NMR-(CDCl$_3$) δ (TMS): 0.85 (t, J=6.4 Hz, 3H), 1.1–2.0 (m, 4H), 2.47 (s, 3H), 3.86 (t, J=8 Hz, 2H), 4.27 (s, 2H), 6.97 (d, J=8 Hz, 2H), 7.40 (d, J=8 Hz, 2H), 9.93 (s, 1H).

REFERENCE EXAMPLE 51 a) 1-Butyl-5-methyl-3-[[2'-(2-triphenylmethyl-2H-tetrazol-5-yl)-1,1'-biphenyl-4-yl]methyl]-1H-pyrazole-4-carboxaldehyde
b) 1-Butyl-3-methyl-5-[[2'-(2-triphenylmethyl-2H-tetrazol-5-yl)-1,1'-biphenyl-4-yl]methyl]-1H-pyrazole-4-carboxaldehyde Following the procedure described in reference example 4, but starting from isomer a) of reference example 50, isomer a) of the title compound was obtained in 24% yield.

$^1$H-NMR-(CDCl$_3$) δ (TMS): 0.93 (t, J=6.4 Hz, 3H), 1.1–2.0 (m, 4H), 2.47 (s, 3H), 3.99 (t, J=8 Hz, 2H), 4.16 (s, 2H), 6.8–8.0 (m, 23H), 9.81 (s, 1H).

Following essentially the same procedure but starting from isomer b) of reference example 50, isomer b) of the title compound was obtained in 14% yield.

$^1$H-NMR-(CDCl$_3$) δ (TMS): 0.83 (t, J=6.4 Hz, 3H), 1.1–2.0 (m, 4H), 2.49 (s, 3H), 3.79 (t, J=8 Hz, 2H), 4.22 (s, 2H), 6.8–8.0 (m, 23H), 9.93 (s, 1H).

REFERENCE EXAMPLE 52

3-(4-Bromophenylacetyl)-2,4-pentanedione

To a cooled (0° C.) suspension of Na (40% dispersion in parafine, 7.2 g, 125 mmol) in Et$_2$O (158 mL) was added, a solution of 2,4-pentanedione (10.3 mL, 100 mmol) in Et$_2$O (70 mL) and the mixture was stirred at room temperature under an argon atmosphere overnight. The reaction was cooled again to 0° C. and the compound obtained in reference example 1 (23.3 g, 100 mmol) in Et$_2$O (44.2 mL) was added dropwise. The resulting mixture was stirred at room temperature overnight and was then poured into H$_2$O-EtOAc. The aqueous phase was acidified with 1N HCl to pH=3 and extracted with EtOAc. The combined organic extracts were dried and concentrated to a crude product (12.2 g), which was purified by chromatography on silica gel (hexane-EtOAc) to afford the title compound (4.5 g, 15%).

$^1$H-NMR-(CDCl$_3$) δ (TMS): 2.07 (s, 3H), 2.19 (s, 3H), 3.89 (s, 2H), 7.10 (d, J=8 Hz, 2H), 7.42 (d, J=8 Hz, 2H).

REFERENCE EXAMPLE 53

4-Acetyl-5(3)-(4-bromophenylmethyl)-3(5)-methyl-1H-pyrazole

Following the procedure described in reference example 12, but starting from the compound obtained in reference example 52, the title compound was obtained (13%).

$^1$H-NMR-(CDCl$_3$) δ (TMS): 2.37 (s, 3H), 2.51 (s, 3H), 3.83 (s, 1H), 4.19 (s, 2H), 7.09 (d, J=8 Hz, 2H), 7.42 (d, J=8 Hz, 2H).

REFERENCE EXAMPLE 54

4-Acetyl-5-(4-bromophenylmethyl)-1-butyl-3-methyl-1H-pyrazole

4-Acetyl-3-(4-bromophenylmethyl)-1-butyl-5-methyl-1H-pyrazole

Following the procedure described in reference example 13, but starting from the compound obtained in reference example 53 and using butyl iodide instead of propyl iodide, the title compound was obtained as a 1:1 mixture of regioisomers (67%).

$^1$H-NMR-(CDCl$_3$) δ (TMS): 0.7–2.0 (m, 7H), 2.29 (s, 0.5×3H), 2.42 (s, 0.5×3H), 2.51 (s, 3H), 3.87 (t, J=7.2 Hz, 0.5×2H), 3.95 (t, J=7.2 Hz, 0.5×2H), 4.16 (s, 0.5×2H), 4.32 (s, 0.5×2H), 6.96 (d, J=8 Hz, 0.5×2H), 7.08 (d, J=8 Hz, 0.5×2H), 7.47 (d, J=8 Hz, 0.5×2H), 7.48 (d, J=8 Hz, 0.5×2H).

REFERENCE EXAMPLE 55

4-Acetyl-1-butyl-3-methyl-5-[[2'-(2-triphenylmethyl-2H-tetrazol-5-yl)-1,1'-biphenyl-4-yl]methyl]-1H-pyrazole 4-Acetyl-1-butyl-5-methyl-3-[[2'-(2-triphenylmethyl-2H-tetrazol-5-yl)-1,1'-biphenyl-4-yl]methyl]-1H-pyrazole Following the procedure described in reference example 4, but starting from the compound obtained in reference example 54, the title compound was obtained as a 1:1 mixture of regioisomers (46%).

$^1$H-NMR-(CDCl$_3$) δ (TMS): 0.7–2.0 (m, 7H), 2.23 (s, 0.5×3H), 2.41 (s, 0.5×3H), 2.51 (s, 3H), 3.78 (t, J=7.2 Hz, 0.5×2H), 3.96 (t, J=7.2 Hz, 0.5×2H), 4.14 (s,0.5×2H), 4.30 (s, 0.5×2H), 6.9–7.6 (m, 22H), 8.2 (m, 1H).

REFERENCE EXAMPLE 56

2-(Tert-butylaminosulfonyl)phenylboronic acid a) N-(tert-butyl)benzenesulfonamide To a cooled (0° C.) solution of tert-butylamine (42.9 mL, 410.6 mmol) in THF (840 mL) was added dropwise benzenesulfonyl chloride (26.2 mL, 205 mmol) and the reaction mixture was stirred at room temperature under an argon atmosphere for 6 h. The mixture was then filtered and the collected solid washed with THF. The filtrate was concentrated, redissolved in CH$_2$Cl$_2$ and washed with 0.1N HCl and H$_2$O. The organic solution was dried and concentrated to afford the desired product (41.8 g, 95%).

$^1$H-NMR-(CDCl$_3$) δ (TMS): 1.22 (s, 9H), 4.8 (s, 1H), 7.5 (m, 3H), 8.0 (m, 2H).

b) Title compound

To a solution of the compound obtained in reference example 56a (37.3 g, 175 mmol) in THF (298 mL), at −78° C. under an argon atmosphere, was added n-BuLi (1.6M in hexanes, 273.3 mL, 437 mmol). The mixture was allowed to warm to room temperature, while stirring for 4 h, and then it was stirred at that temperature for 30 min more. The reaction was cooled to −60° C., triisopropylborate (60.6 mL, 262.5 mmol) was added and the resulting mixture was stirred at room temperature overnight. 2N HCl (21 mL) was added and the mixture was stirred at room temperature for 30 min. The solvent was removed and the residue taken up in EtOAc and washed with H$_2$O and 1N NaOH. The aqueous phase was made acid with HCl and extracted with EtOAc. The combined organic extracts were dried and concentrated to a crude product, which was purified by recrystallization from Et$_2$O/hexane to yield the title compound as a white solid (28.9 g, 64%).

mp 122°–130° C.;

$^1$H-NMR-(CDCl$_3$) δ (TMS): 1.22 (s, 9H), 4.97 (s, 1H), 5.99 (s, 2H), 7.5 (m, 2H), 8.0 (m, 2H).

REFERENCE EXAMPLE 57

2-(Tert-butoxycarbonylamino)phenylboronic acid

To a cooled (−78° C.) solution of N-BOC aniline (5 g, 25.87 mmol) in THF (111.1 mL) was added tert-butyl lithium (38.9 mL, 66.7 mmol) and the mixture was stirred under an argon atmosphere for E5 min. It was then allowed to warm up to −20° C. and stirred at that temperature for 2 h. Trimethylborate was added (11.94 mL, 105.6 mmol) and the mixture was stirred until it warmed up to room temperature. Then, it was cooled to 0° C. and aqueous 10% HCl was added to pH=6.5. The layers were separated and the aqueous phase was extracted with CH$_2$Cl$_2$. The combined organic extracts were washed with brine, dried and concentrated to a crude product, which was washed with a mixture of EtOAc-hexane (5:95) to give the title compound as a yellow solid (53%).

$^1$H-NMR-(CDCl$_3$) δ (TMS): 1.52 (s, 9H), 6.8–7.8 (m, 7H).

REFERENCE EXAMPLE 58

Ethyl 3-isopropyl-1-propyl-5-[[2'-(tert-butoxycarbonylamino)-1,1'-biphenyl-4-yl]methyl]-1H-pyrazole-4-carboxylate Following the procedure described in reference example 4, but starting from the compound obtained in reference example 13a and using the compound obtained in reference example 57 instead of 2-(2'-triphenylmethyl -2'H-tetrazol-5-yl)phenylboronic acid, the title compound was obtained (28%).

$^1$H-NMR-(CDCl$_3$+CD$_3$OD) δ (TMS): 0.80 (t, J=7.2 Hz, 3H), 1.34 (d, J=6.4 Hz, 6H), 1.45 (s, 9H), 1.2–1.8 (m, 5H), 3.57 (q, J=6.4 Hz, 1H), 3.92 (t, J=7.2 Hz, 3H), 4.29 (q, J=7.2 Hz, 2H), 4.43 (s, 2H), 6.43 (s, 1H), 7.2 (m, 7H), 8.09 (d, J=8 Hz, 1H).

REFERENCE EXAMPLE 59

Ethyl 5-[[2'-amino-1,1'-biphenyl-4-yl]methyl]-3-isopropyl-1-propyl-1H-pyrazole -4-carboxylate A cooled (3° C.) solution of the compound obtained in reference example 58 (0.34 g, 0.67 mmol) in CH$_2$Cl$_2$ (5.5 mL) was treated with trifluoroacetic acid (0.62 mL, 8.1 mmol) and the reaction stirred at room temperature under an argon atmosphere overnight. The volatiles were removed in vacuo and the residue was taken up in CH$_2$Cl$_2$ and washed with aqueous 10% NaHCO$_3$. The organic phase was dried and concentrated to a crude product. Purification by chromatography on silica gel (hexane-EtOAc, 10%) afforded the title compound as a yellow oil (0.202 g, 74%).

$^1$H-NMR-(CDCl$_3$+CD$_3$OD) δ (TMS): 0.81 (t, J=7.2 Hz, 3H), 1.31 (d, J=6.4 Hz, 6H), 1.2–1.8 (m, 5H), 3.57 (q, J=6.4 Hz, 1H), 3.71 (s, 2H), 3.91 (t, J=7.2 Hz, 3H), 4.27 (q, J=7.2 Hz, 2H), 4.41 (s, 2H), 6.8–7.5 (m, 8H).

REFERENCE EXAMPLE 60

(4-Bromo-2-fluorophenyl)acetonitrile

To a solution of 4-bromo-2-fluorobenzylbromide (44.5 g, 166 mmol) in EtOH (118 mL) was added KCN (13.13 g, 182 mmol) and the mixture was stirred at reflux under an argon atmosphere for 18 h. The mixture was allowed to cool and the solvent was concentrated. The residue thus obtained was dissolved in a mixture of EtOAc and H$_2$O and the two phases were separated. The aqueous phase was extracted with EtOAc and the combined organic phases dried and concentrated to a crude product. Purification by chromatography on silica gel (hexane-EtOAc, 10%) afforded the title compound as a reddish oil (30.0 g, 84%).

$^1$H-NMR-(CDCl$_3$) δ (TMS): 3.71 (s 2H), 7.30 (m, 3H).

REFERENCE EXAMPLE 61

4-Bromo-2-fluorophenylacetic acid

To a solution of the compound obtained in reference example 60 (28.0 g, 131 mmol) in EtOH (165 mL) was added KOH (46 g, 710 mmol) in H$_2$O (62 mL) and the mixture was stirred at reflux under an argon atmosphere for 18 h. The mixture was allowed to cool and the solvent was concentrated. The residue thus obtained was dissolved in a mixture of EtOAc and H$_2$O and the two phases were separated. The aqueous phase was extracted with EtOAc and the combined organic phases dried and concentrated to a crude product. Purification by chromatography on silica gel (hexane-EtOAc, 10%) afforded the title compound as a white solid (30.0 g, 98%).

mp 121°–122° C.;

$^1$H-NMR-(CDCl$_3$) δ (TMS): 3.65 (s, 2H), 7.30 (m, 3H), 9.03 (s, 1H).

Analysis calculated for C$_8$H$_6$BrFO$_2$: C 41.23%; H 2.60%. Found: C 41.43%; H 2.59%.

REFERENCE EXAMPLE 62

4-Bromo-2-fluorophenylacetyl chloride

Following the procedure described in reference example 1, but starting from the compound obtained in reference example 61, the title compound was obtained (100%).

$^1$H-NMR-(CDCl$_3$) δ (TMS): 3.75 (s, 2H), 7.30 (m, 3H).

REFERENCE EXAMPLE 63

Ethyl 2-(4-bromo-2-fluorophenylacetyl)-4-methyl-3-oxopentanoate

Following the procedure described in reference example 11, but starting from the compound obtained in reference example 62, the title compound was obtained as a colourless oil (79%).

$^1$H-NMR-(CDCl$_3$) δ (TMS): 1.16 (d, J=6.4 Hz, 6H), 1.42 (t, J=7.2 Hz, 3H), 3.15 (q, J=6.4 Hz, 1H), 3.97 (s, 2H), 4.28 (q, J=7.2 Hz, 2H), 7.1 (m, 3H), 17.42 (s, 1H).

REFERENCE EXAMPLE 64

Ethyl 5(3)-(4-bromo-2-fluorophenylmethyl)-3(5)-isopropyl-1H-pyrazole-4-carboxylate Following the procedure described in reference example 12, but starting from the compound obtained in reference example 63, the title compound was obtained as a white solid (93%).

mp 83°–85° C.;

$^1$H-NMR-(CDCl$_3$) δ (TMS): 1.30 (d, J=6.4 Hz, 6H), 1.29 (t, J=7.2 Hz, 3H), 3.64 (q, J=6.4 Hz, 1H), 4.22 (s, 2H), 4.27 (q, J=7.2 Hz, 2H), 7.1 (m, 4H).

Analysis calculated for C$_{16}$H$_{18}$BrFN$_2$O$_2$: C 52.05%; H 4.91%; N 7.59%. Found: C 52.09%; H 4.92%; N 7.60%.

REFERENCE EXAMPLE 65a and b a) Ethyl 5-(4-bromo-2-fluorophenylmethyl)-3-isopropyl-1-propyl-1H-pyrazole-4-carboxylate
b) Ethyl 3-(4-bromo-2-fluorophenylmethyl)-5-isopropyl-1-propyl-1H-pyrazole-4-carboxylate Following the procedure described in reference example 13, but starting from the compound obtained in reference example 64, the two regioisomers of the title compound were obtained.

a) Faster eluting isomer as a white solid (57%):

mp 48°–51° C.;

$^1$H-NMR-(CDCl$_3$) δ (TMS): 0.83 (t, J=7.2 Hz, 3H), 1.27 (t, J=7.2 Hz, 3H), 1.30 (d, J=6.4 Hz, 6H), 1.72 (m, 2H), 3.54 (q, J=6.4 Hz, 1H), 3.87 (t, J=7.2 Hz, 2H), 4.24 (q, J=7.2 Hz, 2H), 4.30 (s, 2H), 6.5–7.3 (m, 3H).

a) Slower eluting isomer as a colourless oil (28%):

$^1$H-NMR-(CDCl$_3$) δ (TMS): 0.93 (t, J=7.2 Hz, 3H), 1.25 (t, J=7.2 Hz, 3H), 1.39 (d, J=6.4 Hz, 6H), 1.80 (m, 2H), 3.57 (q, J=6.4 Hz, 1H), 3.98 (t, J=7.2 Hz, 4.18 (s, 2H), 4.24 (q, J=7.2 Hz, 2H), 6.5–7.3 (m, 3H).

REFERENCE EXAMPLE 66

Ethyl 3-isopropyl-1-propyl-5-[[2'-(2-triphenylmethyl-2H-tetrazol-5-yl)-2-fluoro-1,1'biphenyl-4-yl]methyl]-1H-pyrazole-4-carboxylate Following the procedure described in method A of reference example 14, but starting from the compound obtained in reference example 65a, the title compound was obtained (95%).

$^1$H-NMR-(CDCl$_3$) δ (TMS): 0.76 (t, J=7.2 Hz, 3H), 1.22 (t, J=7.2 Hz, 3H), 1.30 (d, J=6.4 Hz, 6H), 1.63 (m, 2H), 3.57 (q, J=6.4 Hz, 1H), 3.75 (t, J=7.2 Hz, 2H), 4.21 (q, J=7.2 Hz, 2H), 4.35 (s, 2H), 6.6–7.5 (m, 21H), 7.82 (m, 1H).

REFERENCE EXAMPLE 67

Methyl 2-(4-bromophenylacetyl)-3-tert-butyl-3-oxopropanoate

Following the procedure described in reference example 11, but using methyl 3-tert-butyl-3-oxopropanoate instead of ethyl isobutyrylacetate, the title compound was obtained (63%).

$^1$H-NMR-(CDCl$_3$) δ (TMS): 1.11 (s, 9H), 3.75 (s, 3H), 3.85 (s, 2H), 5.07 (s, 1H), 7.07 (d, J=8 Hz, 2H), 7.44 (d, J=8 Hz, 2H).

REFERENCE EXAMPLE 68

Methyl 5(3)-(4-bromophenylmethyl)-3(5)-tert-butyl-1H-pyrazole-4-carboxylate

Following the procedure described in reference example 12, but starting from the compound obtained in reference example 67, the title compound was obtained as a foam (78%).

$^1$H-NMR-(CDCl$_3$) δ (TMS): 1.43 (s, 9H), 3.75 (s, 3H), 4.14 (s, 2H), 7.07 (d, J=8 Hz, 2H), 7.44 (d, J=8 Hz, 2H), 10.2 (s, 1H).

REFERENCE EXAMPLE 69

Methyl 5-(4-bromophenylmethyl)-3-tert-butyl-1-propyl-1H-pyrazole-4-carboxylate Following the procedure described in reference example 13, but starting from the compound obtained in reference example 68, the title compound was obtained as a white solid (85%).

mp 81° C.;

$^1$H-NMR-(CDCl$_3$) δ (TMS): 0.81 (t, J=7.2 Hz, 3H), 1.41 (s, 9H), 1.68 (m, 2H), 3.73 (s, 3H), 3.82 (t, J=7.2 Hz, 2H), 4.22 (s, 2H), 6.95 (d, J=8 Hz, 2H), 7.39 (d, J=8 Hz, 2H).

Analysis calculated for C$_{20}$H$_{25}$BrN$_2$O$_2$.0.5H$_2$O: C 57.97%; H 6.32%; N 6.76%. Found: C 58.19%; H 6.49%; N 7.16%.

REFERENCE EXAMPLE 70

Methyl 3-tert-butyl-1-propyl-5-[[2'-(2-triphenylmethyl-2H-tetrazol-5-yl)-1,1'-biphenyl-4-yl]methyl]-1H-pyrazole-4-carboxylate Following the procedure described in reference example 14, method A, but starting from the compound obtained in reference example 69, the title compound was obtained as a white solid (75%).

mp 63°–66° C.;

$^1$H-NMR-(CDCl$_3$) δ (TMS): 0.75 (t, J=7.2 Hz, 3H), 1.43 (s, 9H), 1.63 (m, 2H) 3.67 (s, 3H), 3.68 (t, J=7.2 Hz, 2H), 4.21 (s, 2H), 6.8–7.5 (m, 22H), 7.8 (m, 1H).

Analysis calculated for C$_{46}$H$_{46}$N$_6$O$_2$.0.5H$_2$O: C 76.31%; H 6.53%; N 11.59%. Found: C 75.99%; H 6.18%; N 11.61%.

EXAMPLE 1 a) Methyl 1-butyl-3-ethyl-5-[[2'-(1H-tetrazol-5-yl)-1,1'-biphenyl-4-yl]methyl]-1H-pyrazole-4-carboxylate b) Methyl 1-butyl-5-ethyl-3-[[2'-(1H-tetrazol-5-yl)-1,1'-biphenyl-4-yl]methyl]-1H-pyrazole-4-carboxylate A mixture of isomer a) of the product obtained in reference example 4 (0.385 g, 0.56 mmol), EtOH (4.7 mL) and concentrated HCl (0.31 mL) was stirred at room temperature for 2 h. The mixture was then poured into $H_2O-Et_2O$ and the layers were separated. The aqueous phase was extracted with $Et_2O$ and the combined organic phases were dried and concentrated. The residue was chromatographed on silica gel (hexane-EtOAc mixtures of increasing polarity) to afford isomer a) as a white solid (0.19 g, 78%).

mp 182°–184° C.;
$^1$H-NMR-(CDCl$_3$) δ (TMS): 0.7–2.0 (m, 7H), 1.20 (t, J=7.2 Hz, 3H), 2.83 (q, J=7.2 Hz, 2H), 3.78 (s, 3H), 3.89 (t, J=8 Hz, 2H), 4.38 (s, 2H), 7.12 (s, 4H), 7.5 (m, 4H), 8.1 (m, 1H).

Analysis calculated for $C_{25}H_{28}N_6O_2$: C 67.55%; H 6.35%; N 18.90%. Found: C 67.08%; H 6.33%; N 18.66%.

Using a similar procedure, but starting from isomer b) of the product obtained in reference example 4, isomer b) of the title compound was obtained as a white solid (77%).

mp: 51°–58° C.;
$^1$H-NMR-(CDCl$_3$) δ (TMS): 0.7–2.0 (m, 7H), 1.22 (t, J=7.2 Hz, 3H), 2.95 (q, J=7.2 Hz, 2H), 3.80 (s, 3H), 4.02 (t, J=8 Hz, 2H), 4.27 (s, 2H), 7.1–7.7 (m, 8H), 8.3 (m, 1H).

Analysis calculated for $C_{25}H_{28}N_6O_2 \cdot 0.25H_2O$: C 66.89%; H 6.35%; N 18.73%. Found: C 67.04%; H 6.14%; N 18.39%.

EXAMPLE 2 a) 1-Butyl-3-ethyl-5-[[2'-(1H-tetrazol-5-yl)-1,1'-biphenyl-4-yl]methyl]-1H-pyrazole-4-carboxylic acid
b) 1-Butyl-5-ethyl-3-[[2'-(1H-tetrazol-5-yl)-1,1'-biphenyl-4-yl]methyl]-1H-pyrazole-4-carboxylic acid A mixture of isomer a) of the product obtained in example 1 (0.179 g, 0.40 mmol), EtOH (8.9 mL) and KOH (0.2 g, 3.5 mmol) was refluxed for 2 h. The solvent was evaporated and the residue taken up in $H_2O$-EtOAc. The layers were separated and the aqueous phase was extracted with EtOAc. The combined organic phases were dried and concentrated. Recrystallization of the residue from EtOAc-hexane gave isomer a) of the title compound as a white solid (0.107 g, 63%).

mp: 191°–192° C.;
$^1$H-NMR-(CDCl$_3$-CD$_3$OD) δ (TMS): 0.7–2.0 (m, 7H), 1.26 (t, J=7.2 Hz, 3H), 2.90 (q, J=7.2 Hz, 2H), 3.90 (t, J=8 Hz, 2H), 3.97 (s, 2H+MeOH), 4.39 (s, 2H), 7.06 (s, 4H), 7.5 (m, 4H).

Analysis calculated for $C_{24}H_{26}N_6O_2 \cdot 0.25H_2O$: C 66.27%; H 6.14%; N 19.32%. Found: C 66.47%; H 6.10%; N 19.24%.

Using a similar procedure, but starting from isomer b) of the compound obtained in example 1, isomer b) of the title compound was obtained as a white solid (46%).

mp: 191°–195° C.;
$^1$H-NMR-(CDCl$_3$) δ (TMS): 0.7–2.0 (m, 7H), 1.23 (t, J=7.2 Hz, 3H), 2.97 (q, J=7.2 Hz, 2H), 3.97 (s, 2H+MeOH), 4.03 (t, J=8 Hz, 2H), 4.24 (s, 2H), 7.13 (m, 4H), 7.51 (m, 3H), 7.8 (m, 1H).

Analysis calculated for $C_{24}H_{26}N_6O_2 \cdot 0.25H_2O$: C 66.27%; H 6.14%; N 19.32%. Found: C 66.39%; H 6.20%; N 19.44%.

EXAMPLE 3 a) Methyl 1-butyl-3-methyl-5-[[2'-(1H-tetrazol-5-yl)-1,1'-biphenyl-4-yl]methyl]-1H-pyrazole-4-carboxylate
b) Methyl 1-butyl-5-methyl-3-[[2'-(1H-tetrazol-5-yl)-1,1'-biphenyl-4-yl]methyl]-1H-pyrazole-4-carboxylate Following the procedure described in example 1, but starting from the compound obtained in reference example 8, a 1:1 mixture of the regioisomers of the title compound was obtained as a white solid (58%).

$^1$H-NMR-(CDCl$_3$) δ (TMS): 0.7–2.0 (m, 7H), 2.29 (s, 0.5×3H), 2.47 (s, 0.5×3H), 3.74 (s, 3H), 4.04 (t, J=8 Hz, 2H), 4.14 (s, 0.5×2H), 4.31 (s, 0.5×2H), 7.0–8.0 (m, 8H).

A sample was recrystallized from EtOAc to give isomer a) as a white solid:

mp 172°–176° C.;
$^1$H-NMR-(CDCl$_3$) δ (TMS): 0.7–2.0 (m, 7H), 2.37 (s, 3H), 3.78 (s, 3H), 3.87 (t, J=8 Hz, 2H), 4.37 (s, 2H), 7.0–7.6 (m, 8H), 8.2 (m, 1H).

Analysis calculated for $C_{24}H_{26}N_6O_2$: C 66.96%; H 6.09%; N 19.52%. Found: C 67.09%; H 6.44%; N 19.50%.

EXAMPLE 4 a) 1-Butyl-3-methyl-5-[[2'-(1H-tetrazol-5-yl)-1,1'-biphenyl-4-yl]methyl]-1H-pyrazole-4-carboxylic acid
b) 1-Butyl-5-methyl-3-[[2'-(1H-tetrazol-5-yl)-1,1'-biphenyl-4-yl]methyl]-1H-pyrazole-4-carboxylic acid Following the procedure described in example 2, but starting from the compound obtained in example 3, a 1:1 mixture of the regioisomers of the title compound was obtained as a white solid (74%). The two regioisomers were separated by fractional crystallization from EtOAc-Et$_2$O to afford:

a) faster eluting isomer as a white solid:
mp 220°–221° C.;
$^1$H-NMR-(CDCl$_3$) δ (TMS): 0.7–2.0 (m, 7H), 2.40 (s, 3H), 3.87 (t, J=8 Hz, 2H), 4.36 (s, 2H), 7.06 (s, 4H), 7.5 (m, 5H), 7.93 (m, 1H).

Analysis calculated for $C_{23}H_{24}N_6O_2 \cdot H_2O$: C 63.58; H 6.03%; N 19.34%. Found: C 63.58%; H 6.25%; N 18.97%.

b) slower eluting isomer as a white solid: mp 116°–128° C.;
$^1$H-NMR-(CDCl$_3$) δ (TMS): 0.7–2.0 (m, 7H), 2.52 (s, 3H), 4.02 (t, J=8 Hz, 2H), 4.20 (s, 2H), 7.10 (m, 4H), 7.5 (m, 3H), 8.0 (m, 1H), 8.6 (m, 2H).

Analysis calculated for $C_{23}H_{24}N_6O_2 \cdot H_2O$: C 63.58%; H 6.03%; N 19.34%. Found: C 63.46%; H 6.04%; N 19.33%.

EXAMPLE 5 a) 1-Butyl-4-hydroxymethyl-5-methyl-3-[[2'-(1H-tetrazol-5-yl)-1,1'-biphenyl-4-yl]methyl]-1H-pyrazole
b) 1-Butyl-4-hydroxymethyl-3-methyl-5-[[2'-(1H-tetrazol-5-yl)-1,1'-biphenyl-4-yl]methyl]-1H-pyrazole Following the procedure described in example 1, but starting from isomer a) of the compound obtained in reference example 10, isomer a) of the title compound was obtained (20%).

mp 120°–126° C.;
$^1$H-NMR-(CDCl$_3$) δ (TMS): 0.7–1.8 (m, 8H), 2.17 (s, 3H), 3.77 (t, J=8 Hz, 3.95 (s, 2H), 4.16 (s, 2H), 6.8–8.0 (m, 9H).

Analysis calculated for $C_{23}H_{26}N_6O \cdot 0.75Et_2O$: C 68.17%; H 7.33%; N 18.34%. Found: C 68.58%; H 6.92%; N 18.29%.

Following the procedure described in example 1, but starting from isomer b) of the compound obtained in reference example 10, isomer b) of the title compound was obtained (20%).

mp 154°–156° C.;
$^1$H-NMR-(CDCl$_3$) δ (TMS): 0.7–1.8 (m, 8H), 2.15 (s, 3H), 3.76 (t, J=8 Hz, 2H), 3.98 (s, 2H), 4.26 (s, 2H), 6.8–8.0 (m, 9H).

Analysis calculated for $C_{23}H_{26}N_6O \cdot 0.5Et_2O$: C 69.31%; H 7.11%; N 19.11%. Found: C 69.01%; H 7.04%; N 19.46%.

EXAMPLE 6 a) 3-Isopropyl-1-propyl-5-[[2'-(1H-tetrazol-5-yl)-1,1'-biphenyl-4-yl]methyl]-1H-pyrazole-4-carboxylic acid
b) 5-Isopropyl-1-propyl-3-[[2'-(1H-tetrazol-5-yl)-1,1'-biphenyl-4-yl]methyl]-1H-pyrazole-4-carboxylic acid A mixture of the compound obtained in reference example 14a (17.9 g, 25.54 mmol), KOH (13.05 g, 200 mmol), EtOH (572 mL) and $H_2O$ (69 mL) was refluxed for 3 h. The reaction was then allowed to cool to room temperature, a further portion of KOH (3.26 g, 50 mmol) in $H_2O$ (69 mL) was added and the mixture was refluxed overnight. The solvent was evaporated and the residue taken up in $H_2O$-EtOAc. The layers were separated and the aqueous phase was extracted with EtOAc, acidified and extracted again with EtOAc, whereupon a solid precipitated. The solid was filtered off and the combined organic phases were dried and concentrated to a residue. This was chromatographed on silica gel (hexane-EtOAc mixtures of increasing polarity) to afford 2.36 g of the desired product. This product was combined with the first precipitate and they were recrystallized from MeOH-EtOAc to afford isomer a) of the title compound (7.37 g, 67%).

mp 213° C.;

$^1$H-NMR-(CDCl$_3$+CD$_3$OD) δ (TMS): 0.81 (t, J=7.2 Hz, 3H), 1.30 (d, J=6.4 Hz, 6H), 1.63 (m, 2H), 3.57 (q, J=6.4 Hz, 1H), 3.88 (t, J=7.2 Hz, 2H), 4.40 (s, 4H+H$_2$O), 7.07 (s, 4H), 7.6 (m, 4H).

Analysis calculated for $C_{24}H_{26}N_6O_2$: C 66.96%; H 6.09%; N 19.52%. Found: C 66.63%; H 6.10%; N 19.35%.

Following essentially the same procedure, but starting from reference example 14b, isomer b) of the title compound was obtained.

mp 158°–161° C.;

$^1$H-NMR-(CDCl$_3$+CD$_3$OD) δ (TMS): 0.96 (t, J=7.2 Hz, 3H), 1.41 (d, J=6.4 Hz, 6H), 1.85 (m, 2H), 3.60 (q, J=6.4 Hz, 1H), 4.08 (t, J=7.2 Hz, 2H), 4.21 (s, 4H+H$_2$O), 7.03 (d, J=8 Hz, 2H), 7.20 (d, J=8 Hz, 2H), 7.7 (m, 4H).

Analysis calculated for $C_{24}H_{-26}N_6O_2$: C 66.96%; H 6.09%; N 19.52%. Found: C 66.83%; H 6.23%; N 19.25%.

The potassium salt of isomer a) was prepared by treatment with KOH/EtOH and evaporation of the solvent.

mp>300° C.;

Analysis calculated for $C_{24}H_{24}N_6O_2K_2 \cdot 2H_2O$ C 53.14%; H 5.20%; N 15.48%. Found: C 53.71%; H 5.54%; N 15.10%.

EXAMPLE 7

Methyl 3-ethyl-1-propyl-5-[[2'-(1H-tetrazol-5-yl)-1,1'-biphenyl-4-yl]methyl]-1H-pyrazole-4-carboxylate Following the procedure described in example 1, but starting from the compound obtained in reference example 21a, the title compound was obtained as a white solid in 91% yield.

mp 182° C.;

$^1$H-NMR-(CDCl$_3$+CD$_3$OD) δ (TMS): 0.82 (t, J=7.2 Hz, 3H), 1.25 (t, J=7.2 Hz, 3H), 1.68 (q, J=7.2 Hz, 2H), 2.88 (q, J=7.2 Hz, 2H), 3.57 (s, 1H), 3.80 (s, 3H), 3.88 (t, J=7.2 Hz, 2H), 4.36 (s, 2H), 7.07 (s, 4H), 7.6 (m, 4H).

Analysis calculated for $C_{24}H_{26}N_6O_2$: C 66.96%; H 6.09%; N 19.52%. Found: C 66.96%; H 6.19%; N 19.09%.

EXAMPLE 8

Ethyl 3-isopropyl-1-propyl-5-[[2'-(1H-tetrazol-5-yl)-1,1'-biphenyl-4-yl]methyl]-1H-pyrazole-4-carboxylate Method A. Following the procedure described in example 1, but starting from the compound obtained in reference example 14a, the title compound was obtained as a white solid in 91% yield.

mp 147°–148° C.;

$^1$H-NMR-(CDCl$_3$) δ (TMS): 0.84 (t, J=7.2 Hz, 3H), 1.28 (t, J=7.2 Hz, 3H), 1.29 (d, J=6.4 Hz, 6H), 1.63 (m, 2H), 3.52 (q, J=6.4 Hz, 1H), 3.89 (t, J=7.2 Hz, 2H) 4.27 (q, J=7.2 Hz, 2H), 4.40 (s, 2H), 7.16 (s, 5H), 7.5 (m, 3H), 8.2 (m, 1H).

Analysis calculated for $C_{26}H_{30}N_6O_2$: C 68.10%; H 6.59%; N 18.33%. Found: C 68.15%; H 6.59%; N 18.25%.

Method B. a) Ethyl 3-isopropyl-1-propyl-5-[(2'-cyano-1,1'-biphenyl-4-yl)methyl]1H-pyrazole-4-carboxylate. A mixture of the compound obtained in reference example 13a (0.5 g, 1.3 mmol), 2-chlorobenzonitrile (0.18 g, 1.3 mmol), NiCl$_2$ (0.017 g, 0.13 mmol), triphenylphosphine (0.07 g, 0.26 mmol) and pyridine (1.3 mL) was heated at 80° C. under an argon atmosphere. Next, powdered zinc (0.178 g, 2.73 mmol) was added and the mixture was heated at 80° C. for 5 h. It was then allowed to cool, filtered through celite, and washed with toluene. The filtrate was concentrated, taken up in toluene and filtered again, washing with toluene. The new filtrate was washed with 1N HCl, saturated NaHCO$_3$ solution and H$_2$O. The organic phase was dried and concentrated. The aqueous phase was extracted with EtOAc, dried and concentrated. The combined residues were chromatographed on silica gel (hexane-EtOAc mixtures of increasing polarity) to afford the desired product (0.40 g, 74%).

$^1$H-NMR-(CDCl$_3$) δ (TMS): 0.81 (t, J=7.2 Hz, 3H), 1.28 (t, J=7.2 Hz, 3H), 1.29 (d, J=6.4 Hz, 6H), 1.63 (m, 2H), 3.58 (q, J=6.4 Hz, 1H), 3.89 (t, J=7.2 Hz, 2H), 4.27 (q, J=7.2 Hz, 2H), 4.40 (s, 2H), 7.0–7.8 (m, 8H).

b) Title compound of the example: A mixture of the previous compound (8a, Method B) (0.42 g, 1.0 mmol) and N$_3$SnBu$_3$ (1.03 g, 4 mmol) in xylene (2 mL) was heated at reflux under an argon atmosphere for 24 h. The mixture was washed with H$_2$O, dried and concentrated. The crude product was chromatographed on silica gel (hexane-EtOAc mixtures of increasing polarity) to afford the desired product, identical to the one obtained by Method A (0.24 g, 53%).

EXAMPLE 9

Ethyl 3-cyclopropyl-1-propyl-5-[[2'-(1H-tetrazol-5-yl)-1,1'-biphenyl-4-yl]methyl]-1H-pyrazole-4-carboxylate Following the procedure described in example 1, but starting from the compound obtained in reference example 22, the title compound was obtained as a white solid in 86% yield.

mp 148°–149° C.;

$^1$H-NMR-(CDCl$_3$) δ (TMS): 0.82 (t, J=7.9 Hz, 3H), 0.91 (d, 4H), 1.30 (t, J=7.2 Hz, 3H), 1.70 (m, 2H), 2.47 (m, 1H), 3.86 (t, J=7.2 Hz, 2H), 4.28 (q, J=7.2 Hz, 2H), 4.40 (s, 2H), 7.16 (s, 5H), 7.5 (m, 3H), 8.2 (m, 1H).

Analysis calculated for $C_{26}H_{28}N_6O_2$: C 68.40%; H 6.18%; N 18.41%. Found: C 68.28%; H 6.11%; N 18.08%.

EXAMPLE 10

Ethyl 3-cyclopropyl-1-ethyl-5-[[2'-(1H-tetrazol-5-yl)-1,1'-biphenyl-4-yl]methyl]-1H-pyrazole-4-carboxylate Following the procedure described in example 1, but starting from the compound obtained in reference example 23, the title compound was obtained as a white solid in 91% yield.

mp 73°–77° C.;

¹H-NMR-(CDCl₃) δ (TMS): 0.91 (d, 4H), 1.24 (t, J=7.2 Hz, 3H), 1.30 (t, J=7.2 Hz, 3H), 2.50 (m, 1H), 3.95 (q, J=7.2 Hz, 2H), 4.25 (q, J=7.2 Hz, 2H), 4.39 (s, 2H), 7.15 (s, 5H), 7.5 (m, 3H), 8.2 (m, 1H).

EXAMPLE 11

3-Ethyl-1-propyl-5-[[2'-(1H-tetrazol-5-yl)-1,1'-biphenyl-4-yl]methyl]-1H-pyrazole-4-carboxylic acid Following the procedure described in example 2, but starting from the compound obtained in example 7, the title compound was obtained as a white solid in 62% yield.

mp 229° C.;

¹H-NMR-(CDCl₃+CD₃OD) δ (TMS): 0.81 (t, J=7.2 Hz, 3H), 1.26 (t, J=7.2 Hz, 3H), 1.66 (q, J=7.2 Hz, 2H), 2.90 (q, J=7.2 Hz, 2H), 3.89 (t, J=7.2 Hz, 2H), 4.21 (2H+H₂O), 4.40 (s, 2H), 7.08 (s, 4H), 7.6 (m, 4H).

Analysis calculated for $C_{23}H_{24}N_6O_2$: C 66.33%; H 5.81%; N 20.18%. Found: C 65.93%; H 5.80%; N 20.08%.

EXAMPLE 12

3-Cyclopropyl-1-propyl-5-[[2'-(1H-tetrazol-5-yl)-1,1'-biphenyl-4-yl]methyl]-1H-pyrazole-4-carboxylic acid Following the procedure described in example 2, but starting from the compound obtained in example 9, the title compound was obtained as a white solid in 98% yield.

mp 186°–188° C.;

¹H-NMR-(CDCl₃+CD₃OD) δ (TMS): 0.87 (m, 7H), 1.56 (m, 2H), 2.57 (m, 1H), 3.81 (t, J=7.2 Hz, 2H), 4.21 (2H+H₂O), 4.38 (s, 2H), 7.06 (s, 4H), 7.5 (m, 4H).

Analysis calculated for $C_{24}H_{24}N_6O_2.H_2O$ C 64.56%; H 5.87%; N 18.82%. Found: C 64.43%; H 5.66%; N 18.84%.

EXAMPLE 13

3-Cyclopropyl-1-ethyl-5-[[2'-(1H-tetrazol-5-yl)-1,1'-biphenyl-4-yl]methyl]-1H-pyrazole-4-carboxylic acid Following the procedure described in example 2, but starting from the compound obtained in example 10, the title compound was obtained as a white solid in 80% yield.

mp 227°–229° C.;

¹H-NMR-(CDCl₃+CD₃OD) δ (TMS): 0.91 (d, 4H), 1.16 (t, J=7.2 Hz, 3H), 2.50 (m, 1H), 3.95 (q, J=7.2 Hz, 2H), 4.21 (2H+H₂O), 4.37 (s, 2H), 7.05 (s, 4H).

Analysis calculated for $C_{23}H_{22}N_6O_2.0.5H_2O$: C 65.23%; H 5.47%; N 19.83%. Found: C 65.24%; H 5.49%; N 19.43%.

EXAMPLE 14

3-Isopropyl-1-propyl-5-[[2'-(1H-tetrazol-5-yl)-1,1'-biphenyl-4-yl]methyl]-1H-pyrazole-4-carboxamide To a solution of the compound obtained in example 6a (0.3 g, 0.70 mmol) in anhydrous CH₂Cl₂ (2.9 mL) and DMF (0.67 mL) was added dicyclohexylcarbodiimide (0.15 g, 0.73 mmol) and 1-hydroxybenzotriazole (0.103 g, 0.76 mmol) and the mixture was stirred under an argon atmosphere for 30 min. Next, ammonia (30% aqueous solution, 0.07 mL) was added and the reaction mixture was stirred at room temperature for 5 h. Then, further CH₂Cl₂ was added and the insoluble material was filtered off. The organic phase was washed with saturated NaHCO₃ solution and H₂O, dried and concentrated. The residue was chromatographed on silica gel (hexane-EtOAc mixtures of increasing polarity) to afford the title compound as a white solid (0.158 g, 53%).

mp 156°–159° C.;

¹H-NMR-(CDCl₃+CD₃OD) δ (TMS): 0.84 (t, J=7.2 Hz, 3H), 1.33 (d, J=6.4 Hz, 6H), 1.67 (m, 2H), 3.67 (q, J=6.4 Hz, 1H), 3.91 (t, J=7.2 Hz, 2H), 4.29 (s, 5H+H₂O), 7.07 (s, 4H), 7.6 (m, 4H).

Analysis calculated for $C_{24}H_{27}N_7O.H_2O$: C 64.41%; H 6.53%; N 21–91%. Found: C 64.47%; H 6.18%; N 21.52%.

EXAMPLE 15

3-Ethyl-1-propyl-5-[[2'-(1H-tetrazol-5-yl)-1,1'-biphenyl-4-yl]methyl]-1H-pyrazole-4-carboxamide Following the procedure described in example 14, but starting from the compound obtained in example 11, the title compound was obtained as a white solid in 38% yield.

mp 135°–139° C.;

¹H-NMR-(CDCl₃+CD₃OD) δ (TMS): 0.81 (t, J=7.2 Hz, 3H), 1.30 (t, J=7.2 Hz, 3H), 1.66 (q, J=7.2 Hz, 2H), 2.83 (q, J=7.2 Hz, 2H), 3.89 (t, J=7.2 Hz, 2H), 3.90 (3H+H₂O), 4.29 (s, 2H), 7.06 (s, 4H), 7.6 (m, 4H).

Analysis calculated for $C_{23}H_{25}N_7O.0.5H_2O$: C 65.09%; H 6.33%; N 23.08%. Found: C 64.98%; H 5.87%; N 22.26%.

EXAMPLE 16

3-Cyclopropyl-1-propyl-5-[[2'-(1H-tetrazol-5-yl)-1,1'-biphenyl-4-yl]methyl]-1H-pyrazole-4-carboxamide Following the procedure described in example 14, but starting from the compound obtained in example 12, the title compound was obtained as a white solid in 42% yield.

¹H-NMR-(CDCl₃+CD₃OD) δ (TMS): 0.81 (t, J=7.2 Hz, 3H), 1.25 (m, 4H), 1.63 (m, 2H), 2.89 (m, 1H), 3.86 (t, J=7.2 Hz, 2H), 4.41 (s, 2H), 4.50 (3H+H₂O), 7.07 (s, 4H), 7.5 (m, 4H).

Analysis calculated for $C_{24}H_{25}N_7O.0.25H_2O.0.5Et_2O$: C 66.58%; H 6.55%; N 20.90%. Found: C 66.40%; H 6.55%; N 20.94%.

EXAMPLE 17

3-Cyclopropyl-1-ethyl-5-[[2'-(1H-tetrazol-5-yl)-1,1'-biphenyl-4-yl]methyl]-1H-pyrazole-4-carboxamide Following the procedure described in example 14, but starting from the compound obtained in example 13, the title compound was obtained as a foam in 19% yield.

¹H-NMR-(CDCl₃) δ (TMS): 0.91 (d, 4H), 1.26 (t, J=7.2 Hz, 3H), 3.50 (m, 1H), 3.95 (q, J=7.2 Hz, 2H), 4.2 (broad s, 3H), 4.37 (s, 2H), 7.02 (s, 4H), 7.5 (m, 3H), 8.0 (m, 1H).

Analysis calculated for $C_{23}H_{23}N_7O.1.25CH_2Cl_2$: C 56.05%; H 4.96%; N 18.86%. Found: C 55.93%; H 5.21%; N 18.57%.

EXAMPLE 18

1-Butyl-3-methyl-5-[[2'-(1H-tetrazol-5-yl)-1,1'-biphenyl-4-yl]methyl]-1H-pyrazole-4-carboxamide Following the procedure described in example 14, but starting from the compound obtained in example 4a, the title compound was obtained as a white solid in 25% yield.

mp 204°–208° C.;

$^1$H-NMR-(CDCl$_3$+CD$_3$OD) δ (TMS): 0.7–2.0 (m, 7H), 2.45 (s, 3H), 3.5 (m, 5H+CD$_3$OD), 4.32 (s, 2H), 7.06 (s, 4H), 7.3–7.8 (m, 4H).

Analysis calculated for C$_{23}$H$_{25}$ N$_7$O.H$_2$O: C 63.72%; H 6.28%; N 22.62%. Found: C 63.48%; H 6.07%; N 22.08%.

EXAMPLE 19

Ethyl 1-butyl-3-isopropyl-5-[[2'-(1H-tetrazol-5-yl)-1,1'-biphenyl-4-yl]methyl]-1H-pyrazole-4-carboxylate Following the procedure described in example 1, but starting from the compound obtained in reference example 25a, the title compound was obtained in 57% yield.

$^1$H-NMR-(CDCl$_3$) δ (TMS): 0.84 (t, J=7.2 Hz, 3H), 1.25 (d, J=6.4 Hz, 6H), 1.28 (t, J=7.2 Hz, 3H), 1.0–1.6 (m, 4H), 3.52 (m, 1H), 3.84 (t, J=7.2 Hz, 2H), 4.20 (q, J=7.2 Hz, 2H), 4.34 (s, 2H), 7.07 (s, 5H), 7.5 (m, 3H), 8.2 (m, 1H).

EXAMPLE 20

1-Butyl-3-isopropyl-5-[[2'-(1H-tetrazol-5-yl)-1,1'-biphenyl-4-yl]methyl]-1H-pyrazole-4-carboxylic acid Following the procedure described in example 2, but starting from the compound obtained in example 19, the title compound was obtained as a white solid in 61% yield.

mp 103°–108° C.;

$^1$H-NMR-(CDCl$_3$) δ (TMS): 0.84 (t, J=7.2 Hz, 3H), 1.29 (d, J=6.4 Hz, 6H), 1.0–1.6 (m, 4H), 3.5–4.2 (m, 5H), 4.34 (s, 2H), 7.07 (s, 4H), 7.5 (m, 3H), 8.2 (m, 1H).

Analysis calculated for C$_{25}$H$_{28}$N$_6$O$_2$: C 67.55%; H 6.35%; N 18.90%. Found: C 67.42%; H 6.10%; N 18.42%.

EXAMPLE 21

Ethyl 1-butyl-3-propyl-5-[[2'-(1H-tetrazol-5-yl)-1,1'-biphenyl-4-yl]methyl]-1H-pyrazole-4-carboxylate Ethyl 1-butyl-5-propyl-3-[[2'-(1H-tetrazol-5-yl)-1,1'-biphenyl-4-yl]methyl]1-H-pyrazole-4-carboxylate Following the procedure described in example 1, but starting from the compound obtained in reference example 28, the title compound was obtained in 86% yield, as a 1:1 mixture of regioisomers.

$^1$H-NMR-(CDCl$_3$) δ (TMS): 0.90 (t, J=7.2 Hz, 0.5×3H), 0.99 (t, J=7.2 Hz, 0.5×3H), 1.23 (d, J=6.4 Hz, 0.5×6H), 1.31 (d, J=6.4 Hz, 0.5×6H), 1.0–1.8 (m, 4H), 2.77 (m, 2H), 3.5–4.2 (m, 4H), 4.18 (s, 0.5×2H), 4.35 (s, 0.5×2H), 7.0–7.6 (m, 7H), 8.1 (m, 1H), 9.0 (broad s, 1H).

EXAMPLE 22

1-Butyl-3-propyl-5-[[2'-(1H-tetrazol-5-yl)-1,1'-biphenyl-4-yl]methyl]-1H-pyrazole-4-carboxylic acid 1-Butyl-5-propyl-3-[[2'-(1H-tetrazol-5-yl)-1,1'-biphenyl-4-yl]methyl]-1H-pyrazole-4-carboxylic acid Following the procedure described in example 2, but starting from the compound obtained in example 21, the title compound was obtained as a white solid, as a 1:1 mixture of regioisomers (70%).

$^1$H-NMR-(CDCl$_3$ ) δ (TMS): 0.7–2.0 (m, 12H), 2.83 (m, 2H), 3.9 (m, 2H), 4.18 (s, 0.5×2H), 4.35 (s, 0.5×2H), 7.0–7.6 (m, 7H), 8.1 (m, 1H), 9.9 (broad s, 2H).

Analysis calculated for C$_{25}$H$_{28}$N$_6$O$_2$.0.5H$_2$O: C 66.22%; H 6.40%; N 18.54%. Found: C 66.23%; H 6.22%; N 18.10%.

EXAMPLE 23

Ethyl 1-butyl-3-phenyl-5-[[2'-(1H-tetrazol-5-yl)-1,1'-biphenyl-4-yl]methyl]-1H-pyrazole-4-carboxylate Ethyl 1-butyl-5-phenyl-3-[[2'-(1H-tetrazol-5-yl)-1,1'-biphenyl-4-yl]methyl]-4-pyrazole-1H-carboxylate Following the procedure described in example 1, but starting from the compound obtained in reference example 31, the title compound was obtained in quantitative yield, as a 1:1 mixture of regioisomers.

$^1$H-NMR-(CDCl$_3$) δ (TMS): 0.9–2.0 (m, 10H), 3.7–4.2 (m, 4H), 4.22 (s, 0.5×2H), 4.39 (s, 0.5×2H), 7.0–8.0 (m, 14H).

EXAMPLE 24a and b a) 1-Butyl-3-phenyl-5-[[2'-(1H-tetrazol-5-yl)-1,1'-biphenyl-4-yl]methyl]-1H-pyrazole-4-carboxylic acid b) 1-Butyl-5-phenyl-3-[[2'-(1H-tetrazol-5-yl)-1,1'-biphenyl-4-yl]methyl]-1H-pyrazole-4-carboxylic acid Following the procedure described in example 2, but starting from the compound obtained in example 23, the title compound was obtained as a mixture of regioisomers, which were separated by recrystallization from EtOAc/Et$_2$O to afford:

a) faster eluting isomer as a white solid:

$^1$H-NMR-(CDCl$_3$) δ (TMS): 0.88 (t, J=7.2Hz, 3H), 1.2–2.0 (m, 4H), 3.93 (t, J=7.2 Hz, 2H), 4.44 (s, 2H), 7.0–8.0 (m, 15H).

Analysis calculated for C$_{28}$H$_{26}$N$_{26}$O$_2$.0.25H$_2$O: C 69.62%; H 5.53%; N 17.39%. Found: C 69.57%; H 5.79%; N 17.57%.

b) slower eluting isomer as a white solid:

$^1$H-NMR-(CDCl$_3$) δ (TMS): 0.7–2.0 (m, 7H), 3.90 (t, J=7.2 Hz, 2H), 4.31 (s, 2H), 7.0–8.0 (m, 15H).

Analysis calculated for C$_{28}$H$_{26}$N$_6$O$_2$.0.5H$_2$O: C 68.98%; H 5.58%; N 17.23%. Found: C 69.35%; H 5.40%; N 16.95%.

EXAMPLE 25

Methyl 3-methyl-5-[[2'-(1H-tetrazol-5-yl)-1,1'-biphenyl-4-yl]methyl]-1-(2,2,2-trifluoroethyl)-1H-pyrazole-4-carboxylate Methyl 5-methyl-3-[[2'-(1H-tetrazol-5-yl)-1,1'-biphenyl-4-yl]methyl]-1-(2,2,2-trifluoroethyl)-1H-pyrazole-4-carboxylate Following the procedure described in example 1, but starting from the compound obtained in reference example 33, the title compound was obtained as a 65:35 mixture of regioisomers (59%).

$^1$H-NMR-(CDCl$_3$) δ (TMS): 2.40 (s, 3H), 3.78 (s, 3H), 4.41 (s, 2H), 4.50 (q, J=8 Hz, 2H), 7.06 (s, 4H), 7.5 (m, 4H), 7.8 (m, 1H).

EXAMPLE 26

3-Methyl-5-[[2'-(1H-tetrazol-5-yl)-1,1'-biphenyl-4-yl]methyl]-1-(2,2,2-trifluoroethyl)-1H-pyrazole-4-carboxylic acid Following the procedure described in example 2, but starting from the compound obtained in example 25, a 65:35 mixture of regioisomers was obtained (70%), from which the title compound was separated as a white solid by recrystallization from MeOH/Et$_2$O/hexane. mp 236° C.;

$^1$H-NMR-(CDCl$_3$+CD$_3$OD) δ (TMS): 2.48 (s, 3H), 4.31 (s, 2H+H$_2$O), 4.48 (s, 2H), 4.50 (q, J=8 Hz, 2H), 7.06 (s, 4H), 7.5 (m, 4H).

Analysis calculated for C$_{21}$H$_{17}$F$_3$N$_6$O$_2$0.25H$_2$O: C 56.43%; H 3.97%; N 18.80%. Found: C 56.45%; H 3.94%; N 18.52%.

EXAMPLE 27

Methyl 1-ethyl-3-methyl-5-[[2'-(1H-tetrazol-5-yl)-1, 1'-biphenyl-4-yl]methyl]-1H-pyrazole-4-carboxylate Methyl 1-ethyl-5-methyl-3-[[2'-(1H-tetrazol-5-yl)-1, 1'-biphenyl-4-yl]methyl]-1H-pyrazole-4-carboxylate Following the procedure described in example 1, but starting from the compound obtained in reference example 35, the title compound was obtained as a 1:1 mixture of regioisomers (83%).

$^1$H-NMR-(CDCl$_3$) δ (TMS): 1.23 (t, J=7.2 Hz, 0.5×3H), 1.25 (t, J=7.2 Hz, 0.5×3H), 2.37 (s, 0.5×3H), 2.51 (s, 0.5×3H), 3.78 (s, 0.5×3H), 3.80 (s, 0.5×3H), 3.9 (m, 2H), 4.20 (0.5×2H), 4.36 (s, 0.5×2H), 6.9–7.5 (m, 8H), 7.9 (m, 1H).

EXAMPLE 28

1-Ethyl-3-methyl-5-[[2'-(1H-tetrazol-5-yl)-1,1'-biphenyl-4-yl]methyl]-1H-pyrazole-4-carboxylic acid 1-Ethyl-5-methyl-3-[[2'-(1H-tetrazol-5-yl)-1,1'-biphenyl-4-yl]methyl]-1H-pyrazole-4-carboxylic acid Following the procedure described in example 2, but starting from the compound obtained in example 27, the title compound was obtained as a 1:1 mixture of regioisomers as a white solid (80%). mp 200° C.;

$^1$H-NMR-(CDCl$_3$) δ (TMS): 1.34 (t, J=7.2 Hz, 0.5×3H), 1.54 (t, J=7.2 Hz, 0.5×3H), 2.61 (s, 0.5×3H), 2.69 (s, 0.5×3H), 3.9 (m, 2H), 4.13 (s, 2H+H$_2$O), 4.37 (s, 0.5×2H), 4.54 (s, 0.5×2H), 6.9–7.9 (m, 8H).

Analysis calculated for C$_{21}$H$_{20}$N$_6$O$_2$.0.25H$_2$O: C 64.19%; H 5.28%; N 21.38%. Found: C 64.27%; H 5.23%; N 21.53%.

EXAMPLE 29

Methyl 3-methyl-1-phenyl-5-[[2'-(1H-tetrazol-5-yl)-1,1'-biphenyl-4-yl]methyl]-1H-pyrazole-4-carboxylate Following the procedure described in example 1, but starting from the compound obtained in reference example 37, the title compound was obtained as a white solid (55%). mp 190°–194° C.;

$^1$H-NMR-(CDCl$_3$) δ (TMS): 2.50 (s, 3H), 3.82 (s, 3H), 4.38 (s, 2H), 7.01 (s, 4H), 7.5 (m, 9H), 8.1 (m, 1H).

Analysis calculated for C$_{26}$H$_{22}$N$_6$O$_2$.0.25H$_2$O: C 68.63%; H 4.98%; N 18.47%. Found: C 68.58%; H 5.15%; N 18.24%.

EXAMPLE 30

3-Methyl-1-phenyl-5-[[2'-(1H-tetrazol-5-yl)-1,1'-biphenyl-4-yl]methyl]-1H-pyrazole-4-carboxylic acid Following the procedure described in example 2, but starting from the compound obtained in example 29, the title compound was obtained as a white solid (75%).

mp 154°–156° C.;

$^1$H-NMR-(CDCl$_3$) δ (TMS): 2.54 (s, 3H), 3.69 (s, 2H+H$_2$O), 4.38 (s, 2H), 6.8–7.6, (m, 13H).

Analysis calculated for C$_{25}$H$_{20}$N$_6$O$_2$.2H$_2$O: C 63.55%; H 5.12%; N 17.79%. Found: C 63.43%; H 4.84%; N 17.48%.

EXAMPLE 31

Methyl 1-(ethoxycarbonylmethyl)-3-methyl-5-[[2'-(1H-tetrazol-5-yl)-1,1'-biphenyl-4-yl]methyl]-1H-pyrazole-4-carboxylate Following the procedure described in example 1, but starting from the compound obtained in reference example 39, a 8:2 mixture of regioisomers was obtained, from which the title compound was separated by recrystallization from EtOAc (31%).

$^1$H-NMR-(CDCl$_3$) δ (TMS): 1.21 (t, J=7.2 Hz, 3H), 2.41 (s, 3H), 3.83 (s, 3H), 4.10 (q, J=7.2 Hz, 2H), 4.43 (s, 2H), 4.75 (s, 2H), 7.18 (s, 4H), 7.5 (m, 4H), 8.1 (m, 1H).

EXAMPLE 32

1Carboxymethyl-3-methyl-5-[[2'-(1H-tetrazol-5-yl)-1,1'-biphenyl-4-yl]methyl]-1H-pyrazole-4-carboxylic acid Following the procedure described in example 2, but starting from the compound obtained in example 31, the title compound was obtained (89%).

$^1$H-NMR-(CDCl$_3$+CD$_3$OD) δ (TMS): 2.44 (s, 3H), 4.15 (s, 2H+H$_2$O), 4.39 (s, 2H), 4.55 (s, 2H), 7.06 (s, 4H), 7.5 (m, 5H).

EXAMPLE 33

Methyl 3-methyl-1-propyl-5-[[2'-(1H-tetrazol-5-yl)-1,1'-biphenyl-4-yl]methyl]-1H-pyrazole-4-carboxylate Methyl 5-methyl-1-propyl-3-[[2'-(1H-tetrazol-5-yl)-1,1'-biphenyl-4-yl]methyl]-1H-pyrazole-4-carboxylate Following the procedure described in example 1, but starting from the compound obtained in reference example 41, the title compound was obtained as a 55:45 mixture of regioisomers (80%).

$^1$H-NMR-(CDCl$_3$) δ (TMS): 0.79 (t, J=7.2 Hz, 0.55×3H), 0.88 (t, J=7.2 Hz, 0.45×3H), 1.7 (m, 2H), 2.32 (s, 0.55×3H), 2.49 (s, 0.45×3H), 3.76 (s, 3H), 3.9 (m, 2H), 4.16 (s, 0.45×2H), 4.35 (s, 0.55×2H), 7.09 (s, 4H), 7.5 (m, 4H), 8.1 (m, 1H).

EXAMPLE 34

3-Methyl-1-propyl-5-[[2'-(1H-tetrazol-5-yl)-1,1'-biphenyl-4-yl]methyl]-1H-pyrazole-4-carboxylic acid Following the procedure described in example 2, but starting from the compound obtained in example 33, the title compound was obtained (86%) as a mixture of regioisomers, from which the title compound was obtained as a white solid by recrystallization from EtOAc/MeOH.

mp 240°–242° C.;

$^1$H-NMR-(CDCl$_3$+CD$_3$OD) δ (TMS): 0.76 (t, J=7.2 Hz, 3H), 1.6 (m, 2H), 2.41 (s, 3H), 3.88 (t, J=7.2 Hz, 2H), 4.15 (s, 2H+H$_2$O), 4.43 (s, 2H), 7.08 (s, 4H), 7.57 (m, 4H).

Analysis calculated for $C_{22}H_{22}N_6O_2$: C 65.66%; H 5.51%; N 20.88%. Found: C 65.34%; H 5.49%; N 20.72%.

EXAMPLE 35

Ethyl 3-benzyl-1-propyl-5-[[2'-(1H-tetrazol-5-yl)-1, 1'-biphenyl-4-yl]methyl]-1H-pyrazole-4-carboxylate Ethyl 5-benzyl-1-propyl-3-[[2'-(1H-tetrazol-5-yl)-1, 1'-biphenyl-4-yl]methyl]-1H-pyrazole-4-carboxylate Following the procedure described in example 1, but starting from the compound obtained in reference example 45, the title compound was obtained as a white solid as a 1:1 mixture of regioisomers (89%).

$^1$H-NMR-(CDCl$_3$) δ (TMS): 0.78 (t, J=7.2 Hz, 0.5×3H), 0.84 (t, J=7.2 Hz, 0.5×3H), 1.18 (t, J=7.2 Hz, 0.5×3H), 1.21 (t, J=7.2 Hz, 0.5×3H), 1.69 (m, 2H), 3.7–4.5 (m, 8H), 7.0–7.5 (m, 13H), 8.1 (m, 1H).

EXAMPLE 36

3-Benzyl-1-propyl-5-[[2'-(1H-tetrazol-5-yl)-1,1'-biphenyl-4-yl]methyl]-1H-pyrazole-4-carboxylic acid 5-Benzyl-1-propyl-3-[[2'-(1H-tetrazol-5-yl)-1,1'-biphenyl-4-yl]methyl]-1H-pyrazole-4-carboxylic acid Following the procedure described in example 2, but starting from the compound obtained in example 35, the title compound was obtained as a white solid as a 1:1 mixture of regioisomers (76%).

$^1$H-NMR-(CDCl$_3$) δ (TMS): 0.78 (t, J=7.2 Hz, 0.5×3H), 0.84 (t, J=7.2 Hz, 0.5×3H), 1.69 (m, 2H), 3.7–4.5 (m, 6H), 7.0–7.5 (m, 14H), 8.1 (m, 1H).

Analysis calculated for $C_{28}H_{26}N_6O_2 \cdot H_2O$: C 67.73%; H 5.68%; N 16.92%. Found: C 67.78%; H 5.81%; N 16.41%.

EXAMPLE 37

Ethyl 1-butyl-5-[[2'-(1H-tetrazol-5-yl)-1,1'-biphenyl-4-yl]methyl]-1H-pyrazole-4-carboxylate Following the procedure described in example 1, but starting from the compound obtained in reference example 49, the title compound was obtained as a 9:1 mixture of regioisomers (79%), from which the desired compound was obtained as a white solid by recrystallization from EtOAc.

mp 144° C.;

$^1$H-NMR-(CDCl$_3$) δ (TMS): 1.88 (t, J=7.2 Hz, 3H), 1.33 (t, J=7.2 Hz, 3H), 1.0–1.7 (m, 4H), 4.01 (t, J=7.2 Hz, 2H), 4.29 (q, J=7.2 Hz, 2H), 4.45 (s, 2H), 7.18 (s, 4H), 7.5 (m, 4H), 7.93 (s, 1H), 8.2 (m, 1H).

Analysis calculated for $C_{24}H_{26}N_6O_2$: C 66.96%; H 6.09%; N 19.52%. Found: C 66.86%; H 6.09%; N 19.42%.

EXAMPLE 38

1-Butyl-5-[[2'-(1H-tetrazol-5-yl)-1,1'-biphenyl-4-yl]methyl]-1H-pyrazole-4-carboxylic acid Following the procedure described in example 2, but starting from the compound obtained in example 37, the title compound was obtained as a white solid (71%).

mp 216°–217° C.;

$^1$H-NMR-(CDCl$_3$+CD$_3$OD) δ (TMS): 0.8–1.7 (m, 7H), 3.88 (s, 2H+H$_2$O), 3.95 (t, J=7.2 Hz, 2H), 4.42 (s, 2H), 7.08 (s, 4H), 7.5 (m, 4H), 7.93 (s, 1H).

Analysis calculated for $C_{22}H_{22}N_6O_2 \cdot 0.25H_2O$: C 64.92%; H 5.57%; N 20.64 Found: C 64.95%; H 5.53%; N 20.62%.

EXAMPLE 39 a) 1-Butyl-5-methyl-3-[[2'-(1H-tetrazol-5-yl)-1,1'-biphenyl-4-yl]methyl]-1H-pyrazole-4-carboxaldehyde
b) 1-Butyl-3-methyl-5-[[2'-(1H-tetrazol-5-yl)-1,1'-biphenyl-4-yl]methyl]-1H-pyrazole-4-carboxaldehyde Following the procedure described in example 1, but starting from isomer a) of the compound obtained in reference example 51, isomer a) of the title compound was obtained.

mp 64°–70° C.;

$^1$H-NMR-(CDCl$_3$) δ (TMS): 0.93 (t, J=6.4 Hz, 3H), 1.1–2.0 (m, 4H), 2.47 (s, 3H), 3.99 (t, J=8 Hz, 2H), 4.16 (s, 2H), 6.8–8.0 (m, 8H), 9.81 (s, 1H).

Analysis calculated for $C_{23}H_{24}N_6 \cdot H_2O$: C 66.01%; H 6.26%; N 20.08%. Found: C 65.75%; H 5.88%; N 19.84%.

Following essentially the same procedure, but starting from isomer b) of reference compound 51, isomer b) of the title compound was obtained in 51% yield.

mp 81°–85° C.;

$^1$H-NMR-(CDCl$_3$) δ (TMS): 0.86 (t, J=6.4 Hz, 3H), 1.1–2.0 (m, 4H), 2.41 (s, 3H), 3.91 (t, J=8 Hz, 2H), 4.31 (s, 2H), 7.09 (s, 4H), 7.5 (m, 3H), 8.2 (m, 1H), 9.81 (s, 1H).

Analysis calculated for $C_{23}H_{24}N_6O \cdot 0.25H_2O$: C 68.21%; H 6.10%; N 20.74%. Found: C 68.37%; H 6.05%; N 19.78%.

EXAMPLE 40

4-Acetyl-1-butyl-3-methyl-5-[[2'-(1H-tetrazol-5-yl)-1,1'-biphenyl-4-yl]methyl]-1H-pyrazole 4-Acetyl-1-butyl-5-methyl-3-[[2'-(1H-tetrazol-5-yl)-1,1'-biphenyl-4-yl]methyl]-1H-pyrazole Following the procedure described in example 1, but starting from the compound obtained in reference example 55, the title compound was obtained as a 1:1 mixture of regioisomers (62%).

$^1$H-NMR-(CDCl$_3$) δ (TMS): 0.7–2.0 (m, 7H), 2.52 (5.0× 3H), 2.55 (s, 0.5×3H), 2.61 (s, 0.5×3H), 2.65 (s, 0.5×3H), 4.07 (t, J=7.2 Hz, 0.5×2H), 4.16 (t, J=7.2 Hz, 0.5×2H), 4.35 (s, 0.5×2H), 4.49 (s, 0.5×2H), 6.9–7.6 (m, 8H), 8.2 (m, 1H).

Analysis calculated for $C_{24}H_{26}N_6O \cdot 0.5H_2O$: C 68.06%; H 6.42%; N 19.84%. Found: C 67.99%; H 6.26%; N 19.47%.

EXAMPLE 41

Ethyl 3-isopropyl-5-[[2'-(methoxycarbonyl)-1,1'-biphenyl-4-yl]methyl]-1-propyl-1H-pyrazole-4-carboxylate A mixture of the compound obtained in reference example 13a (0.5 g, 1.3 mmol), methyl 2-chlorobenzoate (0.22 g, 1.3 mmol), NiCl$_2$ (0.017 g, 0.13 mmol), triphenylphosphine (0.07 g, 0.26 mmol) and pyridine (1.3 mL) was heated at 80° C. under an argon atmosphere. Next, powdered zinc (0.178 g, 2.73 mmol) was added and the mixture was heated at 80° C. for 5 h. It was then allowed to cool, filtered through celite, and washed with toluene. The filtrate was concentrated, taken up in toluene, filtered and washed again with toluene. The new filtrate was washed with 1N HCl, saturated NaHCO$_3$ solution and H$_2$O. The organic phase was dried and concentrated. The aqueous phase was extracted with EtOAc, dried and concentrated. The combined residues were chromatographed on silica gel (hexane-EtOAc mixtures of increasing polarity) to afford the desired product (0.3 g, 53%).

$^1$H-NMR-(CDCl$_3$) δ (TMS): 0.82 (t, J=7.2 Hz, 3H), 1.29 (t, J=7.2 Hz, 3H), 1.30 (d, J=6.4 Hz, 6H), 1.70 (m, 2H), 3.57 (q, J=6.4 Hz, 1H), 3.60 (s, 3H), 3.90 (t, J=7.2 Hz, 2H), 4.28 (q, J=7.2 Hz, 2H), 4.40 (s, 2H), 7.0–8.0 (m, 8H).

EXAMPLE 42

5-[[2'-(Carboxy)-1,1'-biphenyl-4-yl]methyl]-3-isopropyl-1-propyl-1H-pyrazole-4-carboxylic acid Following a similar procedure to that described in example 6, but starting from the compound obtained in example 41, the title compound was obtained as a white solid in 55% yield.

mp 226°–230° C.;

$^1$H-NMR-(CDCl$_3$+CD$_3$OD) δ (TMS): 0.78 (t, J=7.2 Hz, 3H), 1.27 (d, J=6.4 Hz, 6H), 1.60 (m, 2H), 3.62 (q, J=6.4 Hz, 1H), 3.92 (t, J=7.2 Hz, 2H), 4.47 (s, 2H), 4.70 (s, 2H+H$_2$O), 7.0–8.0 (m, 8H).

Analysis calculated for C$_{28}$H$_{26}$N$_6$O$_2$.KOH: C 62.32%; H 5.88%; N 6.06%. Found: C 62.49%; H 5.57%; N 6.41%.

EXAMPLE 43

Methyl 3-ethyl-1-propyl-5-[[2'-(tert-butylaminosulfonyl)-1,1'-biphenyl-4-yl]methyl]-1H-pyrazole-4-carboxylate Methyl 5-ethyl-1-propyl-3-[[2'-(tert-butylaminosulfonyl)-1,1'-biphenyl-4-yl]methyl]-1H-pyrazole-4-carboxylate Following the procedure described in reference example 4, but starting from the compound obtained in reference example 18 and using the compound obtained in reference example 56 instead of 2-(2'-triphenylmethyl-2'H-tetrazol-5-yl)phenylboronic acid, the title compound was obtained as a 1:1 mixture of regioisomers (76%).

$^1$H-NMR-(CDCl$_3$+CD$_3$OD) δ (TMS): 0.86 (t, J=7.2 Hz, 3H), 0.97 (s, 9H), 1.26 (t, J=7.2 Hz, 3H), 1.66 (m, 2H), 2.90 (q, J=7.2 Hz, 2H), 3.76 (s, 0.5×3H), 3.80 (s, 0.5×3H), 4.01 (t, J=7.2 Hz, 2H), 4.21 (s, 0.5×2H), 4.43 (s, 0.5×2H), 7.5 (m, 7H), 8.2 (s, 1H).

EXAMPLE 44

Methyl 5-[[2'-(aminosulfonyl)-1,1'-biphenyl-4-yl]methyl]-3-ethyl-1-propyl-1H-pyrazole-4-carboxylate To a solution of the compound obtained in example 43 (2.65 g, 5.3 mmol) in trifluoroacetic acid (58 mL) was added anisole (1 mL) and the mixture stirred under an argon atmosphere for 18 h. The solvent was concentrated and the residue purified by chromatography on silica-gel (hexane-EtOAc mixtures) to give a 1:1 mixture of regioisomers, from which the title compound was obtained as a white solid by recrystallization from EtOAc (1.34 g, 57%).

mp 144° C.;

$^1$H-NMR-(CDCl$_3$) δ (TMS): 0.84 (t, J=7.2 Hz, 3H), 1.26 (t, J=7.2 Hz, 3H), 1.66 (m, 2H), 2.90 (q, J=7.2 Hz, 2H), 3.81 (s, 3H), 3.92 (t, J=7.2 Hz, 2H), 4.13 (s, 2H), 4.44 (s, 2H), 7.5 (m, 7H), 8.2 (m, 1H).

Analysis calculated for C$_{23}$H$_{27}$N$_3$O$_4$S.0.5H$_2$O: C 61.31%; H 6.26%; N 9.32%; S 7.11%. Found: C 61.41%; H 6.21%; N 9.28%; S 6.60%.

EXAMPLE 45

Methyl 3-ethyl-5-[[2'-(phenylcarbonylaminosulfonyl)-1,1'-biphenyl-4-yl]methyl]-1-propyl-1H-pyrazole-4-carboxylate To a solution of the compound obtained in example 44 (0.5 g, 1.13 mmol) in pyridine (10.8 mL) was added benzoyl chloride (0.13 mL) and the reaction mixture was stirred at room temperature under an argon atmosphere for 12 h. Then, saturated aqueous KH$_2$PO4 (33 mL) was added and it was extracted with EtOAc. The organic phase was unwashed with 1N HCl, dried and concentrated to a crude product. This was chromatographed on silica gel (hexane-EtOAc, 1:1) to afford the title compound as a foam (0.64 g, 100%).

$^1$H-NMR-(CDCl$_3$) δ (TMS): 0.86 (t, J=7.2 Hz, 3H), 1.27 (t, J=7.2 Hz, 3H), 1.75 (m, 2H), 2.90 (q, J=7.2 Hz, 2H), 3.78 (s, 3H), 3.92 (t, J=7.2 Hz, 2H), 4.37 (s, 2H), 7.5 (m, 12H), 8.2 (m, 1H), 8.4 (m, 1H).

EXAMPLE 46

3-Ethyl-5-[[2'-(phenylcarbonylaminosulfonyl)-1,1'-biphenyl-4-yl]methyl]-1-propyl-1H-pyrazole-4-carboxylic acid Following the procedure described in example 2, but starting from the compound obtained in example 45, the title compound was obtained as a white solid (0.228 g, 38%).

mp 202°–206° C.;

$^1$H-NMR-(CDCl$_3$) δ (TMS): 0.84 (t, J=7.2 Hz, 3H), 1.28 (t, J=7.2 Hz, 3H), 1.70 (m, 2H), 2.93 (q, J=7.2 Hz, 2H), 3.88 (t, J=7.2 Hz, 2H), 4.33 (s, 2H), 7.5 (m, 14), 8.4 (m, 1H).

Analysis calculated for C$_{29}$H$_{29}$N$_3$O$_5$S: C 65.52%; H 5.50%; N 7.90%; S 6.03%. Found: C 65.32%; H 5.65%; N 7.90%; S 6.6%.

EXAMPLE 47

Methyl 3-ethyl-1-propyl-5-[[2'-(tert-butoxycarbonylaminosulfonyl)-1,1'-biphenyl-4-yl]methyl]-1H-pyrazole-4-carboxylate A mixture of the compound obtained in example 44 (0.5 g, 1.13 mmol), di-tertbutyl dicarbonate (0.49 g, 2.26 mmol), K$_2$CO$_3$ (0.31 g, 2.26 mmol) and anhydrous DME (23.3 mL) was refluxed under an argon atmosphere for 2 h. The resulting solution was allowed to cool and was then poured into 10% NaHSO$_4$ (99.7 mL) and extracted with EtOAc. The organic phase was dried and concentrated to a crude product, which was chromatographed on silica gel hexane-EtOAc) to afford the title compound as an oil (0.27 g, 44%).

$^1$H-NMR-(CDCl$_3$)δ (TMS): 0.85 (t, J=7.2 Hz, 3H), 1.28 (t, J=7.2 Hz, 3H), 1.28 (s, 9H), 1.75 (m, 2H), 2.90 (q, J=7.2 Hz, 2H), 3.78 (s, 3H), 3.81 (t, J=7.2 Hz, 2H) 4.44 (s, 2H), 7.0–7.8 (m, 8H), 8.4 (m, 1H).

EXAMPLE 48

3-Ethyl-1-propyl-5-[[2'-(tert-butoxycarbonylaminosulfonyl)-1,1'-biphenyl-4-yl]methyl]-1H-pyrazole-4-carboxylic acid Following the procedure described in example 2, but starting from the compound obtained in example 47, the title compound was obtained as a white solid (45%).

mp 147°–149° C.;

$^1$H-NMR-(CDCl$_3$) δ (TMS): 0.86 (t, J=7.2 Hz, 3H), 1.26 (t, J=7.2 Hz, 3H), 1.26 (s, 9H), 1.75 (m, 2H), 2.90 (q, J=7.2

Hz, 2H), 3.96 (t, J=7.2 Hz, 2H), 4.44 (s, 2H), 7.0–7.6 (m, 9H), 8.3 (m, 1H).

Analysis calculated for $C_{27}H_{33}N_3O_6S$: C 61.46%; H 6.30%; N 7.96%; S 6.08%. Found: C 61.48%; H 6.34%; N 8.00%; S 5.77%.

EXAMPLE 49

Methyl 1-butyl-3-methyl-5-[[2'-(tert-butylaminosulfonyl)-1,1'-biphenyl-4-yl]methyl]-1H-pyrazole-4-carboxylate Following the procedure described in example 43, but starting from the compound obtained in reference example 7, a 70:30 mixture of regioisomers was obtained, from which the title compound was obtained as a white solid by recrystallization from $CH_2Cl_2$/EtOAc/hexane (21%).

mp 163°–164° C.;

$^1$H-NMR-(CDCl$_3$) δ (TMS): 0.7–2.0 (m, 7H), 0.97 (s, 9H), 2.46 (s, 3H), 2.46 (s, 1H), 3.80 (s, 3H), 3.92 (t, J=8 Hz, 2H), 4.43 (s, 2H), 7.0–7.6 (m, 7H), 8.2 (m, 1H).

EXAMPLE 50

Methyl 5-[[2'-(aminosulfonyl)-1,1'-biphenyl-4-yl]methyl]-1-butyl-3-methyl-1H-pyrazole-4-carboxylate Following the procedure described in example 44, but starting from the compound obtained in example 49, the title compound was obtained as a white solid in 98% yield.

mp 49°–54° C.;

$^1$H-NMR-(CDCl$_3$) δ (TMS): 0.7–2.0 (m, 7H), 2.44 (s, 3H), 2.46 (s, 1H), 3.72 (s, 3H), 3.92 (t, J=8 Hz, 2H), 4.39 (s, 2H), 4.42 (s, 2H), 7.0–7.6 (m, 7H), 8.2 (m, 1H).

EXAMPLE 51

Methyl 1-butyl-3-methyl-5-[[2'-(tert-butoxycarbonylaminosulfonyl)-1,1'-biphenyl-4-yl]methyl]-1H-pyrazole-4-carboxylate Following the procedure described in example 47, but starting from the compound obtained in example 50, the title compound was obtained as an oil in 70% yield.

$^1$H-NMR-(CDCl$_3$) δ (TMS): 0.7–2.0 (m, 7H), 1.29 (s, 9H), 2.44 (s, 3H), 3.46 (s, 1H), 3.80 (s, 3H), 3.96 (t, J=8 Hz, 2H), 4.45 D (s, 2H), 7.0–7.6 (m, 7H), 8.2 (m, 1H).

EXAMPLE 52

1-Butyl-3-methyl-5-[[2'-(tert-butoxycarbonylaminosulfonyl)-1,1'-biphenyl-4-yl]methyl]-1H-pyrazole-4-carboxylic acid A mixture of the compound obtained in example 51 (0.26 g, 0.5 mmol), 2N NaOH (2.5 mL) and EtOH (25 mL) was stirred at room temperature for 6 days. The solvent was removed and the residue taken up in EtOAc-$H_2O$. The aqueous phase was acidified and extracted with EtOAc, dried and concentrated to afford the desired product as a white solid (0.1 g, 38%).

mp 92°–96° C.;

$^1$H-NMR-(CDCl$_3$) δ (TMS): 0.7–2.0 (m, 7H), 1.29 (s, 9H), 2.45 (s, 3H), 3.96 (t, J=8 Hz, 2H), 4.45 (s, 2H), 7.0–7.6 (m, 9H), 8.2 (m, 1H).

Analysis calculated for $C_{27}H_{33}N_3O_6S.0.5H_2O$: C 60.42%; H 6.38%; N 7.83%; S 5.97%. Found: C 60.41%; H 6.30%; N 7.81%; S 5.58%.

EXAMPLE 53

Methyl 1-butyl-5-[[2'-(isobutoxycarbonylaminosulfonyl)-1,1'-biphenyl-4-yl]methyl]-3-methyl-1H-pyrazole-4-carboxylate Following the procedure described in example 51, but using isobutyl chloroformate instead of di-tertbutyl dicarbonate, the title compound was obtained as an oil in 39% yield.

$^1$H-NMR-(CDCl$_3$) δ (TMS): 0.78 (d, J=6.4 Hz, 6H), 0.7–2.0 (m, 8H), 2.46 (s, 3H), 3.86 (s, 3H), 3.96 (m, 5H), 4.45 (s, 2H), 7.0–7.6 (m, 7H), 8.2 (m, 1H).

EXAMPLE 54

1-Butyl-5-[[2'-(isobutoxycarbonylaminosulfonyl)-1,1'-biphenyl-4-yl]methyl]-3-methyl-1H-pyrazole-4-carboxylic acid Following the procedure described in example 52, but starting from the compound obtained in example 53, the title compound was obtained as a white solid (35%).

mp 79°–82° C.;

$^1$H-NMR-(CDCl$_3$) δ (TMS): 0.78 (d, J=6.4 Hz, 6H), 0.7–2.0 (m, 8H), 2.46 (s, 3H), 3.96 (m, 4H), 4.45 (s, 2H), 7.0–7.6 (m, 9H), 8.3 (m, 1H).

Analysis calculated for $C_{27}H_{33}N_3O_6S$: C 61.46%; H 6.30%; N 7.96%; S 6.08%. Found: C 61.48%; H 6.17%; N 7.79%; S 5.76%.

EXAMPLE 55

Methyl 1-butyl-3-methyl-5-[[2'-(phenylcarbonylaminosulfonyl)-1,1'-biphenyl-4-yl]methyl]-1H-pyrazole-4-carboxylate Following the procedure described in example 45, but starting from the compound obtained in example 50, the title compound was obtained as an oil in 83% yield.

$^1$H-NMR-(CDCl$_3$) δ (TMS): 0.7–2.0 (m, 7H), 2.44 (s, 3H), 3.78 (s, 3H), 3.96 (m, 3H), 4.38 (s, 2H), 7.0–7.6 (m, 12H), 8.2 (m, 1H).

EXAMPLE 56

1-Butyl-3-methyl-5-[[2'-(phenylcarbonylaminosulfonyl)-1,1'-biphenyl-4-yl]methyl]-1H-pyrazole-4-carboxylic acid Following the procedure described in example 2, but starting from the compound obtained in example 55, the title compound was obtained as a white solid (60%).

mp 99°–107° C.;

$^1$H-NMR-(CDCl$_3$) δ (TMS): 0.7–2.0 (m, 7H), 2.49 (s, 3H), 3.96 (m, 3H), 4.35 (s, 2H), 7.0–7.6 (m, 13H), 8.2 (m, 1H).

Analysis calculated for $C_{29}H_{29}N_3O_5S.0.5H_2O$: C 64.43%; H 5.59%; N 7.77%; S 5.93%. Found: C 64.42%; H 5.81%; N 7.94%; S 5.70%.

EXAMPLE 57

Ethyl 3-cyclopropyl-1-propyl-5-[[2'-(tert-butylaminosulfonyl)-1,1'-biphenyl-4-yl]methyl]-1H-pyrazole-4-carboxylate Following the procedure described in example 43, but starting from the compound obtained in reference example 19a, the title compound was obtained as a white solid in 58% yield.

mp 165°–168° C.;

$^1$H-NMR-(CDCl$_3$) δ (TMS): 0.82 (t, J=7.2 Hz, 3H), 0.91 (d, 4H), 0.95 (s, 9H), 1.30 (t, J=7.2 Hz, 3H), 1.70 (m, 2H), 2.47 (m, 1H), 3.86 (t, J=7.2 Hz, 2H), 4.28 (q, J=7.2 Hz, 2H), 4.41 (s, 2H), 7.0–7.5 (m, 8H), 8.2 (m, 1H).

EXAMPLE 58

Ethyl 5-[[2'-(aminosulfonyl)-1,1'-biphenyl-4-yl]methyl]-3-cyclopropyl-1-propyl-1H-pyrazole-4-carboxylate Following the procedure described in example 44, but starting from the compound obtained in example 57, the title compound was obtained as a foam in 77% yield.

mp 70°–77° C.;

$^1$H-NMR-(CDCl$_3$) δ (TMS): 0.82 (t, J=7.2 Hz, 3H), 0.91 (d, 4H), 1.32 (t, J=7.2 Hz, 3H), 1.70 (m, 2H), 2.47 (m, 1H), 3.45 (s, 2H), 3.87 (t, J=7.2 Hz, 2H), 4.30 (q, J=7.2 Hz, 2H), 4.43 (s, 2H), 7.0–7.5 (m, 7H), 8.2 (m, 1H).

EXAMPLE 59

Ethyl 3-cyclopropyl-5-[[2'-(plenylcarbonylaminosulfonyl)-1,1'-biphenyl-4-yl]methyl]-1-propyl-1H-pyrazole-4-carboxylate Following the procedure described in example 45, but starting from the compound obtained in example 58, the title compound was obtained as a foam in 64% yield.

$^1$H-NMR-(CDCl$_3$) δ (TMS): 0.82 (t, J=7.2 Hz, 3H), 0.91 (d, 4H), 1.32 (t, J=7.2 Hz, 3H), 1.70 (m, 2H), 2.47 (m, 1H), 3.45 (s, 2H), 3.84 (t, J=7.2 Hz, 2H), 4.33 (s, 2H), 7.0–7.5 (m, 13H), 8.2 (m, 1H).

EXAMPLE 60

3-Cyclopropyl-5-[[2'-(phenylcarbonylaminosulfonyl)-1,1'-biphenyl-4-yl]methyl]-1-propyl-1H-pyrazole-4-carboxylic acid Following the procedure described in example 2, but starting from the compound obtained in example 59, the title compound was obtained as a white solid in 82% yield.

mp 230°–232° C.;

$^1$H-NMR-(CDCl$_3$+CD$_3$OD) δ (TMS): 0.82 (t, J=7.2 Hz, 3H), 0.91 (d, 4H), 1.68 (m, 2H), 2.59 (m, 1 H), 3.86 (t, J=7.2 Hz, 2H), 4.26 (s, 2H+H$_2$O), 4.41 (s, 2H), 7.0–7.5 (m, 12H), 8.2 (m, 1H).

Analysis calculated for C$_{30}$H$_{29}$N$_3$O$_5$S.H$_2$O: C 64.16%; H 5.56%; N 7.48%; S 5.71%. Found: C 64.59%; H 5.37%; N 7.52%; S 5.40%.

EXAMPLE 61

3-Cyclopropyl-5-[[2'-(phenylcarbonylaminosulfonyl)-1,1'-biphenyl-4-yl]methyl]-1-propyl-1H-pyrazole-4-carboxamide To a solution of the compound obtained in example 60 (0.15 g, 0.28 mmol) in THF (10 mL) was added 1,1'-carbonyldiimidazole (0.057 g, 0.35 mmol) and the mixture was stirred at room temperature under an argon atmosphere for 3 h. Next, ammonia (32% aqueous solution, 0.33 mL) and EtOH (0.7 mL) were added and the reaction mixture was stirred at room temperature overnight and then at reflux for 1 h. The solvent was removed, the residue was taken up in CH$_2$Cl$_2$ and H$_2$O was added. The aqueous phase was acidified to pH=6 and extracted with EtOAc. The combined organic extracts were dried and concentrated to a crude product. This was chromatographed on silica gel (hexane-EtOAc mixtures of increasing polarity) to afford the title compound as a white solid (40%).

mp 187°–191° C.;

$^1$H-NMR-(CDCl$_3$) δ (TMS): 0.82 (t, J=7.2 Hz, 3H), 0.91 (d, 4H), 1.68 (m, 2H), 2.59 (m, 1H), 3.86 (t, J=7.2 Hz, 2H), 4.32 (s, 2H), 6.6 (broad s, 2H), 7.0–7.5 (m, 13H), 8.2 (m, 1H).

Analysis calculated for C$_{30}$H$_{30}$N$_4$O$_4$S: C 66.40%; H 5.57%; N 10.32%; S 5.91%. Found: C 66.45%; H 5.43%; N 10.39%; S 5.56%.

EXAMPLE 62

Ethyl 3-cyclopropyl-1-ethyl-5-[[2'-(tert-butylaminosulfonyl)-1,1'-biphenyl-4-yl]methyl]-1H-pyrazole-4-carboxylate Following the procedure described in example 43, but starting from the compound obtained in reference example 20a, the title compound was obtained as a white solid in 35% yield.

mp 197°–199° C.:

$^1$H-NMR-(CDCl$_3$) δ (TMS): 0.91 (d, 4H), 0.98 (s, 9H), 1.23 (t, J=7.2 Hz, 3H), 1.32 (t, J=7.2 Hz, 3H), 2.50 (m, 1H), 3.98 (q, J=7.2 Hz, 2H), 4.29 (q, J=7.2 Hz, 2H), 4.42 (s, 2H), 7.0–7.5 (m, 8H), 8.2 (m, 1H).

EXAMPLE 63

Ethyl 5-[[2'-(aminosulfonyl)-1,1'-biphenyl-4-yl]methyl]-3-cyclopropyl-1-ethyl-1H-pyrazole-4-carboxylate Following the procedure described in example 44, but starting from the compound obtained in example 62, the title compound was obtained as a white solid in 86% yield.

mp 54°–58° C.;

$^1$H-NMR-(CDCl$_3$) δ (TMS): 0.91 (d, 4H), 1.22 (t, J=7.2 Hz, 3H), 1.30 (t, J=7.2 Hz, 3H), 2.50 (m, 1H), 3.98 (q, J=7.2 Hz, 2H), 4.16 (s, 2H), 4.29 (q, J=7.2 Hz, 2H), 4.42 (s, 2H), 7.0–7.5 (m, 7H), 8.2 (m, 1H).

EXAMPLE 64

Ethyl 3-cyclopropyl-1-ethyl-5-[[2'-(phenylcarbonylaminosulfonyl)-1,1'-biphenyl-4-yl]methyl]-1H-pyrazole-4-carboxylate Following the procedure described in example 45, but starting from the compound obtained in example 63, the title compound was obtained as a white solid (90%).

mp 70°–76° C.;

$^1$H-NMR-(CDCl$_3$) δ (TMS): 0.91 (d, 4H), 1.22 (t, J=7.2 Hz, 3H), 1.30 (t, J=7.2 Hz, 3H), 2.50 (m, 1H), 3.98 (q, J=7.2 Hz, 2H), 4.29 (q, J=7.2 Hz, 2H), 4.35 (s, 2H), 7.0–7.5 (m, 13H), 8.2 (m, 1H).

EXAMPLE 65

3-Cyclopropyl-1-ethyl-5-[[2'-(phenylcarbonylaminosulfonyl)-1,1'-biphenyl-4-yl]methyl]-1H-pyrazole-4-carboxylic acid Following the procedure described in example 2, but starting from the compound obtained in example 64, the title compound was obtained as a white solid in 87% yield.

mp 217° C.;

¹H-NMR-(CDCl₃) δ (TMS): 0.91 (d, 4H), 1.24 (t, J=7.2 Hz, 3H), 2.59 (m, 1H), 3.95 (q, J=7.2 Hz, 2H), 4.41 (s, 2H), 7.0–7.5 (m, 14H), 8.2 (m, 1H).

Analysis calculated for $C_{29}H_{27}N_3O_5S \cdot H_2O$: C 63.61%; H 5.34%; N 7.67%; S 5.85%. Found: C 63,79%; H 5.64%; N 7.30%; S 5.07%.

EXAMPLE 66

3-Cyclopropyl-1-ethyl-5-[[2'-(phenylcarbonylaminosulfonyl)-1,1'-biphenyl-4-yl]methyl]-1H-pyrazole-4-carboxamide Following the procedure described in example 14, but starting from the compound obtained in example 65, the title compound was obtained as a white solid (32%).

mp 111°–115° C.;

¹H-NMR-(CDCl₃) δ (TMS): 0.91 (d, 4H), 1.32 (t, J=7.2 Hz, 3H), 2.59 (m, 1H), 4.00 (q, J=7.2 Hz, 2H), 4.36 (s, 2H), 7.0–7.5 (m, 15H), 8.2 (m, 1H).

Analysis calculated for $C_{29}H_{28}N_4O_4S \cdot 0.5DMF$: C 64.82%; H 5.62%; N 11.15%; S 5.66%. Found: C 64.44%; H 5.89%; N 11.04%; S 5.36%.

EXAMPLE 67

Ethyl 3-isopropyl-1-propyl-5-[[2'-(tert-butylaminosulfonyl)-1,1'-biphenyl-4-yl]methyl]-1H-pyrazole-4-carboxylate Following the procedure described in example 43, but starting from the compound obtained in reference example 13a, the title compound was obtained as an oil in 71% yield.

¹H-NMR-(CDCl₃) δ (TMS): 0.86 (t, J=7.2 Hz, 3H), 1.01 (s, 9H), 1.28 (d, J=6.4 Hz, 6H), 1.32 (t, J=7.2 Hz, 3H), 1.69 (m, 2H), 3.59 (q, J=6.4 Hz, 1H), 3.98 (t, J=7.2 Hz, 2H), 4.28 (q, J=7.2 Hz, 2H), 4.48 (s, 2H), 7.0–7.6 (m, 8H), 8.2 (s, 1H).

EXAMPLE 68

Ethyl 5-[[2'-(aminosulfonyl)-1,1'-biphenyl-4-yl]methyl]-3-isopropyl-1-propyl-1H-pyrazole-4-carboxylate Following the procedure described in example 44, but starting from the compound obtained in example 67, the title compound was obtained as an oil in 50% yield.

¹H-NMR-(CDCl₃) δ (TMS): 0.76 (t, J=7.2 Hz, 3H), 1.24 (d, J=6.4 Hz, 6H), 1.25 (t, J=7.2 Hz, 3H), 1.69 (m, 2H), 3.59 (q, J=6.4 Hz, 1H), 3.98 (t, J=7.2 Hz, 2H), 4.28 (q, J=7.2 Hz, 2H), 4.38 (s, 2H), 4.8 (s, 2H), 7.0–7.6 (m, 7H), 8.2 (s, 1H).

EXAMPLE 69

Ethyl 3-isopropyl-5-[[2'-(phenylcarbonylaminosulfonyl)-1,1'-biphenyl-4-yl]methyl]-1-propyl-1H-pyrazole-4-carboxylate Following the procedure described in example 45, but starting from the compound obtained in example 68, the title compound was obtained as a white solid in 74% yield.

mp 159°–160° C.;

¹H-NMR-(CDCl₃) δ (TMS): 0.85 (t, J=7.2 Hz, 3H), 1.27 (d, J=6.4 Hz, 6H), 1.32 (t, J=7.2 Hz, 3H), 1.69 (m, 2H), 3.54 (q, J=6.4 Hz, 1H), 3.90 (t, J=7.2 Hz, 2H), 4.29 (q, J=7.2 Hz, 2H), 4.36 (s, 2H), 7.0–7.6 (m, 13H), 8.2 (s, 1H).

EXAMPLE 70

3-Isopropyl-5-[[2'-(phenylcarbonylaminosulfonyl)-1,1'-biphenyl-4-yl]methyl]-1-propyl-1H-pyrazole-4-carboxylic acid Following the procedure described in example 2, but starting from the compound obtained in example 69, the title compound was obtained as a white solid in 28% yield.

mp 177°–185° C.;

¹H-NMR-(CDCl₃+CD₃OD) δ (TMS): 0.88 (t, J=7.2 Hz, 3H), 1.32 (d, J=6.4 Hz, 6H), 1.69 (m, 2H), 3.54 (q, J=6.4 Hz, 1H), 3.90 (t, J=7.2 Hz, 2H), 4.18 (s, 2H+H₂O), 4.36 (s, 2H), 7.0–7.6 (m, 12H), 8.2 (S, 1H).

Analysis calculated for $C_{30}H_{31}N_3O_5S \cdot 0.5H_2O$: C 64.96%; H 5.81%; N 7.57%; S 5.77%. Found: C 64.98%; H 5.86%; N 7.20%; S 5.21%.

EXAMPLE 71

3-Isopropyl-5-[[2'-(phenylcarbonylaminosulfonyl)-1,1'-biphenyl-4-yl]methyl]-1-propyl-1H-pyrazole-4-carboxamide Following the procedure described in example 61, but starting from the compound obtained in example 70, the title compound was obtained as a white solid in 32% yield.

mp 197°–200° C.;

¹H-NMR-(CDCl₃) δ (TMS): 0.86 (t, J=7.2 Hz, 3H), 1.32 (d, J=6.4 Hz, 6H), 1.69 (m, 2H), 3.14 (q, J=6.4 Hz, 1H), 4.00 (t, J=7.2 Hz, 2H), 4.17 (s, 2H), 5.65 (broad s, 3H), 7.0–7.6 (m, 12H), 8.2 (5, 1H).

Analysis calculated for $C_{30}H_{32}N_4O_4S \cdot 0.5H_2O$: C 65.08%; H 6.01%; N 10.12%; S 5.79%. Found: C 64.98%; H 5.85%; N 10.05%; S 5.46%.

EXAMPLE 72

Ethyl 3-benzyl-1-propyl-5-[[2'-(tert-butylaminosulfonyl)-1,1'-biphenyl-4-yl]methyl]-1H-pyrazole-4-carboxylate Ethyl 5-benzyl-1-propyl-3-[[2'-(tert-butylaminosulfonyl)-1,1'-biphenyl-4-yl]methyl]-1H-pyrazole-4-carboxylate Following the procedure described in example 43, but starting from the compound obtained in reference example 44, the title compound was obtained in 47% yield as a 1:1 mixture of regioisomers.

¹H-NMR-(CDCl₃) δ (TMS): 0.78 (t, J=7.2 Hz, 0.5×3H), 0.84 (t, J=7.2 Hz, 0.5×3H), 0.95 (s, 9H), 1.18 (t, J=7.2 Hz, 0.5×3H), 1.20 (t, J=7.2 Hz, 0.5×3H), 1.63 (m, 2H), 3.60 (s, 0.5×1H), 3.64 (s, 0.5×1H), 3.7–4.5 (m, 8H), 7.0–7.5 (m, 13H), 8.1 (m, 1H).

EXAMPLE 73

Ethyl 5-[[2'-(aminosulfonyl)-1,1'-biphenyl-4-yl]methyl]-3-benzyl-1-propyl-1H-pyrazole-4-carboxylate Ethyl 3-[[2'-(aminosulfonyl)-1,1'-biphenyl-4-yl]methyl]-5-benzyl-1-propyl-1H-pyrazole-4-carboxylate Following the procedure described in example 44, but starting from the compound obtained in example 72, the title compound was obtained in 85% yield as a 1:1 mixture of regioisomers.

¹H-NMR-(CDCl₃) δ (TMS): 0.80 (t, J=7.2 Hz, 0.5×3H), 0.84 (t, J=7.2 Hz, 0.5×3H), 1.19 (t, J=7.2 Hz, 3H), 1.63 (m, 2H), 3.6–4.5 (m, 10H), 7.0–7.5 (m, 12H), 8.1 (m, 1H).

EXAMPLE 74

Ethyl 3-benzyl-5-[[2'-(phenylcarbonylaminosulfonyl)-1,1'-biphenyl-4-yl]methyl]-1-propyl-1H-pyrazole-4-carboxylate Ethyl 5-benzyl-3-[[2'-(phenylcarbonylaminosulfonyl)-1,1'-biphenyl-4-yl]methyl]-1-propyl-1H-pyrazole-4-carboxylate Following the procedure described in example 45, but starting from the compound obtained in example 73, the title compound was obtained in 50% yield as a 1:1 mixture of regioisomers.

¹H-NMR-(CDCl₃) δ (TMS): 0.80 (t, J=7.2 Hz, 0.5×3H), 0.86 (t, J=7.2 Hz, 0.5×3H), 1.19 (t, J=7.2 Hz, 3H), 1.71 (m, 2H), 3.90 (t, J=7.2 Hz, 0.5×2H), 3.91 (t, J=7.2 Hz, 0.5×2H), 3.6–4.5 (m, 7H), 7.0–7.5 (m, 17H), 8.1 (m, 1H).

EXAMPLE 75

3-Benzyl-5-[[2'-(phenylcarbonylaminosulfonyl)-1,1'-biphenyl-4-yl]methyl]-1-propyl-1H-pyrazole-4-carboxylic acid 5-Benzyl-3-[[2'-(phenylcarbonylaminosulfonyl)-1,1'-biphenyl-4-yl]methyl]-1-propyl-1H-pyrazole-4-carboxylic acid Following the procedure described in example 2, but starting from the compound obtained in example 74, the title compound was obtained in 80% yield as a 1:1 mixture of regioisomers.

mp 105°–109° C.;

¹H-NMR-(CDCl₃) δ (TMS): 0.78 (t, J=7.2 Hz, 0.5×3H), 0.84 (t, J=7.2 Hz, 0.5×3H), 1.69 (m, 2H), 3.89 (t, J=7.2 Hz, 0.5×2H), 3.91 (t, J=7.2 Hz, 0.5×2H), 4.27 (s, 2H), 4.35 (s, 0.5×2H), 4.43 (s, 0.5×2H), 7.0–7.5 (m, 19H), 8.1 (m, 1H).

Analysis calculated for $C_{34}H_{31}N_3O_5S \cdot H_2O$: C 66.76%; H 5.44%; N 6.87%; S 5.24%. Found: C 66.98%; H 5.36%; N 6.79%; S 4.98%.

EXAMPLE 76

Ethyl 3-isopropyl-1-propyl-5-[[2'-(trifluoromethylsulfonylamino)-1,1'-biphenyl-4-yl]methyl]-1H-pyrazole-4-carboxylate To a cooled (–70° C.) solution of the compound obtained in reference example 59 (0.202 g, 0.5 mmol) and triethylamine (0.089 mL, 0.64 mmol) in CH₂Cl₂ (3.2 mL), was added dropwise 1M triflic anhydride (0.51 mL) in CH₂Cl₂ and the resulting mixture was stirred under an argon atmosphere for 45 min. A further portion of triflic anhydride (0.064 mL) was added and stirring continued for 15 min. The reaction was allowed to warm up to 0° C. and H₂O (0.64 mL) was added. The reaction mixture was then allowed to warm up to room temperature and more H₂O (6.37 mL) was added. The layers were separated and the organic phase was dried and concentrated. The residue was purified by chromatography on silica gel (hexane-EtOAc mixtures of increasing polarity) to give the title compound as an oil (0.134 g, 50%).

¹H-NMR-(CDCl₃) δ (TMS): 0.81 (t, J=7.2 Hz, 3H), 1.31 (d, J=6.4 Hz, 6H), 1.2–1.8 (m, 5H), 3.56 (q, J=6.4 Hz, 1H), 3.91 (t, J=7.2 Hz, 2H), 4.27 (q, J=7.2 Hz, 2H), 4.44 (s, 2H), 5.91 (broad s, 1H), 6.8–7.5 (m, 8H).

EXAMPLE 77

3-Isopropyl-1-propyl-5-[[2'-(trifluoromethylsulfonylamino)-1,1'-biphenyl-4-yl]methyl]-1H-pyrazole-4-carboxylic acid Following the procedure described in example 2, but starting from the compound obtained in example 76, the title compound was obtained as a white solid in 58% yield.

mp 75°–78° C.;

¹H-NMR-(CDCl₃) δ (TMS): 0.83 (t, J=7.2 Hz, 3H), 1.31 (d, J=6.4 Hz, 6H), 1.62 (m, 2H), 3.56 (q, J=6.4 Hz, 1H), 3.91 (t, J=7.2 Hz, 2H), 4.47 (s, 2H), 7.0–7.5 (m, 10H).

Analysis calculated for $C_{24}H_{26}N_3F_3O_4S$: C 56.57%; H 5.14%; N 8.25%; S 6.29%. Found: C 56.33%; H 5.14%; N 8.06%; S 6.57%.

EXAMPLE 78

3-Isopropyl-1-propyl-5-[[2'-(1H-tetrazol-5-yl)-1,1'-biphenyl-4-yl]methyl]-1H-pyrazole A solution of the compound obtained in example 6a (0.3 g, 0.7 mmol) in acetonitrile (30 mL) was treated with 1N HCl (50 mL) and the reaction mixture was refluxed for 48 h. The mixture was allowed to cool and the solvent was concentrated. The residue thus obtained was dissolved in a mixture of EtOAc and H₂O and the two phases were separated. The aqueous phase was extracted with EtOAc and the combined organic phases dried and concentrated to a crude product. Purification by chromatography on silica gel (hexane-EtOAc, 10%) afforded the title compound as a white solid (0.178 g, 67%).

mp 147°–149° C.;

¹H-NMR-(CDCl₃) δ (TMS): 0.77 (t, J=7.2 Hz, 3H), 1.11 (d, J=6.4 Hz, 6H), 1.65 (m, 2H), 2.73 (q, J=6.4 Hz, 1H), 3.69 (t, J=7.2 Hz, 2H), 3.93 (s, 2H), 5.80 (s, 1H), 7.09 (s, 4H), 7.5 (m, 4H), 8.2 (m, 1H).

Analysis calculated for $C_{23}H_{26}N_6 \cdot 0.25H_2O$: C 70.65%; H 6.84%; N 21.48%. Found: C 70.35%; H 6.62%; N 21.13%.

EXAMPLE 79

Trimethylacetoxymethyl 3-isopropyl-1-propyl-5-[[2'-(1H-tetrazol-5-yl)-1,1'-biphenyl-4-yl]methyl]-1H-pyrazole-4-carboxylate a) 3-Isopropyl-1-propyl-5-[[2'-(2-triphenylmethyl-2H-tetrazol-5-yl)-1,1'-biphenyl-4-yl]methyl]-1H-pyrazole-4-carboxylic acid To a cooled solution (0° C.) of the product obtained in example 6a (2 g, 4.6 mmol) and triethylamine (0.7 mL, 5 mmol) in CH₂Cl₂ (21 mL) was added triphenylchloromethane (1.38 g, 5 mmol) in CH₂Cl₂ (5 mL) and the mixture was stirred under an argon atmosphere for 1 h. The solution was then washed with H₂O, dried and concentrated. The residue was purified by chromatography on silica gel (hexane-EtOAc mixtures of increasing polarity) to give the title compound as a white solid (2.5 g, 80%).

mp 136°–139° C.;

¹H-NMR-(CDCl₃) δ (TMS): 0.81 (t, J=7.2 Hz, 3H), 1.28 (d, J=6.4 Hz, 6H), 1.60 (m, 2H), 3.57 (q, J=6.4 Hz, 1H), 3.72 (t, J=7.2 Hz, 2H), 4.30 (s, 2H), 6.5–7.0 (m, 24H).

b) Trimethylacetoxymethyl 3-isopropyl-1-propyl-5-[[2'-(2-triphenylmethyl-2H-tetrazol-5-yl)-1,1'-biphenyl-4-yl]methyl]-1H-pyrazole-4-carboxylate A solution of the product obtained in example 79a (0.5 g, 0.74 mmol), chloromethyl pivalate (0.13 mL, 0.88 mmol), KI (0.06 g, 0.37 mmol) and K₂CO₃ (0.12 g, 0.88 mmol) in DMF (2.8 mL) was stirred at 60° C. under an argon atmosphere for 2 h. The solution was then diluted with EtOAc and washed with H₂O, dried and concentrated. The residue was purified by chromatography on silica gel (hexane-EtOAc mixtures of increasing polarity) to give the title compound as a white solid (0.63 g, 100%).

mp 128°–130° C.;

¹H-NMR-(CDCl₃) δ (TMS): 0.74 (t, J=7.2 Hz, 3H), 1.17 (s, 9H), 1.28 (d, J=6.4 Hz, 6H), 1.60 (m, 2H), 3.57 (q, J=6.4 Hz, 1H), 3.72 (t, J=7.2 Hz, 2H), 4.29 (s, 2H), 5.87 (s, 2H), 6.5–7.0 (m, 23H).

Analysis calculated for $C_{49}H_{50}N_6O_4$: C 74.79%; H 6.40%; N 10.68%. Found: C 74.33%; H 6.47%; N 10.67%.

c) Title compound

Following the procedure described in example 1, but starting from the compound obtained in example 79b, the title compound was obtained as a white solid (62% for the last two steps).

mp 62°–67° C.;
$^1$H-NMR-(CDCl$_3$) δ (TMS): 0.87 (t, J=7.2 Hz, 3H), 1.11 (s, 9H), 1.31 (d, J=6.4 Hz, 6H), 1.73 (m, 2H), 3.50 (q, J=6.4 Hz, 1H), 3.97 (t, J=7.2 Hz, 2H), 4.36 (s, 2H), 5.84 (s, 2H), 7.11 (s, 4H), 7.5 (m, 4H), 8.2 (m, 1H).

Analysis calculated for C$_{30}$CH$_{36}$N$_6$O$_4$: C 66.16%; H 6.66%; N 15.43%. Found: C 65.86%; H 6.65%; N 15.09%.

EXAMPLE 80

1-(Cyclohexyloxycarbonyloxy)ethyl 3-isopropyl-1-propyl-5-[[2'-(1H-tetrazol-5yl)-1,1'-biphenyl-4-yl]methyl]-1H-pyrazole-4-carboxylate a) 1-(Cyclohexyloxycarbonyloxy)ethyl 3-isopropyl-1-propyl-5-[[2'-(2-triphenylmethyl-2H-tetrazol-5-yl)-1,1'-biphenyl-4-yl]methyl]-1H-pyrazole-4-carboxylate Following the same procedure described in example 79b, but using cyclohexyl-1-chloroethylcarbonate instead of chloromethyl pivalate, the title compound as obtained as a white solid.

$^1$H-NMR-(CDCl$_3$) δ (TMS): 0.89 (t, J=7.2 Hz, 3H), 1.1–2.0 (m, 21H), 3.55 (q, J=6.4 Hz, 1H), 3.98 (t, J=7.2 Hz, 2H), 4.36 (s, 2H), 4.5 (m, 1H), 6.5–7.0 (m, 24H).

b) Title compound

Following the procedure described in example 1, but starting from the compound obtained in example 80a, the title compound was obtained as a white solid (65% overall yield).

mp 79°–83° C.;
$^1$H-NMR-(CDCl$_3$) δ (TMS): 0.89 (t, J=7.2 Hz, 3H), 1.1–2.0 (m, 21H), 3.55 (q, J=6.4 Hz, 1H), 3.98 (t, J=7.2 Hz, 2H), 4.36 (s, 2H), 4.5 (m, 1H), 6.92 (q, J=5 Hz, 1H), 7.09 (s, 4H), 7.5 (m, 4H), 8.2 (m, 1H).

Analysis calculated for C$_{33}$H$_{40}$N$_6$O$_5$: C 5.98%; H 6.71%; N 13.99%. Found: C 65.67%; H 7.14%; N 13.94%.

EXAMPLE 81

Acetoxymethyl 3-isopropyl-1-propyl-5-[[2'-(1H-tetrazol-5-yl)-1,1'-biphenyl-4-yl]methyl]-1H-pyrazole-4-carboxylate a) Acetoxymethyl 3-isopropyl-1-propyl-5-[[2'-(2-triphenylmethyl-2H-tetrazol-5-yl)-1,1'-biphenyl-4-yl]methyl]-1H-pyrazole-4-carboxylate Following the same procedure described in example 79b, but using chloromethyl acetate instead of chloromethyl pivalate, the title compound was obtained as a white solid.

mp 124°–128° C.;
$^1$H-NMR-(CDCl$_3$) δ (TMS): 0.74 (t, J=7.2 Hz, 3H), 1.28 (d, J=6.4 Hz, 6H), 1.60 (m, 2H), 2.0 (s, 3H), 3.57 (q, J=6.4 Hz, 1H), 3.72 (t, J=7.2 Hz, 2H), 4.29 (s, 2H), 5.87 (s, 2H), 6.5–7.0 (m, 23H).

Analysis calculated for C$_{46}$H$_{44}$N$_6$O$_4$: C 74.17%; H 5.95%; N 11.28%. Found: C 73.93%; H 6.07%; N 11.12%.

b) Title compound

Following the procedure described in example 1, but starting from the compound obtained in example 81a, the title compound was obtained as a white solid (32% overall yield).

mp 58°–63° C.;
$^1$H-NMR-(CDCl$_3$) δ (TMS): 0.85 (t, J=7.2 Hz, 3H), 1.30 (d, J=6.4 Hz, 6H), 1.66 (m, 2H), 2.0 (s, 3H), 3.57 (q, J=6.4 Hz, 1H), 3.94 (t, J=7.2 Hz, 2H), 4.35 (s, 2H), 5.81 (s, 2H), 7.09 (s, 4H), 7.5 (m, 4H), 8.2 (m, 1H).

Analysis calculated for C$_{27}$H$_{30}$N$_6$O$_4$: C 64.53%; H 6.02%; N 16.72%. Found: C 64.37%; H 6.00%; N 16.15%.

EXAMPLE 82

Ethyl 3-isopropyl-1-propyl-5-[[2'-(1H-tetrazol-5-yl)-2-fluoro-1,1'-biphenyl-4-yl]methyl]-1H-pyrazole-4-carboxylate Following the procedure described in example 1, but starting from the compound obtained in reference example 66, the title compound was obtained as a white solid (95%).

mp 141° C.;
$^1$H-NMR-(CDCl$_3$) δ (TMS): 0.84 (t, J=7.2 Hz, 3H), 1.28 (t, J=7.2 Hz, 3H), 1.28 (d, J=6.4 Hz, 6H), 1.73 (m, 2H), 3.52 (q, J=6.4 Hz, 1H), 3.91 (t, J=7.2 Hz, 2H), 4.24 (q, J=7.2 Hz, 2H), 4.36 (s, 2H), 6.6–7.5 (m, 7H), 7.82 (m, 1H).

Analysis calculated for C$_{26}$H$_{29}$FN$_6$O$_2$: C 65.53%; H 6.13%; N 17.63%. Found: C 65.72%; H 6.18%; N 17.63%.

EXAMPLE 83

3-Isopropyl-1-propyl-5-[[2'-(1H-tetrazol-5-yl)-2-fluoro-1,1'-biphenyl-4-yl]methyl]-1H-pyrazole-4-carboxylic acid Following the procedure described in example 2, but starting from the compound obtained in example 82, the title compound was obtained as a white solid (80%).

mp 207°–210° C.;
$^1$H-NMR-(CDCl$_3$) δ (TMS): 0.84 (t, J=7.2 Hz, 3H), 1.28 (d, J=6.4 Hz, 6H), 1.73 (m, 2H), 3.52 (q, J=6.4 Hz, 1H), 3.91 (t, J=7.2 Hz, 2H), 4.36 (s, 2H), 6.6–7.5 (m, 8H), 7.82 (m, 1H).

Analysis calculated for C$_{24}$H$_{25}$FN$_6$O$_2$: C 64.27%; H 5.62%; N 18.74%. Found: C 64.21%; H 5.63%; N 18.44%.

EXAMPLE 84

Ethyl 3-isopropyl-1-propyl-5-[[2'-(tert-butylaminosulfonyl)-2-fluoro-1,1'-biphenyl-4-yl]methyl]-1H-pyrazole-4-carboxylate Following the procedure described in example 43, but starting from the compound obtained in reference example 65a, the title compound was obtained as a white solid (89%).

mp 122°–123° C.;
$^1$H-NMR-(CDCl$_3$) δ (TMS): 0.87 (t, J=7.2 Hz, 3H), 1.01 (s, 9H), 1.30 (t, J=7.2 Hz, 3H), 1.32 (d, J=6.4 Hz, 6H), 1.75 (m, 2H), 3.56 (s, 1H), 3.56 (q, J=6.4 Hz, 1H), 3.94 (t, J=7.2 Hz, 2H), 4.27 (q, J=7.2 Hz, 2H), 4.43 (s, 2H), 6.6–7.5 (m, 6H), 7.82 (m, 1H).

Analysis calculated for C$_{31}$H$_{38}$FN$_3$O$_4$S.0.75H$_2$O: C 64.06%; H 6.85%; N 7.23%; S 5.52%. Found: C 63.84%; H 7.10%; N 7.54%; S 6.13%.

EXAMPLE 85

Ethyl 5-[[2'-(aminosulfonyl)-2-fluoro-1,1'-biphenyl-4-yl]methyl]-3-isopropyl-1-propyl-1H-pyrazole-4-carboxylate Following the procedure described in example 44, but starting from the compound obtained in example 84, the title compound was obtained as a white solid (95%).

mp 33°–36° C.;
$^1$H-NMR-(CDCl$_3$) δ (TMS): 0.85 (t, J=7.2 Hz, 3H), 1.29 (t, J=7.2 Hz, 3H), 1.32 (d, J=6.4 Hz, 6H), 1.75 (m, 2H), 3.55 (q, J=6.4 Hz, 1H), 3.94 (t, J=7.2 Hz, 2H), 4.27 (q, J=7.2 Hz, 2H), 4.31 (s, 2H), 4.43 (s, 2H), 6.6–7.5 (m, 6H), 7.82 (m, 1H).

Analysis calculated for C$_{25}$H$_{30}$FN$_3$O$_4$S.0.75H$_2$O: C 59.92%; H 6.33%; N 8.38%; S 6.39%. Found: C 59.64%; H 6.12%; N 8.25%; S 6.77%.

EXAMPLE 86

Ethyl 3-isopropyl-5-[[2'-(isobutoxycarbonylaminosulfonyl)-2-fluoro-1,1'-biphenyl-4-yl]methyl]-1-propyl-1H-pyrazole-4-carboxylate Following the procedure described in example 53, but starting from the compound obtained in example 85, the title compound was obtained as a white solid (74%).

mp 36°–42° C.;

¹H-NMR-(CDCl₃) δ (TMS): 0.80 (d, J=7.2 Hz, 6H), 0.85 (t, J=7.2 Hz, 3H), 1.29 (t, J=7.2 Hz, 3H), 1.32 (d, J=6.4 Hz, 6H), 1.75 (m, 3H), 3.55 (q, J=6.4 Hz, 1H), 3.68 (d, J=8 Hz, 2H), 3.94 (t, J=7.2 Hz, 2H), 4.27 (q, J=7.2 Hz, 2H), 4.42 (s, 2H), 6.6–7.5 (m, 7H), 7.82 (m, 1H).

Analysis calculated for $C_{30}H_{38}FN_3O_6S.0.5H_2O$: C 60.39%; H 6.59%; N 7.04%; S 5.36%. Found: C 60.39%; H 6.61%; N 6.97%; S 5.67%.

EXAMPLE 87

3-Isopropyl-5-[[2'-(isobutoxycarbonylaminosulfonyl)-2-fluoro-1,1'-biphenyl-4-yl]methyl]-1-propyl-1H-pyrazole-4-carboxylic acid Following the procedure described in example 2, but starting from the compound obtained in example 86, the title compound was obtained as a white solid.

mp 77°–82° C.;

¹H-NMR-(CDCl₃) δ (TMS): 0.80 (d, J=7.2 Hz, 6H), 0.85 (t, J=7.2 Hz, 3H), 1.32 (d, J=6.4 Hz, 6H), 1.75 (m, 3H), 3.58 (q, J=6.4 Hz, 1H), 3.74 (d, J=8 Hz, 2H), 3.94 (t, J=7.2 Hz, 2H), 4.44 (s, 2H), 6.6–7.5 (m, 8H), 7.82 (m, 1H).

Analysis calculated for $C_{28}H_{34}FN_3O_6S$: C 60.09%; H 6.12%; N 7.51%; S 5.73%. Found: C 60.22%; H 6.31%; N 7.10%; S 5.61%.

EXAMPLE 88

3-Isopropyl-1-propyl-5-[[2'-(tert-butylaminosulfonyl)-2-fluoro-1,1'-biphenyl-4-yl]methyl]-1H-pyrazole-4-carboxylic acid Following the procedure described in example 2, but starting from the compound obtained in example 84, the title compound was obtained as a white solid (93%).

¹H-NMR-(CDCl₃) δ (TMS): 0.87 (t, J=7.2 Hz, 3H), 1.01 (s, 9H), 1.32 (d, J=6.4 Hz, 6H), 1.75 (m, 2H), 3.56 (s, 1H), 3.56 (q, J=6.4 Hz, 1H), 3.94 (t, J=7.2 Hz, 2H), 4.43 (s, 2H), 6.6–7.5 (m, 7H), 7.82 (m, 1H).

EXAMPLE 89

3-(Phenylcarbonyl)phenylmethyl 3-isopropyl-1-propyl-5-[[2'-(tert-butylaminosulfonyl)-2-fluoro-1,1'-biphenyl-4-yl]methyl]-1H-pyrazole-4-carboxylate Following the procedure described in example 79b, but starting from the compound obtained in example 88 and using 3-bromomethylbenzophenone instead of chloromethyl pivalate, the title compound was obtained (87%).

mp 35°–45° C.;

¹H-NMR-(CDCl₃) δ (TMS): 0.83 (t, J=7.2 Hz, 3H), 0.98 (s, 9H), 1.20 (d, J=6.4 Hz, 6H), 1.80 (m, 2H), 3.42 (q, J=6.4 Hz, 1H), 3.57 (s, 1H), 3.87 (t, J=7.2 Hz, 2H), 4.29 (s, 2H), 5.40 (s, 2H), 6.8–7.8 (m, 15H), 7.82 (m, 1H).

Analysis calculated for $C_{41}H_{44}FN_3O_5S.2H_2O$: C 66.02%; H 6.49%; N 5.63%; S 4.30%. Found: C 66.42%; H 6.09%; N 5.71%; S 3.99%.

EXAMPLE 90

2-(Phenylcarbonyl)phenylmethyl 3-isopropyl-1-propyl-5-[[2'-(tert-butylaminosulfonyl)-2-fluoro-1,1'-biphenyl-4-yl]methyl]-1H-pyrazole-4-carboxylate Following the procedure described in example 79b, but starting from the compound obtained in example 88 and using 2-bromomethylbenzophenone instead of choromethyl pivalate, the title compound was obtained (61%).

mp 49°–51° C.;

¹H-NMR-(CDCl₃) δ (TMS): 0.86 (t, J=7.2 Hz, 3H), 0.99 (s, 9H), 1.27 (d, J=6.4 Hz, 6H), 1.75 (m, 2H), 3.54 (q, J=6.4 Hz, 1H), 3.58 (S, 1H), 3.93 (t, J=7.2 Hz, 2H), 4.41 (s, 2H), 5.32 (s, 2H), 6.8–7.8 (m, 15H), 7.82 (m, 1H).

Analysis calculated for $C_{41}H_{44}FN_3O_5S.2H_2O$: C 66.02%; H 6.49%; N 5.63%; S 4.30%. Found: C 65.93%; H 5.92%; N 5.37%; S 3.77%.

EXAMPLE 91

3-(Phenylcarbonyl)phenylmethyl 3-isopropyl-1-propyl-5-[[2'-(aminosulfonyl)-2-fluoro-1,1'-biphenyl-4-yl]methyl]-1H-pyrazole-4-carboxylate Following the procedure described in example 44, but starting from the compound obtained in example 89, the title compound was obtained (90%).

mp 46°–50° C.;

¹H-NMR-(CDCl₃) δ (TMS): 0.84 (t, J=7.2 Hz, 3H), 1.28 (d, J=6.4 Hz, 6H), 1.75 (m, 2H), 3.55 (q, J=6.4 Hz, 1H), 3.93 (t, J=7.2 Hz, 2H), 4.39 (s, 4H), 5.32 (s, 2H), 6.8–7.8 (m, 15H), 7.82 (m, 1H).

Analysis calculated for $C_{37}H_{36}FN_3O_5S.2.5H_2O$: C 63.54%; H 5.91%; N 6.00%; S 4.58%. Found: C 63.81%; H 5.19%; N 5.91%; S 4.23%.

EXAMPLE 92

2-(Phenylcarbonyl)phenylmethyl 3-isopropyl-1-propyl-5-[[2'-(aminosulfonyl)-2-fluoro-1,1'-biphenyl-4-yl]methyl]-1H-pyrazole-4-carboxylate Following the procedure described in example 44, but starting from the compound obtained in example 90, the title compound was obtained (84%).

mp 49°–51° C.;

¹H-NMR-(CDCl₃) δ (TMS): 0.81 (t, J=7.2 Hz, 3H), 1.19 (d, J=6.4 Hz, 6H), 1.65 (m, 2H), 3.43 (q, J=6.4 Hz, 1H), 3.88 (t, J=7.2 Hz, 2H), 4.27 (s, 4H), 5.37 (s, 2H), 6.8–7.8 (m, 15H), 7.82 (m, 1H).

Analysis calculated for $C_{37}H_{36}FN_3O_5S.2H_2O$: C 64.43%; H 5.84%; N 6.09%; S 4.65%. Found: C 64.68%; H 5.20%; N 5.88%; S 4.25%.

EXAMPLE 93

3-(Phenylcarbonyl)phenylmethyl 3-isopropyl-1-propyl-5-[[2'-(tert-butoxycarbonylaminosulfonyl)-2-fluoro-1,1'-biphenyl-4-yl]methyl]-1H-pyrazole-4-carboxylate Following the procedure described in example 47, but starting from the compound obtained in example 91, the title compound was obtained (72%).

mp 55°–59° C.;

¹H-NMR-(CDCl₃) δ (TMS): 0.81 (t, J=7.2 Hz, 3H), 1.27 (s, 9H), 1.31 (d, J=6.4 Hz, 6H), 1.65 (m, 2H), 3.43 (q, J=6.4 Hz, 1H), 3.88 (t, J=7.2 Hz, 2H), 4.33 (s, 2H), 5.41 (s, 2H), 6.8–7.8 (m, 16H), 7.82 (m, 1H).

Analysis calculated for $C_{42}H_{44}FN_3O_7S.H9O$: C 65.35%; H 6.00%; N 5.44%; S 4.15%. Found: C 65.23%; H 5.78%; N 5.38%; S 3.80%.

EXAMPLE 94

2-(Phenylcarbonyl)phenylmethyl 3-isopropyl-1-propyl-5-[[2'-(tert-butoxycarbonylaminosulfonyl)-2-fluoro-1,1'-biphenyl-4-yl]methyl]-1H-pyrazole-4-carboxylate Following the procedure described in example 47, but starting from the compound obtained in example 92, the title compound was obtained (74%).

mp 57°–61° C.;

¹H-NMR-(CDCl₃) δ (TMS): 0.83 (t, J=7.2 Hz, 3H), 1.28 (s, 9H), 1.19 (d, J=6.4 Hz, 6H), 1.65 (m, 2H), 3.43 (q, J=6.4 Hz, 1H), 3.88 (t, J=7.2 Hz, 2H), 4.27 (s, 2H), 5.37 (s, 2H), 6.8–7.8 (m, 16H), 7.82 (m, 1H).

Analysis calculated for $C_{42}H_{44}FN_3O_7S·1.5H_2O$: C 64.60%; H 6.07%; N 5.38%; S 4.10%. Found: C 64.71%; H 5.71%; N 5.30%; S 3.76%.

EXAMPLE 95

3-Tert-butyl-1-propyl-5-[[2'-(1H-tetrazol-5-yl)-1,1'-biphenyl-4-yl]methyl]-1H-pyrazole-4-carboxylic acid Following the procedure described in example 6, but starting from the compound obtained in reference example 70, the title compound was obtained as a white solid (78%).

mp 195°–197° C.;

¹H-NMR-(CDCl₃) δ (TMS): 0.85 (t, J=7.2 Hz, 3H), 1.43 (s, 9H), 1.63 (m, 2H), 3.90 (t, J=7.2 Hz, 2H), 4.37 (s, 2H), 5.5 (broad s, 2H), 7.10 (s, 4H), 7.5 (m, 3H), 8.0 (m, 1H).

Analysis calculated for $C_{25}H_{28}N_6O_2$: C 67.55%; H 6.35%; N 18.90%. Found: C 67.36%; H 6.32%; N 18.63%.

EXAMPLE 96

3-(Phenylcarbonyl)phenylmethyl 3-isopropyl-1-propyl-5-[[2'-(isobutoxycarbonylaminosulfonyl)-2-fluoro-1,1'-biphenyl-4-]methyl]-1H-pyrazole-4-carboxylate Following the procedure described in example 53, but starting from the compound obtained in example 91, the title compound was obtained (47%).

mp 44°–47° C.;

¹H-NMR-(CDCl₃) δ (TMS): 0.75 (d, J=7.2 Hz, 6H), 0.81 (t, J=7.2 Hz, 3H), 1.31 (d, J=6.4 Hz, 6H), 1.65 (m, 3H), 3.43 (q, J=6.4 Hz, 1H), 3.76 (d, J=6.4 Hz, 2H), 3.92 (t, J=7.2 Hz, 2H), 4.33 (s, 2H), 5.41 (s, 2H), 6.8–7.8 (m, 16H), 7.82 (m, 1H).

Analysis calculated for $C_{42}H_{44}FN_3O_7S·H_2O$: C 65.35%; H 6.00%; N 5.44%; S 4.15%. Found: C 65.55%; H 5.85%; N 5.43%; S 3.95%.

EXAMPLE 97

2-(Phenylcarbonyl)phenylmethyl 3-isopropyl-1-propyl-5-[[2'-(isobutoxycarbonylaminosulfonyl)-2-fluoro-1,1'-biphenyl-4-yl]methyl]-1H-pyrazole-4-carboxylate Following the procedure described in example 53, but starting from the compound obtained in example 92, the title compound was obtained (53%).

mp 52°–59° C.;

¹H-NMR-(CDCl₃) δ (TMS): 0.76 (d, J=7.2 Hz, 6H), 0.91 (t, J=7.2 Hz, 3H), 1.22 (d, J=6.4 Hz, 6H), 1.65 (m, 3H), 3.44 (q, J=6.4 Hz, 1H), 3.76 (d, J=6.4 Hz, 2H), 3.88 (t, J=7.2 Hz, 2H), 4.24 (s, 2H), 5.39 (s, 2H), 6.8–7.8 (m, 16H), 7.82 (m, 1H).

Analysis calculated for $C_{42}H_{44}FN_3O_7S·H_2O$: C 65.35%; H 6.00%; N 5.44%; S 4.15%. Found: C 65.53%; H 5.78%; N 5.38%; S 3.87%.

We claim:
1. A compound of formula I:

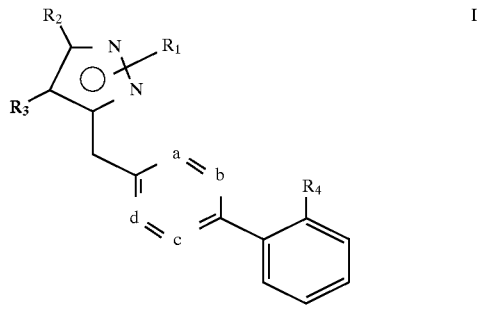

wherein:
$R_1$ represents hydrogen, $C_{1-6}$ alkyl, $C_{1-6}$ haloalkyl, $C_{3-7}$ cycloalkyl, aryl, or —$(CH_2)_m COR_5$;

$R_2$ represents hydrogen, halogen, $C_{1-6}$ alkyl, $C_{1-6}$ haloalkyl, $C_{3-7}$ cycloalkyl, $C_{3-7}$ cycloalkyl$C_{1-4}$ alkyl, $C_{1-6}$ hydroxyalkyl, $C_{1-6}$ alkoxy$C_{1-4}$ alkyl, aryl or aryl$C_{1-4}$ alkyl;

$R_3$ represents hydrogen, —$(CH_2)_n R_6$ or —$(CH_2)_p COR_7$;

either a, b, c and d represent CR or one of a, b, c and d represents N and the remaining groups represent CR, wherein each R independently represents hydrogen, halogen, $C_{1-4}$ alkyl, hydroxy, $C_{1-4}$ alkoxy, nitro, amino, $C_{1-4}$ alkylamino or $C_{1-4}$ dialkylamino;

$R_4$ represents —$CO_2R_8$; -tetrazol-5-yl; tetrazol-5-ylmethyl; —CONH(tetrazol-5-yl); —$CONHSO_2R_9$; —$CONHSO_2$—Het; —$CONHOR_8$; —$CONH_2$; —$CONR_8R_9$; —$COCH_2COR_8$; —$COCH_2CO_2R_8$; —$CONHNHSO_2R_9$; —$CONHNHCONH_2$; —$CH_2NHSO_2R_9$; —$CH_2CO_2R_8$; —$CH_2SO_2NHCOR_8$; —$CH_2SO_2NHCONHR_8$; —$CH_2CONHSO_2R_9$; —$CH_2SO_2NH$—Het; —$CH_2NHCOR_8$; —$NHSO_2R_9$; —$NHCOR_8$; —$NHCONHSO_2R_9$; —$NHSO_2NHCOR_8$; —$SO_3H$; —$SO_2NHR_8$; —$SO_2NHCONH_2$; —$SO_2NHCONR_8R_9$; —$SO_2NHCO_2R_9$; —$SO_2N(CO_2R_9)_2$; —$SO_2NHCOR_8$; —$SO_2NH$—Het; —$SO_2NHCO$—Het; —$PO(OH)_2$; —$PO(OR_9)_2$; —$PO(OH)(OR_9)$; or 3-(trifluoromethyl)-1,2,4-triazol-5-yl; wherein Het represents a 5- or 6-membered aromatic heterocycle in which from 1 to 3 of the ring atoms are nitrogen and/or oxygen and/or sulphur and is optionally substituted with one or two groups chosen from hydroxy, mercapto, $C_{1-4}$ alkyl, $C_{1-4}$ alkoxy, halogen, nitro, $CO_2H$, $CO_2C_{1-4}$ alkyl, amino, $C_{1-4}$ alkylamino and $C_{1-4}$ dialkylamino; and $R_8$ represents hydrogen, $C_{1-4}$ alkyl, aryl, aryl-$(C_{1-4})$alkyl or perfluoro-$(C_{1-4})$ alkyl, and $R_9$ represents $C_{1-4}$ alkyl, aryl, aryl-$(C_{1-4})$ alkyl or perfluoro-$(C_{1-4})$alkyl;

$R_5$ represents hydrogen, hydroxy, $C_{1-6}$ alkyl, $C_{1-6}$ alkoxy, aryl, aryloxy or a group —$NR_{10}R_{11}$;

$R_6$ represents hydroxy, $C_{1-6}$ alkoxy, aryloxy, aryl$C_{1-4}$ alkoxy or $C_{1-6}$ alkylcarbonyloxy;

$R_7$ represents hydrogen, hydroxy, $C_{1-6}$ alkyl, $C_{1-6}$ alkoxy, aryl, aryloxy, aryl$C_{1-4}$ alkoxy, carboxy, $C_{1-4}$ alkoxycarbonyl, a group —$OR_{12}$ or a group —$NR_{10}R_{11}$;

$R_{10}$ and $R_{11}$ independently represent hydrogen or $C_{1-6}$ alkyl;

$R_{12}$ represents $C_{1-6}$ alkylcarbonyloxy$C_{1-4}$ alkyl, $C_{3-7}$ cycloalkylcarbonyloxy$C_{1-4}$ alkyl, $C_{1-6}$ alkoxycarbonyloxy$C_{1-4}$ alkyl, $C_{3-7}$ cycloalkyloxycarbonyloxy$C_{1-4}$ alkyl, $C_{1-6}$ alkoxycarbonylC$_{1-4}$ alkyl, C$_{3-7}$ cycloalkyloxycarbonylC$_{1-4}$ alkyl, C$_{1-6}$ alkylcarbonylaminoC$_{1-4}$ alkyl, C$_{3-7}$ cycloalkylcarbonylaminoC$_{1-4}$ alkyl, a group of formula —(CH$_2$)$_q$R$_{13}$, or a group of formula —(CH$_2$)$_r$OR$_{13}$;

R$_{13}$ represents phenyl optionally substituted with a group arylcarbonyl, C$_{1-6}$ alkylcarbonyl or aryloxy;

m, n, q and r independently represent 1, 2 or 3;

p represents 0, 1 or 2;

aryl, whenever appearing in the above definitions, represents phenyl or phenyl substituted with 1, 2, 3 or 4 groups selected from C$_{1-4}$ alkyl, C$_{1-4}$ haloalkyl, C$_{1-4}$ alkoxy, C$_{1-4}$ haloalkoxy, halogen, nitro, cyano, hydroxy, amino, C$_{1-4}$ alkylamino or C$_{1-4}$ dialkylamino; and the salts and solvates thereof.

2. A compound as claimed in claim 1, in which R$_1$ is adjacent to the biphenylmethyl or phenylpyridylmethyl group thus providing a compound of formula Ia

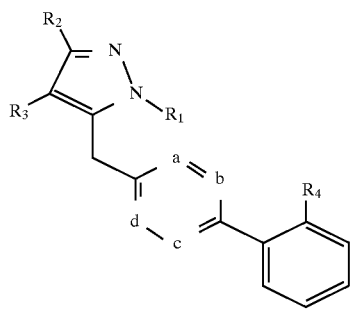

wherein a, b, c, d, R$_1$, R$_2$, R$_3$ and R$_4$ are as defined in claim 1.

3. A compound as claimed in claim 1, wherein R$_1$ represents C$_{1-6}$ alkyl.

4. A compound as claimed in claim 1, wherein a, b, c and d are each CR.

5. A compound as claimed in claim 1, wherein R$_2$ represents hydrogen, C$_{1-6}$ alkyl, C$_{3-7}$ cycloalkyl, C$_{3-7}$ cycloalkylC$_{1-4}$ alkyl, aryl or arylC$_{1-4}$ alkyl.

6. A compound as claimed in claim 1, wherein R$_3$ represents —COR$_7$.

7. A compound as claimed in claim 1, wherein R$_4$ represents —CO$_2$R$_8$; -tetrazol-5-yl; —NHSO$_2$R$_9$; —SO$_2$NHR$_8$; —SO$_2$NHCO$_2$R$_9$ or —SO$_2$NHCOR$_8$.

8. A compound as claimed in claim 1 selected from:
1-butyl-3-ethyl-5-[[2'-(1H-tetrazol-5-yl)-1,1'-biphenyl-4-yl]methyl]-1H-pyrazole-4-carboxylic acid;
1-butyl-3-methyl-5-[[2'-(1H-tetrazol-5-yl)-1,1'-biphenyl-4-yl]methyl]-1H-pyrazole-4-carboxylic acid;
3-isopropyl-1-propyl-5-[[2'-(1H-tetrazol-5-yl)-1,1'-biphenyl-4-yl]methyl]-1H-pyrazole-4-carboxylic acid;
3-ethyl-1-propyl-5-[[2'-(1H-tetrazol-5-yl)-1,1'-biphenyl-4-yl]methyl]-1H-pyrazole-4-carboxylic acid;
3-cyclopropyl-1-propyl-5-[[2'-(1H-tetrazol-5-yl)-1,1'-biphenyl-4-yl]methyl]-1H-pyrazole-4-carboxylic acid;
3-cyclopropyl-1-propyl-5-[[2'-(1H-tetrazol-5-yl)-1,1'-biphenyl-4-yl]methyl]-1H-pyrazole-4-carboxamide;
1-butyl-3-isopropyl-5-[[2'-(1H-tetrazol-5-yl)-1,1'-biphenyl-4-yl]methyl]-1H-pyrazole-4-carboxylic acid;
3-methyl-1-propyl-5-[[2'-(1H-tetrazol-5-yl)-1,1'-biphenyl-4-yl]methyl]-1H-pyrazole-4-carboxylic acid;
1-butyl-5-[[2'-(1H-tetrazol-5-yl)-1,1'-biphenyl-4-yl]methyl]-1H-pyrazole-4-carboxylic acid;
3-ethyl-5-[[2'-(phenylcarbonylaminosulfonyl)-1,1'-biphenyl-4-yl]methyl]-1-propyl-1H-pyrazole-4-carboxylic acid;
3-isopropyl-1-propyl-5-[[2'-(1H-tetrazol-5-yl)-2-fluoro-1,1'-biphenyl-4-yl]methyl]-1H-pyrazole-4-carboxylic acid; and
3-Tert-butyl-1-propyl-5-[[2'-(1H-tetrazol-5-yl)-1,1'-biphenyl-4-yl]methyl]-1H-pyrazole-4-carboxylic acid; or a salt or solvate thereof.

9. A pharmaceutical composition which comprises an effective amount of a compound of formula I as claimed in claim 1 or a pharmaceutically acceptable salt or solvate thereof in admixture with a pharmaceutically acceptable excipient.

10. A process for preparing a compound of formula I as defined in claim 1, which comprises:

A) reacting a compound of formula II with a compound of formula III

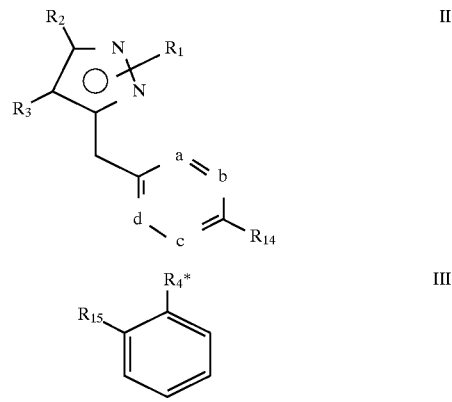

wherein a, b, c, d, R$_1$, R$_2$ and R$_3$ are as defined in claim 1, R$_4$* represents a group R$_4$ or a group convertible thereto, and either one of R$_{14}$ and R$_{15}$ represents halogen, methanesulfonyloxy, toluenesulfonyloxy or trifluoromethanesulfonyloxy and the other represents a group —Sn(R$_{16}$)$_3$, —B(OH)$_2$ or —B(OR$_{17}$)(OR$_{18}$) or both of them represent halogen, wherein R$_{16}$ represents a C$_{1-4}$ alkyl group and R$_{17}$ and R$_{18}$ represent each C$_{1-4}$ alkyl or R$_{17}$ and R$_{18}$ together with the oxygen atoms to which they are linked and the boron atom form a 1,3,2-dioxaborane or a 1,3,2-dioxaborolane ring, which is optionally substituted with C$_{1-4}$ alkyl groups, followed, if necessary, by the conversion of a group R$_4$* into a group R$_4$ and/or the removal of any protecting group present; or B) reacting a compound of formula IV

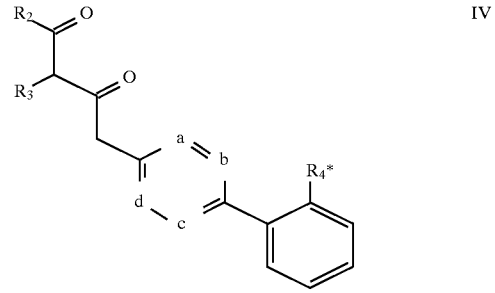

wherein a, b, c, d, R$_2$ and R$_3$ are as defined in claim 1 and R$_4$* into a group R$_4$ or a group convertible thereto with a compound of formula R$_1$NHNH$_2$ (V), followed, if necessary, by the conversion of a group R$_4$* into a group R$_4$ and/or the removal of any protecting group present; or C) deprotecting a compound of formula I'

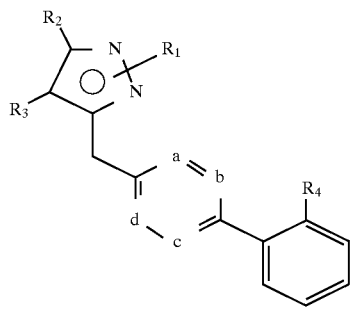

wherein a, b, c, d, $R_1$, $R_2$, $R_3$ and $R_4$ are as defined in claim 1 but at least one of them contains a protecting group; or D) converting, in one or a plurality of steps, a compound of formula I into another compound of formula I; and E) if desired, after steps A, B, C or D treating a compound of formula I with an acid or a base to give the corresponding salt.

11. A compound of general formula II

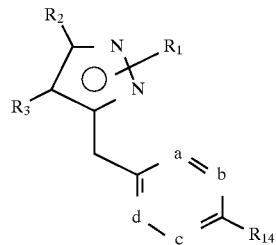

wherein a, b, c, d, $R_1$, $R_2$ and $R_3$ are as defined in claim 1 and $R_{14}$ represents halogen, methanesulfonyloxy, toluenesulfonyloxy, trifluoromethanesulfonyloxy, a group —Sn($R_{16}$)$_3$, —B(OH)$_2$ or —B(O$R_{17}$)(O$R_{18}$), wherein $R_{16}$ represents a $C_{1-4}$ alkyl group and $R_{17}$ and $R_{18}$ represent each $C_{1-4}$ alkyl or $R_{17}$ and $R_{18}$ together with the oxygen atoms to which they are linked and the boron atom form a 1,3,2-dioxaborane or a 1,3,2-dioxaborolane ring, which is optionally substituted with $C_{1-4}$ alkyl groups.

12. A method of treating or preventing diseases or medical conditions in a mammal in which angiotensin II is involved comprising administering to a mammal in need thereof a pharmaceutically effective amount of a compound according to claim 1 or a pharmaceutically acceptable salt or solvate thereof.

13. The method according to claim 12 wherein said mammal is a human.

14. A method of treating or preventing hypertension in a mammal comprising administering to mammal in need thereof a pharmaceutically effective amount of a compound according to claim 1 or a pharmaceutically acceptable salt or solvate thereof.

15. The method according to claim 14 wherein said mammal is a human.

16. A method of treating or preventing congestive heart failure in a mammal comprising administering to a mammal in need thereof a pharmaceutically effective amount of a compound according to claim 1 or a pharmaceutically acceptable salt or solvate thereof.

17. The method according to claim 16 wherein said mammal is a human.

18. A method of treating or preventing elevated intraocular pressure in a mammal comprising administering to a mammal in need thereof a pharmaceutically effective amount of a compound according to claim 1 or a pharmaceutically acceptable salt or solvate thereof.

19. The method according to claim 18 wherein said mammal is a human.

* * * * *